US012643855B2

(12) United States Patent
Karpenko et al.

(10) Patent No.: US 12,643,855 B2
(45) Date of Patent: Jun. 2, 2026

(54) FLUOROGENIC DIMER COMPOUND, USEFUL AS A PROBE FOR DETECTION OF ENDOGENOUS RECEPTORS

(71) Applicants: UNIVERSITE DE STRASBOURG, Strasbourg (FR); CENTRE NATIONAL DE LA RECHERCHE SCIENTIFIQUE, Paris (FR)

(72) Inventors: Julie Karpenko, Illkirch-Graffenstaden (FR); Andrey Klymchenko, Illkirch-Graffenstaden (FR); Dominique Bonnet, Geispolsheim (FR); Mayeul Collot, Illkirch-Graffenstaden (FR)

(73) Assignees: UNIVERSITE DE STRASBOURG, Strasbourg (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 826 days.

(21) Appl. No.: 17/924,369

(22) PCT Filed: May 12, 2021

(86) PCT No.: PCT/EP2021/062626

§ 371 (c)(1),
(2) Date: Nov. 10, 2022

(87) PCT Pub. No.: WO2021/228939

PCT Pub. Date: Nov. 18, 2021

(65) Prior Publication Data

US 2023/0174480 A1 Jun. 8, 2023

(30) Foreign Application Priority Data

May 12, 2020 (EP) .................................... 20305479

(51) Int. Cl.

| | |
|---|---|
| ***C07D 209/26*** | (2006.01) |
| ***C07D 209/43*** | (2006.01) |
| ***C07D 403/14*** | (2006.01) |
| *G01N 33/58* | (2006.01) |

(52) U.S. Cl.
CPC ......... *C07D 209/26* (2013.01); *C07D 209/43* (2013.01); *C07D 403/14* (2013.01); *G01N 33/582* (2013.01)

(58) Field of Classification Search
CPC .. C07D 209/26; C07D 209/43; C07D 403/14; G01N 33/582; C09B 23/0066; C09B 69/00; C09B 23/083
See application file for complete search history.

(56) References Cited

FOREIGN PATENT DOCUMENTS

WO WO 2017/205336 11/2017

OTHER PUBLICATIONS

Bédard, M. et al. "Conjugation of multivalent ligands to gold nanoshells and designing a dual modality imaging probe" *Journal of Materials Chemistry B*, 2015, pp. 1788-1800, vol. 3.
Romieu, A. et al. "Postsynthetic Derivatization of Fluorophores with α-Sulfo-β-alanine Dipeptide Linker. Application to the Preparation of Water-Soluble Cyanine and Rhodamine Dyes" *Bioconjugate Chemistry*, 2008, pp. 279-289, vol. 19, No. 1.
Written Opinion in International Application No. PCT/EP2021/062626, Aug. 2, 2021, pp. 1-9.
Herbst, E. et al. "FRET-based cyanine probes for monitoring ligation reactions and their applications to mechanistic studies and catalyst screening" *Organic & Biomolecular Chemistry*, Jan. 2016, pp. 3715-3728, vol. 14, No. 15.
Karpenko, I. A. et al. "Fluorogenic Squaraine Dimers with Polarity-Sensitive Folding As Bright Far-Red Probes for Background-Free Bioimaging" *Journal of the American Chemical Society*, Dec. 15, 2014, pp. 405-412, vol. 137, No. 1.

*Primary Examiner* — Robert S Cabral
(74) *Attorney, Agent, or Firm* — SALIWANCHIK, LLOYD & EISENSCHENK

(57) ABSTRACT

The present disclosure relates to a novel fluorogenic dimer compound, useful as a probe for detection of endogenous receptors, in particular G protein-coupled receptors. The present invention provides compositions and kits comprising such compound and methods of labeling a biomolecule, comprising the step of contacting the biomolecule with the compound of the invention.

19 Claims, 1 Drawing Sheet

FLUOROGENIC DIMER COMPOUND, USEFUL AS A PROBE FOR DETECTION OF ENDOGENOUS RECEPTORS

CROSS-REFERENCE TO RELATED APPLICATION

This application is the U.S. national stage application of International Patent Application No. PCT/EP2021/062626, filed May 12, 2021.

FIELD OF THE INVENTION

The present disclosure relates to a novel fluorogenic dimer compound, useful as a probe for detection of endogenous receptors, in particular G protein-coupled receptors. The present invention provides compositions and kits comprising such compound and methods of labeling a biomolecule, comprising the step of contacting the biomolecule with the compound of the invention.

BACKGROUND OF THE INVENTION

Fluorescent probes can be used in studying G protein-coupled receptor (GPCR) in living cells, however their application to the whole animal receptor imaging is still in its infancy.

G protein-coupled receptors (GPCRs) are the largest family of the transmembrane receptors in humans. GPCRs are involved in virtually all aspects of human physiology in health and disease. Not surprisingly, GPCRs are molecular targets of more than 30% of currently drugs on the market. Each member of the GPCR family has a unique tissue-dependent expression and localization pattern which is crucial for paying its physiological and physiopathological roles. Thereby, to correlate a level of GPCR expression to a disease, it is crucial to access their spatial distribution at the cell but also the organismal levels.

Regarding the whole-organism molecular imaging techniques, fluorescence-based contrast agents emit non-ionizing radiation and have longer shelf lifetime comparing with radioisotope-based probes. Moreover, fluorescence properties of organic dyes can be modulated in a wide range by chemical modifications. Few reports have been focused on the imaging of transgenic GPCRs in living mice. For instance, Ma et al. imaged the al-AR receptor in a xenografts model using a far-red dye-ligand conjugate (Z. Ma, Y. Lin, Y. Cheng, W. Wu, R. Cai, S. Chen, B. Shi, B. Han, X. Shi, Y. Zhou, et al., *J. Med. Chem.* 2016, 59, 2151-2162). More recently, Alcobia et al. used the β2-adrenergic receptor fused to the bioluminescent reporter NanoLuc enabling the detection of the receptor-ligand binding by BRET (D. C. Alcobia, A. I. Ziegler, A. Kondrashov, E. Comeo, S. Mistry, B. Kellam, A. Chang, J. Woolard, S. J. Hill, E. K. Sloan, *iScience* 2018, 6, 280-288). However, no example of fluorescence imaging of endogenous GPCRs has been reported in mice, mostly due to the low expression level of many endogenous GPCRs and the lack of appropriate fluorescent probes.

Ideally, a fluorescent probe for the in vivo imaging of endogenous GPCRs should meet the following requirements: 1) high affinity and selectivity for its target; 2) absorption and emission in the near-infrared (NIR) region to minimize the light scattering in tissues and to enhance tissue penetration; 3) a fluorogenic character to “turn on” its fluorescence after binding to the target receptor to ensure a high signal-to-noise ratio. Fluorogenic dyes have been successfully used for background-free detection and imaging of various analytes, and have been developed for the detection of ligand-GPCR binding in living cells (I. A. Karpenko, R. Kreder, C. Valencia, P. Villa, C. Mendre, B. Mouillac, Y. Mély, M. Hibert, D. Bonnet, A. S. Klymchenko, *ChemBioChem* 2014, 15, 359-363; I. A. Karpenko, A. S. Klymchenko, S. Gioria, R. Kreder, I. Shulov, P. Villa, Y. Mély, M. Hibert, D. Bonnet, *Chem. Commun.* 2015, 51, 2960-2963). Recently, it was reported the concept of fluorogenic squaraine dimers with environment-sensitive folding which allowed for the visualization of GPCRs in living cells in no-wash conditions with a high signal-to-noise ratio (I. A. Karpenko, M. Collot, L. Richert, C. Valencia, P. Villa, Y. Mély, M. Hibert, D. Bonnet, A. S. Klymchenko, *J. Am. Chem. Soc.* 2015, 137, 405-412). In aqueous medium, the formation of the dimer of H-aggregate type resulted in complete fluorescence quenching of the probe. In contrast, once bound to the receptor, the fluorophores were exposed to a hydrophobic environment of the biomembrane, which led to dissociation of the dimer and recovery of fluorescence. Although the squaraine dimer is a powerful tool for receptor labelling in living cells, it displays absorption and emission in the far-red region which is not optimal for the in vivo imaging.

The oxytocin receptor OTR, an endogenous GPCR, is known to be involved in the modulation of complex social behavior such as social recognition, attachment, empathy, trust, and is proposed as a potential therapeutic target for the treatment of the autistic spectrum disorders. In mice, the OTR is highly expressed in the uterus during pregnancy and in the mammary glands during late pregnancy and lactation. However, direct in vivo optical imaging of this receptor and GPCRs in general remains a challenge so far.

Here, it is disclosed the design and the synthesis of the first near-infrared (NIR) emitting fluorogenic dimer with environment-sensitive folding. Such NIR probe comprising cyanine dyes showed an unprecedented brightness allowing for the first time the background-free detection of an endogenous GPCR, such the oxytocin receptor (OTR), in living mice. The planarity of the cyanine π system leads to aggregations in aqueous solution which phenomenon is often viewed as a drawback to use such dyes. Here, due to the formation of non-fluorescent H-aggregates in aqueous medium, the near-infrared fluorogenic dimer displays a strong turn-on response (up to 140-fold) in apolar environment and exceptional brightness: 56% quantum yield and ≈444 000 $M^{-1}$ $cm^{-1}$ extinction coefficient. Grafted on a ligand of the oxytocin receptor, it allows the unprecedented background-free and target-specific imaging of the naturally expressed receptor in living mice.

The key element in the design of the NIR fluorogenic dimer probe for the OTR is the choice of the fluorophore. In addition to operation in the NIR window (700-950 nm), the fluorophore should be bright, photostable and sufficiently water-soluble. For this purpose, it is provided herein an original compound which is a cyanine derivative dimer decorated with polyethylene glycol chains, which allows the lipophilic character of the dye to be compensated and allows avoiding non-specific interactions.

SUMMARY OF THE INVENTION

The present disclosure thus provides a novel fluorogenic dimer compound, which can be used as a probe for detection of endogenous GPCRs in mammals, more particularly in living mammals. The present invention provides compositions and kits comprising such compound and methods of labeling a molecular target, comprising the step of contacting the molecular target with the compound of the invention.

These and other objects and embodiments of the invention will become more apparent after the detailed description of the invention.

DETAILED DESCRIPTION

Figure 1:
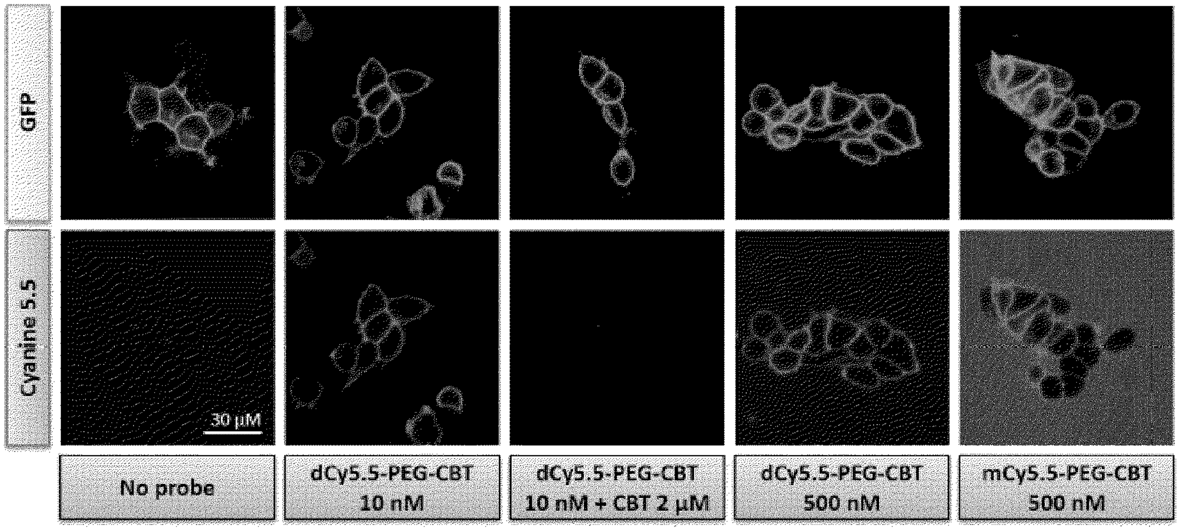
FIG. 1: Confocal microscopy studies of dCy5.5-PEG-CBT and mCy5.5-PEG-CBT on living HEK 293 cells expressing OTR-GFP fusion under no-wash conditions. Cells were incubated with the ligands for 5 min at room temperature prior to the imaging.

Unless otherwise defined, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

"About", "around" or "approximately" as used herein when referring to a measurable value such as an amount, a temporal duration, and the like, is meant to encompass variations of 20% or ±10%, more preferably ±5%, even more preferably ±1%, and still more preferably ±0.1% from the specified value, as such variations are appropriate to perform the disclosed methods or compositions.

Ranges: throughout this disclosure, various aspects of the invention can be presented in a range format. It should be understood that the description in range format is merely for convenience and brevity and should not be construed as an inflexible limitation on the scope of the invention.

Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the invention, the term "comprise(s)" or "comprising" (and other comparable terms, e.g., "containing," and "including") is "open-ended" and can be generally interpreted such that all of the specifically mentioned features and any optional, additional and unspecified features are included. According to specific embodiments, it can also be interpreted as the phrase "consisting essentially of" where the specified features and any optional, additional and unspecified features that do not materially affect the basic and novel characteristic(s) of the claimed invention are included or the phrase "consisting of" where only the specified features are included, unless otherwise stated.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, $22^{nd}$ ed.; Allen et al., Eds.; The Pharmaceutical Press, 2012; Handbook of Pharmaceutical Excipients, $7^{th}$ ed.; Rowe et al., Eds.; The Pharmaceutical Press: 2012; Handbook of Pharmaceutical Additives, $3^{rd}$ ed.; Ash and Ash Eds.; Gower Publishing Company: 2007; Pharmaceutical Preformulation and Formulation, $2^{nd}$ ed.; Gibson Ed.; CRC Press LLC: Boca Raton, Fla., 2009.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a non-crystalline form. Where the solvent is water, the solvate is a hydrate. Examples of hydrates include, but are not limited to, a hemihydrate, monohydrate, dihydrate, trihydrate, tetrahydrate, and pentahydrate.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human. Preferably the subject is a human patient whatever its age or sex. New-borns, infants, children are included as well.

As used herein, the abbreviations for any protective groups, amino acids and other compounds, are, unless indicated otherwise, in accord with their common usage or recognized abbreviations including abbreviations found in J. Org. Chem. 2007, 72, 23A-24A or abbreviations established by the IUPAC-IUB Commission on Biochemical Nomenclature (Biochem. 1972, 11, 942-944).

Compounds of the Invention

The invention concerns a compound, which is a fluorogenic dimer with two cyanine moieties (D), which is represented by the following formula (1): D-L-D (1);

where (D) is represented by the following formula (I) or (I'):

(I)

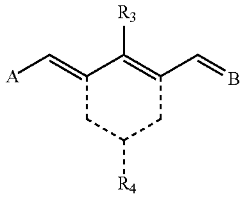

or

-continued (I')

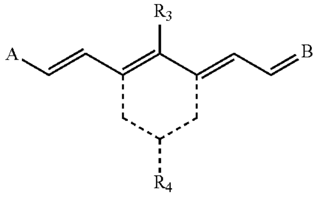

wherein:

(A) has the following formula:

(A)

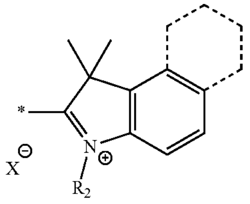

(B) has the following formula:

(B)

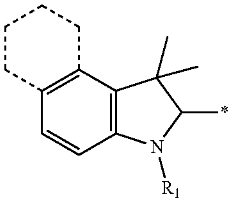

where the dashed lines are present or not, when they are present, they represent single or double bonds;

$R_2$ comprises or consists of a $(C_2\text{-}C_{10})$alkyl group substituted by a functional group consisting of —COOH, —$SO_3H$, and OH; a polyethylene glycol represented by the formula —$(CH_2CH_2O)_n$—R'; or a polypropylene glycol represented by the formula —$(CH_2CH_2(CH_3)O)_n$—R', wherein n is an integer from 1 to 40, and R' is an alkyl group in $C_1$-$C_{12}$, comprising optionally at least one functional group consisting of —COOH, —$SO_3H$, and OH;

$R_3$ represents:

an hydrogen atom, a halogen atom, preferably fluorine (F), a group chosen from a $(C_1\text{-}C_{20})$alkyl, a cyclo$(C_3\text{-}C_{20})$alkyl, a $(C_2\text{-}C_{20})$alkenyl, a $(C_2\text{-}C_{20})$alkynyl, a $(C_1\text{-}C_5)$alkyl-NR"R"' (R" and R"' being independently H or a $(C_1\text{-}C_5)$alkyl), a heterocyclic group, a cyclo$(C_3\text{-}C_{20})$alkenyl, a heterocyclo$(C_2\text{-}C_{20})$alkenyl, an aryl, a heteroaryl, a hetero$(C_1\text{-}C_{20})$alkyl, a $(C_1\text{-}C_{20})$alkylaryl, and a $(C_1\text{-}C_{20})$alkylheteroaryl, said group being unsubstituted or substituted by one or two substituents chosen from a $(C_1\text{-}C_5)$ alkyl, an aryl, an aryl$(C_1\text{-}C_5)$alkyl, —$CONR_{11}R_{12}$, or —$R_{13}COOH$, $R_{11}$ and $R_{12}$ being independently an hydrogen, a $(C_1\text{-}C_{20})$ alkyl, a di$(C_1\text{-}C_5)$alkylamino$(C_1\text{-}C_5)$alkyl, possibly substituted by one or more halogen atoms, preferably F, or hydroxy groups, polyethylene glycol represented by the formula —$(CH_2CH_2O)_n$—R'; or a polypropylene glycol represented by the formula —$(CH_2CH_2(CH_3)O)_n$—R', wherein n is an integer from 1 to 40 and R' is an alkyl group in $C_1$-$C_{12}$, or, alternatively, $R_{11}$ and $R_{12}$ represents with the nitrogen to which they are attached an heterocycle (such as piperazine) possibly substituted by a $(C_1\text{-}C_4)$alkyl, $R_{13}$ being a $(C_1\text{-}C_{10})$ alkyl, one substituent can optionally be substituted by one or two substituents as defined herein, or a group of formula -E-$R_{10}$, wherein E is chosen from —O—, —S—, —NR"— (R" being H or a $(C_1\text{-}C_4)$ alkyl), and —$CH_2$—; and $R_{10}$ is chosen from a $(C_1\text{-}C_{20})$alkyl, a cyclo$(C_3\text{-}C_{20})$alkyl, a $(C_2\text{-}C_{20})$alkenyl, a $(C_2\text{-}C_{20})$alkynyl, a $(C_1\text{-}C_5)$alkyl-NR"R"' (R" and R"' being independently H or a $(C_1\text{-}C_5)$alkyl), a heterocyclic group, a cyclo$(C_3\text{-}C_{20})$alkenyl, a heterocyclo$(C_2\text{-}C_{20})$alkenyl, an aryl, a heteroaryl, a hetero$(C_1\text{-}C_{20})$ alkyl, a $(C_1\text{-}C_{20})$alkylaryl, a $(C_1\text{-}C_{20})$alkylheteroaryl, $R_{10}$ being unsubstituted or substituted by one to three substituents chosen from a $(C_1\text{-}C_5)$ alkyl, an aryl, an aryl$(C_1\text{-}C_5)$alkyl, —$CONR_{11}R_{12}$, or —$R_{13}COOH$;

$R_{11}$ and $R_{12}$ being independently an hydrogen, a $(C_1\text{-}C_{20})$ alkyl, a di$(C_1\text{-}C_5)$alkylamino$(C_1\text{-}C_5)$alkyl, possibly substituted by one or more halogen atoms or hydroxy groups, or, alternatively, or alternatively $R_{11}$ and $R_{12}$ represents with the nitrogen to which they are attached an heterocycle (such as piperazine) possibly substituted by a $(C_1\text{-}C_4)$alkyl, $R_{13}$ being a $(C_1\text{-}C_{10})$ alkyl, one substituent can optionally be substituted by one or two substituents as defined herein, $R_4$, if present, represents:

an hydrogen atom, a group chosen from a $(C_1\text{-}C_{20})$alkyl, a cyclo$(C_3\text{-}C_{20})$alkyl, a $(C_2\text{-}C_{20})$alkenyl, a $(C_2\text{-}C_{20})$alkynyl, a heterocyclic group, a cyclo$(C_3\text{-}C_{20})$alkenyl, a heterocyclo$(C_2\text{-}C_{20})$alkenyl, an aryl, a heteroaryl, a hetero$(C_1\text{-}C_{20})$alkyl, a $(C_1\text{-}C_{20})$alkylaryl, or a $(C_1\text{-}C_{20})$alkylheteroaryl, said group being unsubstituted or substituted by one or two substituents chosen from a $(C_1\text{-}C_5)$ alkyl, an aryl, or —$R_{13}COOH$, $R_3$ being a $(C_1\text{-}C_{20})$ alkyl, or a group of formula -E-$R_{10}$, wherein E is chosen from —O—, —S—, —NH—, —$CH_2$—; $R_{10}$ is chosen from a $(C_1\text{-}C_{20})$alkyl, a cyclo$(C_3\text{-}C_{20})$alkyl, a $(C_2\text{-}C_{20})$alkenyl, a $(C_2\text{-}C_{20})$alkynyl, a heterocyclic group, a cyclo$(C_3\text{-}C_{20})$alkenyl, a heterocyclo$(C_2\text{-}C_{20})$alkenyl, an aryl, a heteroaryl, a hetero$(C_1\text{-}C_{20})$alkyl, a $(C_1\text{-}C_{20})$alkylaryl, a $(C_1\text{-}C_{20})$alkylheteroaryl, $R_{10}$ being unsubstituted or substituted by one to three substituents chosen from a $(C_1\text{-}C_5)$ alkyl, an aryl, or —$R_{13}COOH$, $R_{13}$ being a $(C_1\text{-}C_{10})$ alkyl;

$R_1$ is a saturated or unsaturated hydrocarbon chain attached to an extremity of L in formula (1), L is a saturated or unsaturated hydrocarbon group presenting three extremities and comprising from 2 to 40, preferably from 2 to 30, carbon atoms, where two extremities of said linker L are covalently bond to both cyanine moieties of formulae (I) or (I'), via both $R_1$, and the third extremity is the remainder of the saturated or unsaturated hydrocarbon group and comprises a reactive group or is attached to a ligand;

the hydrocarbon chain or group (i.e. $R_1$ or L, independently) is optionally interrupted by one or several heteroatoms, by one or several connecting groups, or by one or several carbon cycles or heterocycles, the hydrocarbon chain ($R_1$ or L, independently) may be further substituted by one or several groups selected from $C_1$-$C_3$ alkyl groups, halogens, preferably F, —OH, —OMe, and —$CF_3$;

the reactive group comprises at least one heteroatom and is able to form a covalent bond to another reactive group, forming thereby a connecting group; and X is an anion bearing a negative charge.

Preferably, the connecting group is selected from —O—, C(═O) —OC(O)—, —C(O)O—, —OC(O)O—, —S—, —SS—, —SC(O)—, —OC(S)—, —$NR_{21}$—, —$NR_{21}$C(O)—, —C(O)$NR_{21}$—, —$NR_{21}$C(S)—, —C(S)$NR_{21}$—, —OC(O)S—, —OC(S)O—, —SC(O)O—, —OC(S)S—, —SC(O)S—, —SC(S)O—, —SC(S)S—, —OC(O)$NR_{21}$—, —OC(S)$NR_{21}$—, —$NR_{21}$C(S)O—, —$NR_{21}$C(O)S—, —$NR_{21}$C(O)$NR_{22}$—, —$NR_{21}$C(S)$NR_{22}$—, —SC(O)S—, —SC(S)O—, —S(O)—, —S$(O)_2$—, —O($CR_{21}R_{22}$)O—, —C(O)O($CR_{21}R_{22}$)O—, —OC(O)O($CR_{21}R_{22}$)O—, —P(O)($R_{21}$)—, —P(O)($OR_{21}$)—, —P(O)($R_{21}$)O—, —OP(O)($OR_{21}$)—, —OP(O)($R_{21}$)O—, —$NR_{21}$P(O)($R_{22}$)—, —$NR_{21}$P(O)($OR_{22}$)—, —$NR_{21}$P(O)($R_{22}$)O—, —OP(O)($OR_{21}$)— and —OP(O)($R_{21}$)O—, wherein $R_{21}$ and $R_{22}$ are independently H or $CH_3$, preferably H; In the present description the term "alkyl", alone or in combination, refers to a branched or unbranched saturated hydrocarbon group having the indicated number of carbon atoms. As used herein, the term "(Cx-Cy)alkyl", wherein x and y respectively being a different positive integer, is meant to an alkyl group having from x to y number of carbon atoms. For example, the terms "($C_1$-$C_{20}$)alkyl", "($C_1$-$C_{10}$)alkyl", "($C_5$-$C_{20}$)alkyl", "($C_{12}$-$C_{18}$)alkyl" as used herein respectively refer to an alkyl group having from 1 to 20 carbon atoms, from 1 to 10 carbon atoms, from 8 to 20 carbon atoms or from 12 to 18 carbon atoms.

Examples of alkyl can be, but not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, n-docenyl, n-tridecyl, n-tetradecyl, n-pentadecyl, n-hexadecyl, n-heptadecyl, n-octadecyl, n-nonadecyl, n-icosyl.

The terms "hetero($C_1$-$C_{10}$)alkyl", "hetero($C_1$-$C_{20}$)alkyl", and "hetero($C_5$-$C_{20}$)alkyl" respectively refer to a ($C_1$-$C_{10}$) alkyl group, a ($C_1$-$C_{20}$)alkyl group or a ($C_5$-$C_{20}$)alkyl group as defined before in which one or more carbon atoms are replaced by an oxygen, nitrogen, phosphorus or sulfur.

Example of a heteroalkyl can be an alkyloxy (methoxy, ethoxy, etc.), alkylmercapto (methylmercapto, ethylmercapto, etc.), or an alkyloxyethyl (methoxyethyl, etc.), etc.

The term "cycloalkyl" refers to a cyclic saturated carbon-based ring composed of at least three carbon atoms. The terms "cyclo(3-20)alkyl", "cyclo(3-10)alkyl" or "cyclo(8-20)alkyl" respectively refer to an cycloalkyl composed of from 3 to 20 carbon atoms, from 3 to 10 carbon atoms, or from 8 to 20 carbon atoms.

Examples of cycloalkyl groups include, but are not limited to, cyclopropyl, cyclobutyl, cyclopentyl, cyclohexyl, cycloheptyl, cyclooctyl, cyclononyl, cyclodecyl, cyclotetradecyl, cyclohexadecyl, cycloheptadecyl, cyclooctadecyl, cyclononadecyl, cycloicosyl.

The term "alkenyl" as used herein, alone or in combination, refers to a branched or unbranched hydrocarbon group of the indicated number of carbon atoms having at least one carbon-carbon double bond. The terms "($C_2$-$C_{20}$)alkenyl", "($C_2$-$C_{10}$)alkenyl" or "($C_5$-$C_{20}$)alkenyl" signify respectively an alkenyl group of 2 to 20 atoms, an alkenyl group of 2 to 10 carbon atoms or an alkenyl group of 8 to 20 carbon atoms.

Examples of alkenyl group are ethenyl, 1-propenyl, 2-propenyl, isopropenyl, 1-butenyl, 2-butenyl, 3-butenyl, isobutenyl, 1-pentenyl, 1-hexenyl, 1-heptenyl, 1-octenyl, 1-nonenyl, 2-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-eicosenyl, 1,3-butadienyl, 1,4-pentadienyl.

The term "cycloalkenyl" refers to a cyclic unsaturated carbon-based ring composed of at least 3 carbon atoms and containing at least one carbon-carbon double bond. The terms "cyclo(3-20)alkenyl", "cyclo(3-10)alkenyl" and "cyclo(8-20)alkenyl" signify respectively a cycloalkenyl having 3-20 carbon atoms, a cycloalkenyl having 3-10 carbon atoms or a cycloalkenyl having 8-20 carbon atoms.

Examples of cycloalkenyl groups include, but are not limited to, cyclopropenyl, cyclobutenyl, cvclopentenyl, cyclopentadienyl, cyclohexenyl, cyclohexadienyl, cycloheptenyl, cyclooctenyl, and the like.

The terms "heterocycloalkenyl" as used herein refers to a heterocyclic unsaturated carbon-based ring comprising at least two carbon atoms and at least one heteroatom chosen from oxygen, nitrogen, phosphorus or sulfur. The terms "heterocyclo($C_2$-$C_{20}$)alkenyl", "heterocyclo($C_2$-$C_{10}$)alkenyl" and "heterocyclo($C_5$-$C_{20}$)alkenyl" respectively refer to a heterocycloalkenyl having 2-20 carbon atoms, having 2-10 carbon atoms, or having 8-20 carbon atoms.

The term "alkynyl" as used herein, alone or in combination, means a branched or unbranched hydrocarbon group of the indicated number of atoms comprising at least a triple bond between two carbon atoms. The terms "($C_2$-$C_{20}$) alkynyl", "($C_2$-$C_{10}$)alkynyl", or "($C_5$-$C_{20}$)alkynyl respectively denote an alkynyl group having 2 to 20 carbon atoms, 2 to 10 carbon atoms, or 8 to 20 carbon atoms. Examples of alkynyl groups include ethynyl, propynyl, butynyl, octynyl, etc.

The term "aryl" as employed herein alone or as part of another group refers to monocyclic and bicyclic aromatic groups containing 6 to 10 carbons in the ring portion. Examples of aryl include phenyl and naphthyl.

The term "($C_1$-$C_{20}$)alkylaryl" and "($C_1$-$C_{10}$)alkylaryl" respectively refer to an aryl group as defined being substituted by an ($C_1$-$C_{20}$)alkyl group or an ($C_1$-$C_{10}$)alkyl group.

The term "heteroaryl" refers to an aryl group, in which one or more carbon atoms are replaced by an oxygen, a nitrogen, or a sulfur, for example the 4-pyridyl, 2-imidazolyl, 3-pyrazolyl and isochinolinyl group.

The term "aryl($C_1$-$C_{10}$)alkyl" or "an aryl($C_1$-$C_5$)alkyl" refers to a ($C_1$-$C_{10}$)alkyl or ($C_1$-$C_5$)alkyl as defined before being substituted by an aryl, such as benzyl or phenethyl.

The terms "($C_1$-$C_{20}$)alkylheteroaryl" and "($C_1$-$C_{10}$)alkylheteroaryl" respectively mean a heteroaryl group as defined before being substituted by a ($C_1$-$C_{20}$)alkyl group or a ($C_1$-$C_{10}$)alkyl group.

The term "carbocyclic group" or "carbocycle" refers to an aromatic or a non-aromatic hydrocarbon monocycle or polycycle (comprising fused, bridged or spiro rings). Advantageously, the carbocycle comprises 3 to 15, notably 5 to 10 carbon atoms in the ring.

The term "heterocyclic group" or "heterocycle" refers to a carbocyclic group, in which one or more carbon atoms are replaced by one or more oxygen, nitrogen, phosphorus, or sulfur atoms. It refers more specifically to an aromatic or a non-aromatic hydrocarbon monocycle or polycycle (comprising fused, bridged or spiro rings), in which one or more, advantageously 1 to 4, and more advantageously 1 or 2, carbon atoms have each been replaced with a heteroatom selected from nitrogen, oxygen and sulphur atoms. Advantageously, the heterocycle comprises 5 to 15, notably 5 to 10 atoms in the ring.

A heterocyclic group can be a heteroaryl, a heterocycloalkyl, a heterocycloalkenyl, etc. Examples of heterocyclic group include furyl, pyrrolyl, imidazolyl, thiazolyl, isothiazolyl, pyrrolidinyl, piperazinyl, pyridyl, quinolyl, pyrimidinyl.

The term “halogen” means fluorine, chlorine, bromine or iodine.

According to the present invention, the compound of formula (1) thus presents 2 moieties of formula (D), as detailed herein, linked together by L (via $R_1$ of both D moieties). Each D moiety can be different or preferably identical.

In some embodiments, $R_1$ is a saturated hydrocarbon chain comprising from 1 to 20, preferably from 2 to 10, carbon atoms. According to a particular embodiment, $R_1$ is a saturated hydrocarbon chain from 3 to 6 carbon atoms, preferably an alkyl group from 3 to 6 carbon atoms (such as of formula $—(CH_2)x$- where x is 3, 4, 5, or 6).

In some embodiments, L is a saturated hydrocarbon chain presenting three extremities and comprising from 2 to 40, preferably from 2 to 30, carbon atoms, where two extremities of said linker L are covalently bond to both $R_1$, and the third extremity is a branched moiety of the saturated hydrocarbon group and comprises a reactive group or is attached to a ligand. The hydrocarbon chain of L is optionally interrupted by one or several heteroatoms, such as nitrogen and oxygen atoms, by connecting groups comprising heteroatoms as defined above, such as amide groups (—CONH—), or by one or several carbon cycles or heterocycles, the hydrocarbon chain may be substituted or not by one or several groups selected from $C_1$-$C_3$ alkyl groups, halogens, such as F, Cl or Br, —OH, —OMe, and $—CF_3$.

In some embodiments, the linker L is a hydrocarbon group interrupted by one or more ethyleneoxy groups (i.e. $(CH_2CH_2O)o$ with o is from 1 to 5, preferably 1 or 2), ethylene groups (i.e. $(CH_2CH_2)r$ with r is from 1 to 5, preferably 1 or 2), and interrupted by one or more connecting groups (as defined above), and preferably selected in the group consisting of: —O—, —NH—, —C(═O)—, —C(═O)NH—, —OC(═O)—, —(C═O)O—, —NHC(═O)—, —C(═O)NH—, —NHC(═O)NH—, —NHC(═O)O—, and —OC(═O)NH—, or more preferably —NHC(═O)— or —C(═O)NH—.

According to a preferred embodiment, the third extremity is a branched moiety of the hydrocarbon group and comprises a reactive group able to react in a click reaction or a bioconjugation reaction.

X is an anion bearing a negative charge. X can be an organic or inorganic counterion.

According to an embodiment, X is an anion of acetic acid, 2,2-dichloroacetic acid, trifluoroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(15)-camphor-10-sulfonic acid, capric acid, caproic acid, caprylic acid, cinnamic acid, citric acid, cyclamic acid, cyclohexanesulfamic acid, dodecyl sulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, a-oxoglutaric acid, glycolic acid, hippuric acid, hydrobromic acid, hydrochloric acid, hydroiodic acid, (+)-L-lactic acid, (+)-DL-lactic acid, lactobionic acid, lauric acid, maleic acid, (−)-L-malic acid, malonic acid, (+)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In another embodiment, X is a fluoride (F—), chloride (Cl—), bromide (Br—), iodide (I—), acetate ($CH_3CO_2$—), trifluoroacetate ($CF_3CO_2$—) (named as TFA), phosphate ($PO_4H^2$—, $PO_4H^2$, or $PO_4^3$—), or sulfate ($HSO_4$ or $SO_4^2$—).

In yet another embodiment, X is a chloride or trifluoroacetate.

In a particular embodiment, $R_2$ is a polyethylene glycol represented by the formula $—(CH_2CH_2O)_n—R'$; or a polypropylene glycol represented by the formula $—(CH_2CH_2(CH_3)O)_n—R'$, wherein n is an integer from 1 to 40, in particular n is from 5 to 15, in particular n=6 to 10, in particular n=8, and R' is an alkyl group in $C_1$-$C_{12}$, in particular $C_1$-$C_5$, and more specifically $CH_3$.

In another particular embodiment, $R_2$ is a polyethylene glycol represented by the formula $—(CH_2CH_2O)_n—R'$; or a polypropylene glycol represented by the formula $—(CH_2CH_2(CH_3)O)_n—R'$, wherein n is an integer from 1 to 40, in particular n is from 5 to 15, in particular n=6 to 10, in particular n=8, and R' is an alkyl group in $C_1$-$C_{12}$, comprising at least one functional group consisting of —COOH, $—SO_3H$, and OH.

In another particular embodiment, $R_2$ is a ($C_2$-$C_{10}$)alkyl group substituted by at least one functional group consisting of —COOH, $—SO_3H$, and OH. According to a more specific embodiment, the said functional group is attached to the alkyl group at its extremity.

According to another embodiment, the compound of the invention is of formula (1) where the dashed lines are present in formulas (I) or (I') and preferably represent single bond. According to a more particular embodiment, $R_4$ is a hydrogen atom.

In a particular embodiment, formulas (I) and (I') are as follows:

(I)

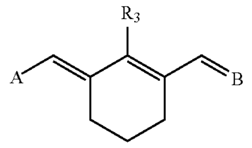

(I')

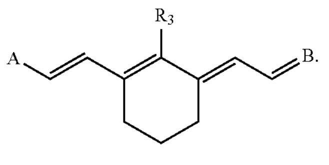

According to another embodiment, the compound of the invention is of formula (1) where the dashed lines are not present in formulas (I) or (I') (and therefore where $R_4$ is absent).

According to this preferred embodiment, (D) is represented by the following formula (I) or (I'):

(I)

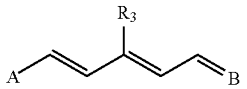

or (I')

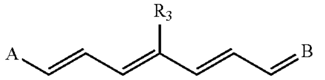

wherein A, B and $R_3$ are as defined above including preferred embodiments. Preferably, $R_3$ is H.

According to a more preferred embodiment, (D) is represented by the following formula (I):

(I)

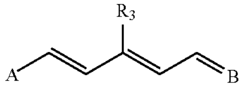

wherein A, B and $R_3$ are as defined above including preferred embodiments. Preferably, $R_3$ is H.

According to a preferred embodiment, the formula (A) is as follows:

(A1)

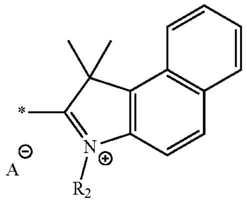

According to a preferred embodiment, the formula (B) is as follows:

(B1)

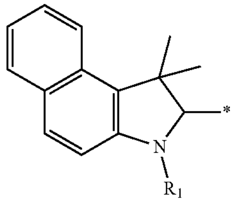

According to a preferred embodiment, the compound is of formula (1) where A is A1 and B is B1, and more preferably where (D) is represented by the following formula (I):

(I)

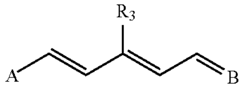

According to an embodiment, $R_4$, if present, is selected from the group consisting of an hydrogen, a ($C_1$-$C_{20}$)alkyl, a cyclo($C_3$-$C_{20}$)alkyl, a ($C_2$-$C_{20}$)alkenyl, a ($C_2$-$C_{20}$)alkynyl, a heterocyclic group, a cyclo($C_3$-$C_{20}$)alkenyl, a heterocyclo ($C_2$-$C_{20}$)alkenyl, an aryl, a heteroaryl, a hetero($C_1$-$C_{20}$) alkyl, a ($C_1$-$C_{20}$)alkylaryl, and a ($C_1$-$C_{20}$)alkylheteroaryl, said group being unsubstituted or substituted by one or two substituents chosen from a ($C_1$-$C_5$) alkyl, an aryl, or —$R_{13}$COOH, $R_{13}$ being a ($C_1$-$C_{20}$) alkyl; preferably $R_4$, if present, is selected from the group consisting of an hydrogen, an unsubstituted ($C_1$-$C_{20}$)alkyl, an unsubstituted cyclo ($C_3$-$C_{20}$)alkyl, an unsubstituted ($C_2$-$C_{20}$)alkenyl, a unsubstituted ($C_2$-$C_{20}$)alkynyl, an unsubstituted heterocyclic group, an unsubstituted cyclo($C_3$-$C_{20}$)alkenyl, an unsubstituted heterocyclo($C_2$-$C_{20}$)alkenyl, an unsubstituted aryl, an unsubstituted heteroaryl, an unsubstituted hetero($C_1$-$C_{20}$) alkyl, an unsubstituted ($C_1$-$C_{20}$)alkylaryl, and an unsubstituted ($C_1$-$C_{20}$)alkylheteroaryl.

According to an embodiment, $R_3$ is selected from the group consisting of an hydrogen, an unsubstituted ($C_1$-$C_{20}$) alkyl, an unsubstituted cyclo($C_3$-$C_{20}$)alkyl, an unsubstituted ($C_2$-$C_{20}$)alkenyl, a unsubstituted ($C_2$-$C_{20}$)alkynyl, an unsubstituted heterocyclic group, an unsubstituted cyclo($C_3$-$C_{20}$) alkenyl, an unsubstituted heterocyclo($C_2$-$C_{20}$)alkenyl, an unsubstituted aryl, an unsubstituted heteroaryl, an unsubstituted hetero($C_1$-$C_{20}$)alkyl, an unsubstituted ($C_1$-$C_{20}$)alkylaryl, or an unsubstituted ($C_1$-$C_{20}$)alkylheteroaryl.

According to another embodiment, $R_3$ can be a group selected in the group consisting of:

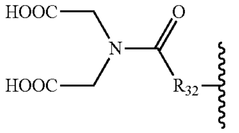

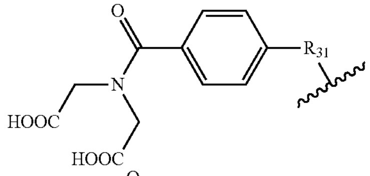

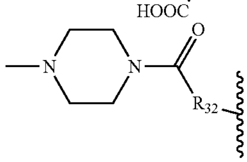

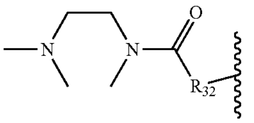

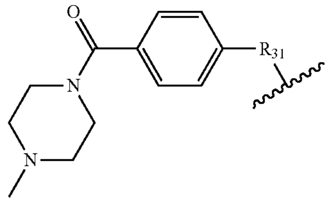

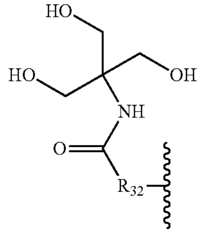

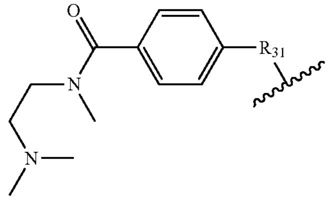

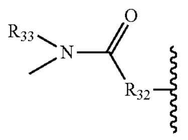

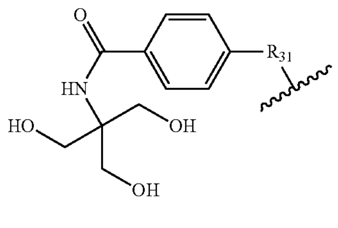

wherein $R_{31}$ is absent, O, S or NR", and $R_{32}$ is $-CH_2-$ or $-O-$, and $R_{33}$ is a polyethylene glycol represented by the formula $-(CH_2CH_2O)_n-R'$; or a polypropylene glycol represented by the formula $-(CH_2CH_2(CH_3)O)_n-R'$, wherein n is an integer from 1 to 40 and R' is an alkyl group in $C_1$-$C_{12}$.

According to a particular embodiment, the compound is of formula (1) where (D) is represented by formula (I) or (I') which is as follows:

(I)

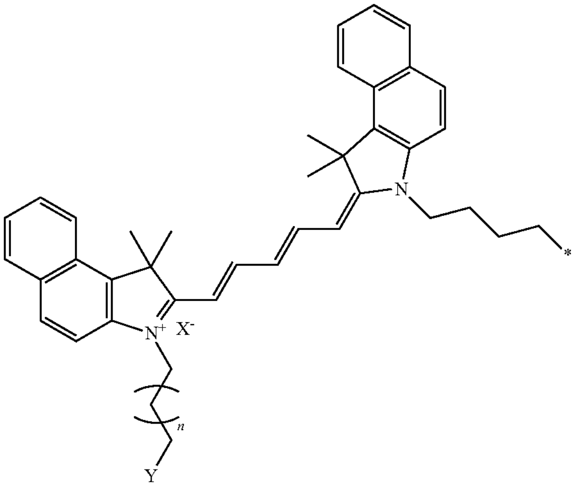

(I')

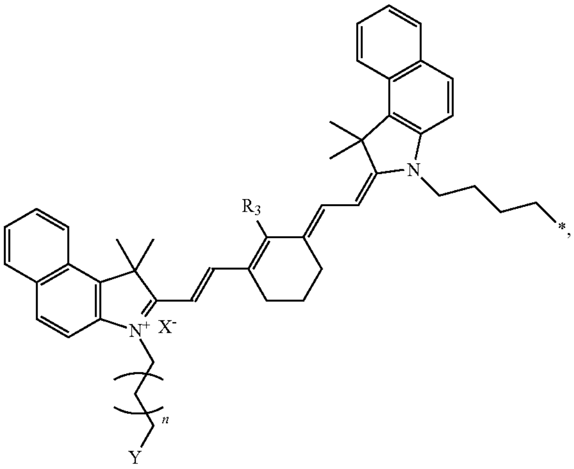

, wherein X and $R_3$ are as defined herein, including the detailed specific embodiments, n is 0-8, and Y is a functional group consisting of $-COOH$, $-SO_3H$, and OH.

According to another particular embodiment, the compound is of formula (1) where (D) is represented by formula (I') which is as follows:

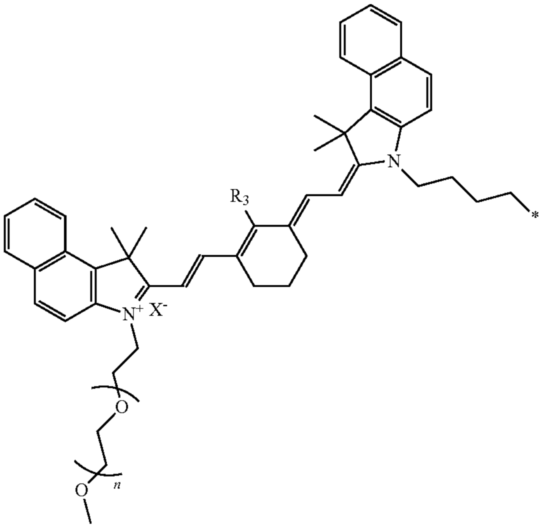

or

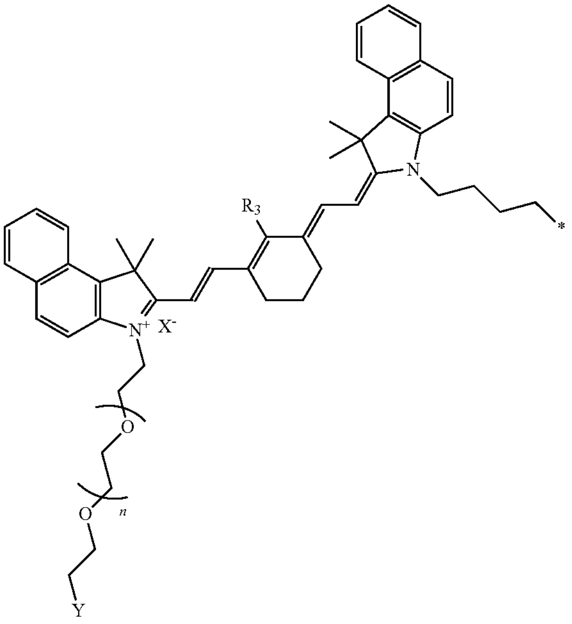

wherein X and $R_3$ are as defined herein, including the detailed specific embodiments, n is 0-8, and Y is a functional group consisting of $-COOH$, $-SO_3H$, and OH.

According to another particular embodiment, the compound is of formula (1) where (D) is represented by the following formula (I'):

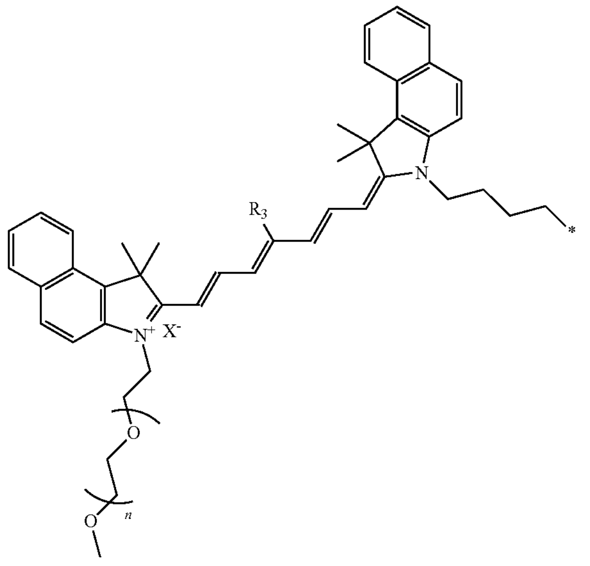

wherein X and $R_3$ are as defined herein, including the detailed specific embodiments, and n is 0-8, preferably 5, 6 or 7.

According to particular embodiments, $R_3$ (and $R_4$, if present) are hydrogen atoms.

According to particular embodiment, the compound of the invention comprises a ligand linked to the compound via the linker L, and more specifically at the third extremity of L as defined above. Preferably, before being attached thereto, the compound of the invention and the ligand each bears a reactive group able to react together through a click reaction or a bioconjugation reaction.

In particular, the click reaction may be selected from the group consisting of copper-catalyzed azide-alkyne dipolar cycloaddition (CuAAC), strain promoted alkyne-azide cycloaddition (SPAAC), Diels-Alder reactions with tetrazines and strained alkynes or alkenes, tetrazine-isonitrile cycloaddition thiol-alkene click reaction such as maleimide-cysteine cycloaddition, and a sydnone-alkyne cycloaddition, preferably is a strain promoted alkyne-azide cycloaddition (SPAAC).

In some aspects, the click reaction may be "bioorthogonal" or "biocompatible", this means that the reagents involved in the click reaction may react selectively and rapidly with each other in the presence of a plurality of biological entities. In some embodiments, the click reaction may be conducted in media comprising living cells, without interfering with cellular process.

Accordingly, the compound of the invention can bear an azido group, as reactive group, while the reactive group of the ligand can bear an alkyne group or a strained alkyne scaffold, and vice versa. Preferably, the strained alkynyl group is selected from cyclooctyne scaffolds, such as azadibenzocyclooctyne (ADIBO, DIBAC or DBCO) or tetramethoxy dibenzo cyclooctyne (TMDIBO). Other appropriate strained alkynes frequently used for copper-free reaction include: cyclooctyne (OCT), aryl-less cyclooctyne (ALO), monofluorocyclooctyne (MOFO), difluorocyclooctyne (DIFO), dibenzocyclooctyne (DIBO), dimethoxyazacyclooctyne (DIMAC), biarylazacyclooctynone (BARAC), bicyclononyne (BCN), tetramethylthiepinium (TMTI, TMTH), difluorobenzocyclooctyne (DIFBO), oxa-dibenzocyclooctyne (ODIBO), carboxymethylmonobenzocyclooctyne (COMBO), or benzocyclononyne.

The ligand is any compound able to specifically bind the molecular target and comprising at least one binding domain which is able to interact with the fluorogenic dimer (i.e. the compound of the invention) through covalent or non-covalent interactions, directly or through a binding intermediary. Examples of the ligand include, but are not limited to, an antibody, a fragment or derivative of an antibody, an aptamer, a spiegelmer, a peptide aptamer, a chemical ligand (agonist and antagonist) or a substrate of the molecular target, a nucleic acid capable of hybridizing a molecular target. The ligand, according to a particular embodiment, is a synthetic chemical ligand or a substrate of a molecular target.

Accordingly, the compound of Formula (1) comprises the hydrocarbon group L with a third extremity which is the remainder of the saturated or unsaturated hydrocarbon group and comprises a reactive group, or which is the remainder of the saturated or unsaturated hydrocarbon group and which is linked to a ligand, preferably covalently linked to a ligand.

As used herein, the term "molecular target" refers to any kind of molecules to be recovered, detected and/or quantified. The molecular target can be a biomolecule, i.e. a molecule that is present in living organisms, examples of biomolecules include, but are not limited to, nucleic acids, e.g. DNA or RNA molecules, proteins such as antibodies, enzymes or growth factors, lipids such as fatty acids, glycolipids, sterols or glycerolipids, vitamins, hormones, neurotransmitters, and carbohydrates, e.g., mono-, oligo- and polysaccharides. The terms "polypeptide", "peptide" and "protein" are used interchangeably to refer to a polymer of amino acid residues, and are not limited to a minimum length. The protein may comprise any post-translational modification such as phosphorylation, acetylation, amidation, methylation, glycosylation or lipidation. As used herein, the term "nucleic acid" or "polynucleotide" refers to a polymeric form of nucleotides of any length, either ribonucleotides or deoxyribonucleotides. Preferably, the molecular target is a protein or a nucleic acid. More preferably, the molecular target is a protein and is more particularly a membrane receptor, such as a GPCR.

According to a particular embodiment, the ligand is a ligand of a GPCR, and more specifically, the ligand is carbetocin (CBT), a peptidic ligand for oxytocin receptor (OTR), and the GPCR is OTR.

In yet another embodiment, the compound of the invention has a formula selected from:

(2)
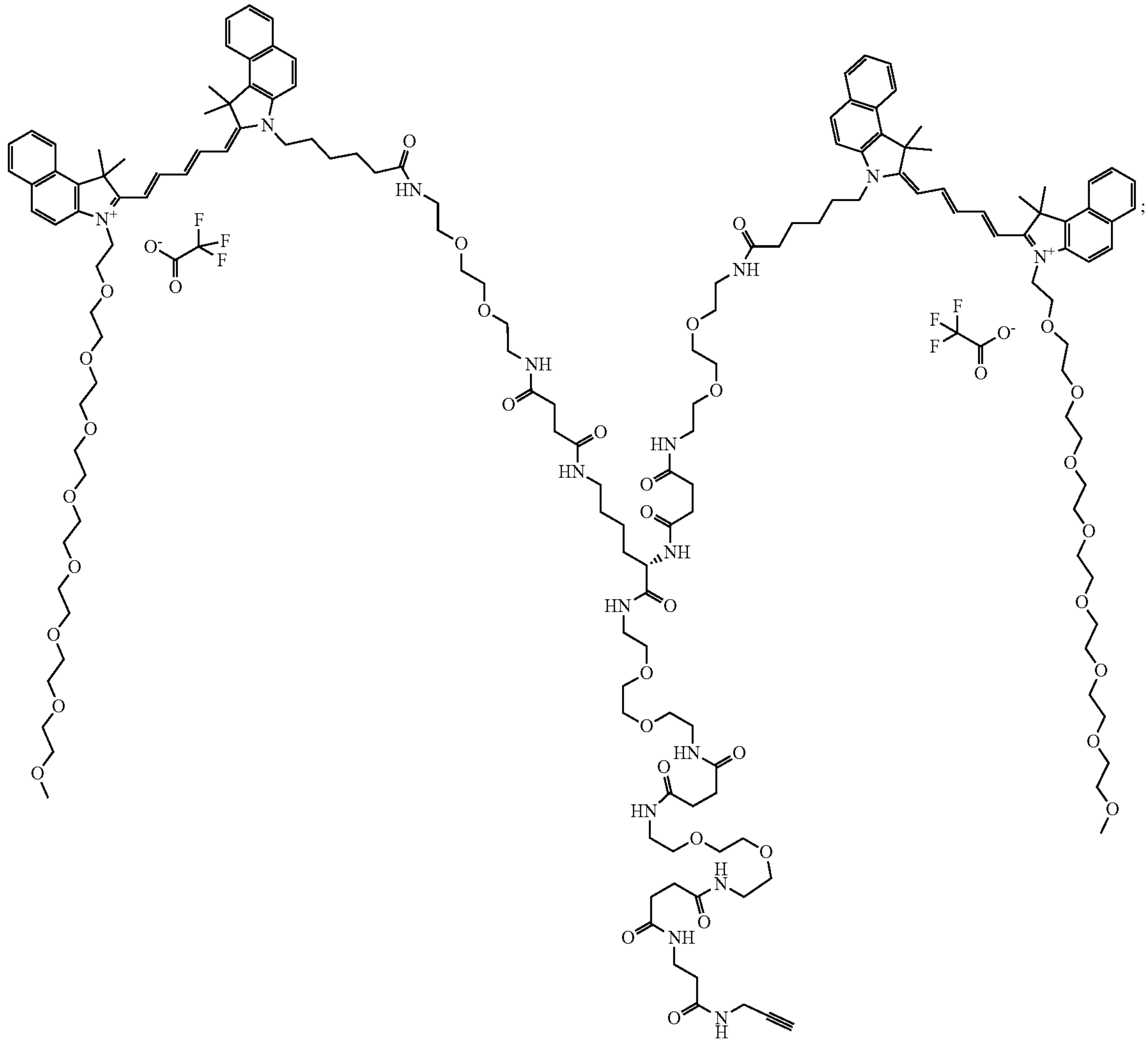
; and
dCy5.5-PEG

-continued
(3)
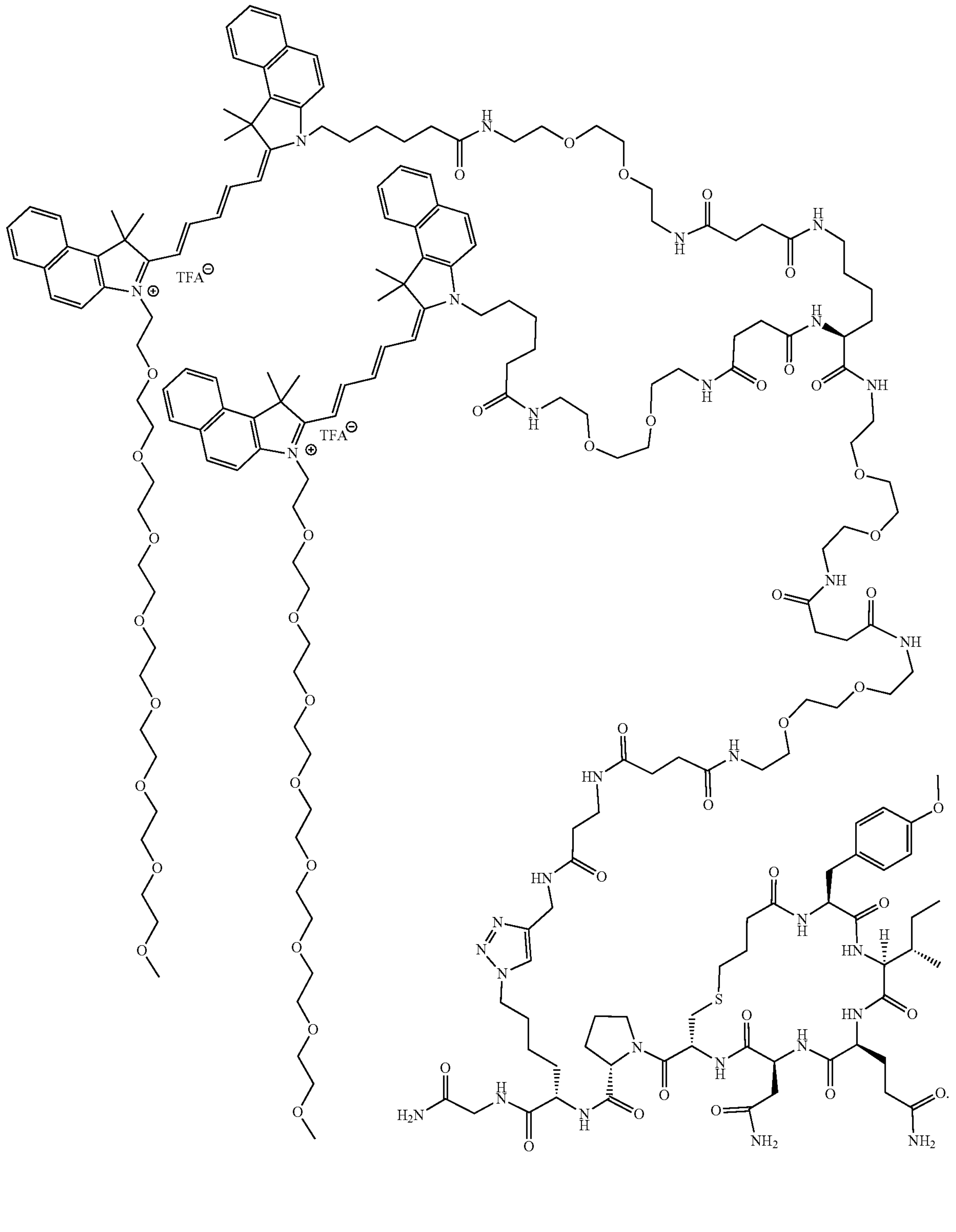
Said compounds of formulas (2) and (3) are also named dCY5.5-PEG and dCY5.5-PEG-CBT, respectively. $TFA^-$ which represents the counterion X can be replaced by any other anion as defined above.

According to another particular embodiment, the compound of the invention has a formula selected from:

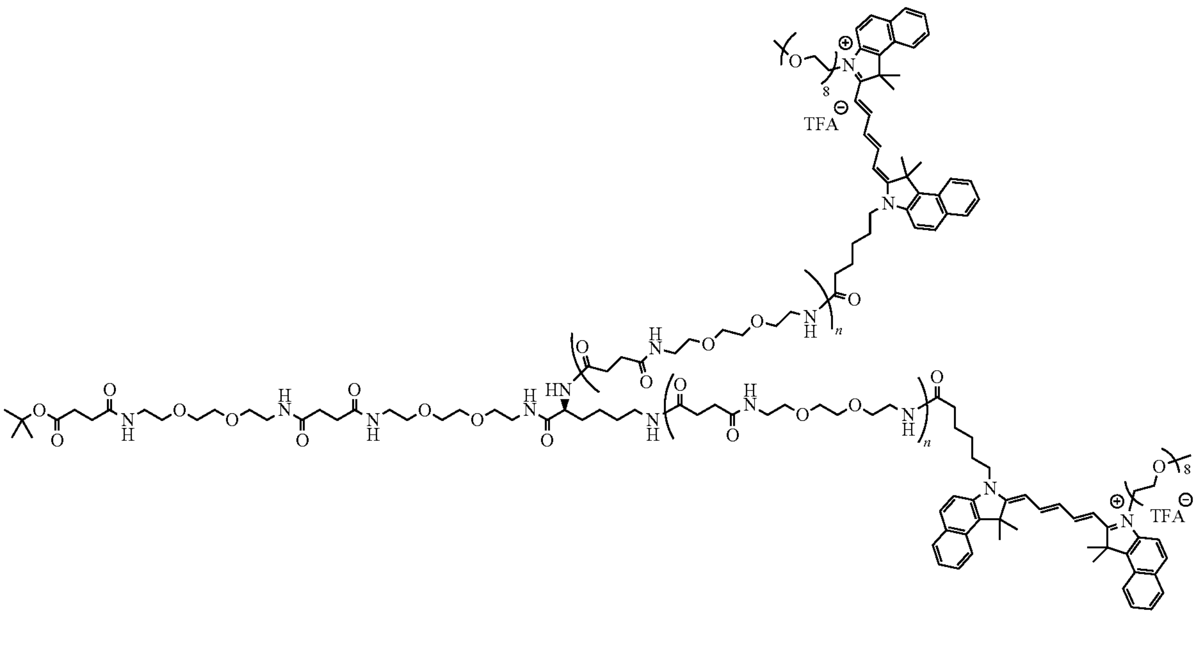

wherein n is 0 or 1 (compounds 4 and 5 respectively);

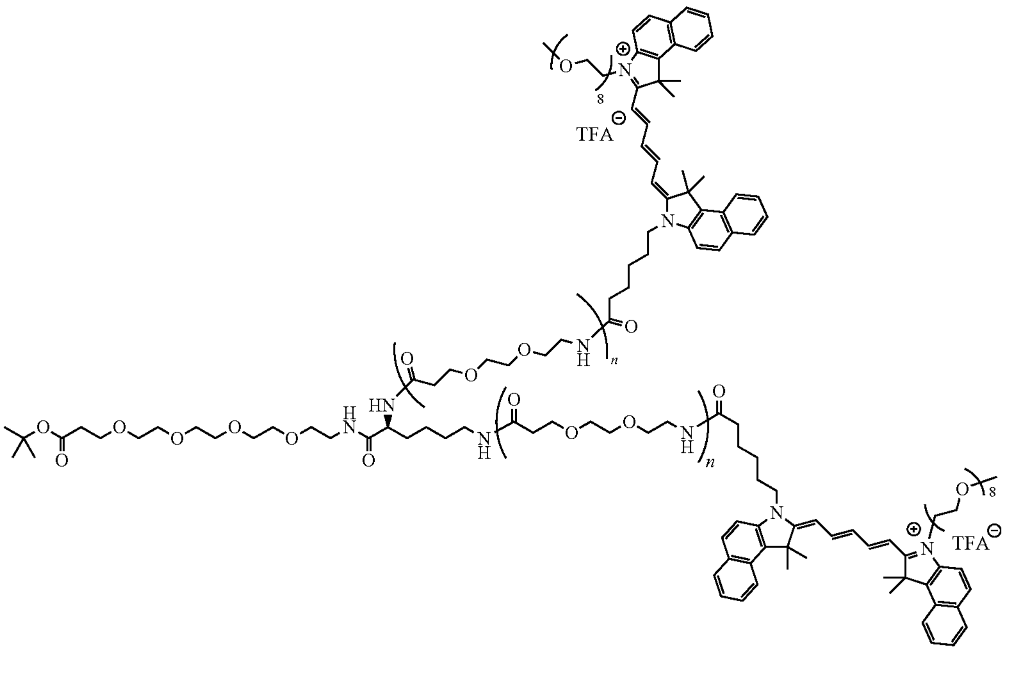

wherein n is 0 or 1 (compounds 6 and 7 respectively).

TFA⁻ which represents the counterion X can be replaced by any other anion as defined above.

Methods of Preparation

The compounds provided herein can be prepared, isolated, or obtained by any method known to one of skill in the art. In certain embodiments, and by way of examples, compounds of the invention can be prepared as detailed in the Examples below.

The starting materials used in the synthesis of the compounds provided herein are either commercially available or can be readily prepared.

The pharmaceutical composition provided herein can also be formulated to be targeted to a particular tissue, receptor, or other area of the body of the subject to be treated, including liposome-, resealed erythrocyte-, and antibody-based delivery systems.

Pharmaceutical Compositions

In one embodiment, provided herein is a pharmaceutical composition comprising a compound provided herein, e.g., a compound of Formula (1), or a pharmaceutically acceptable solvate or hydrate thereof, and a pharmaceutically acceptable excipient.

The pharmaceutical composition that comprises a compound provided herein, e.g., a compound of Formula (1), or a pharmaceutically acceptable solvate or hydrate thereof, can be formulated in various dosage forms for oral, parenteral, and topical administration. The pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Delivery Technology, $2^{nd}$ ed.; Rathbone et al., Eds.; Marcel Dekker, Inc.: New York, N.Y., 2008).

In one embodiment, the pharmaceutical composition is provided in a dosage form for oral administration, which comprises a compound provided herein, e.g., a compound of Formula (1), or a pharmaceutically acceptable solvate or hydrate thereof.

In another embodiment, the pharmaceutical composition is provided in a dosage form for parenteral administration, which comprises a compound provided herein, e.g., a compound of Formula (1), or a pharmaceutically acceptable solvate or hydrate thereof.

In yet another embodiment, the pharmaceutical composition is provided in a dosage form for topical administration, which comprises a compound provided herein, e.g., a compound of Formula (1), or a pharmaceutically acceptable solvate or hydrate thereof.

Methods of Use

In one embodiment, provided herein is a method of labeling in vitro, ex vivo or in vivo a molecular target, comprising the step of contacting the molecular target with a compound disclosed herein, e.g., a compound of Formula (1), or a pharmaceutically acceptable solvate or hydrate thereof. According to a preferred embodiment, compound of Formula (1) comprises a ligand as defined above.

The molecular target thus labeled is suitable for biological imaging, pharmacological studies, or clinical diagnosis.

In one embodiment, the contacting step is performed at a pH ranging from about 5 to about 9 or from about 6 to about 8. In another embodiment, the contacting step is performed at a pH of about 6, about 6.2, about 6.4, about 6.6, about 6.8, about 7.0, about 7.2, about 7.4, about 7.6, about 7.8, or about 8.

In one embodiment, the contacting step is performed at a temperature ranging from about 0 to about 50° C., from about 10 to about 40° C., from about 20 to 40° C., or from about 30 to about 40° C. In another embodiment, the contacting step is performed at a temperature ranging from about 35 to about 40° C.

In one embodiment, the contacting step is performed at an aqueous solution.

In one embodiment, the contacting step is performed under physiological conditions.

In one embodiment, the molecular target is a biomolecule which is an amino acid based compound. In another embodiment, the biomolecule is a protein. In another embodiment, the biomolecule is a membrane receptor. In yet another embodiment, the biomolecule is an endogenous GPCR, such as OTR.

The amino acid based compound can be attached to the compositions or compound disclosed herein via the amine, amino, carboxylic acid, or sulfhydryl group.

The molecular target thus labeled is suitable for biological imaging, drug delivery, clinical diagnosis, forensics, in vitro, ex vivo diagnostics, and in vivo diagnostics. Non-limiting applications include drug delivery, immunotherapy, imaging contrast medium or agent, flow cytometry, cell sorting, microscopy, in situ hybridization, immune histochemistry, enzyme-linked immunosorbent assays (ELISA), Western blot, immunoprecipitation, microarrays, near-infrared imaging, etc.

The biomolecule thus labeled is suitable for biological imaging, clinical diagnosis, drug delivery, forensics, or in vitro diagnostics. Non-limiting applications include amplification (polymerase chain reaction, transcription mediated amplification, strand displacement, loop-mediated isothermal amplification, rolling circle amplification, ligase chain reaction, nucleic acid sequence based amplification, multiple displacement amplification, helicase dependent amplification, ramification amplification, etc.), real time amplification, sequencing (sanger, real-time, ion semiconductor, synthesis, ligation, nanopore, etc.), detection probes, fluorescent in situ hybridization, antisense technology, microarrays, etc.

The molecular target can be included or from any sample, typically a biological sample of a subject, e.g. a fluid, such as a sample of blood, plasma, serum, urine, cerebrospinal fluid or a sample from a tissue of a subject or a part thereof. Examples of such samples include fluids such as blood, plasma, saliva, urine and seminal fluid samples, as well as biopsies, organs, tissues, or cell samples. It can also include the whole body of a subject or a part thereof (in vivo labeling). The sample may be treated prior to be in contact with the compound of the invention.

Kits

In one embodiment, provided herein is a kit which includes a container and at least one compound provided herein, e.g., a compound of Formula (1), or a pharmaceutically acceptable solvate or hydrate thereof. The compound of Formula (1) can comprise a ligand or a reactive group, as defined above.

According to a particular embodiment, the kit can comprise one or several (2, 3, 4, 5, 6 up to 10 different compounds of formula (1), including 2, 3, 4, 5, 6 up to 10 different compounds of formula (1).

The kit can further comprise a ligand (as defined above) bearing a reactive group able to react through a click reaction or a bioconjugation reaction with the reactive group of the linker L of the compound of formula (1).

The kit provided herein can further include a device that is used to administer the compound provided herein. Examples of such devices include, but are not limited to, syringes, needle-less injectors drip bags, patches, and inhalers.

The kit provided herein can further include a pharmaceutically acceptable vehicle that can be used to administer one or more the compound provided herein. For example, if the compound provided herein is provided in a solid form that must be reconstituted for parenteral administration, the kit can comprise a sealed container of a suitable vehicle in which the compound can be dissolved to form a sterile solution that is suitable for parenteral administration.

In another embodiment is a kit for diagnostics or research use. Included in these kits is optionally a molecular target labeled with a compound disclosed herein, e.g., a compound of Formula (1), or a pharmaceutically acceptable solvate or hydrate thereof.

The following examples are given for purposes of illustration and not by way of limitation.

EXAMPLES

Example 1

Chemical Synthesis

General Information

Reagents were obtained from commercial sources and used without any further purification. Fmoc-NH-PEG3-COOH was obtained according to the described protocol in A. Soriano, R. Ventura, A. Molero, R. Hoen, V. Casadó, A. Cortés, F. Fanelli, F. Albericio, C. Lluís, R. Franco, et al., *J. Med. Chem.* 2009, 52, 5590-5602.

Solid-phase reactions were performed in polypropylene tubes equipped with polyethylene frits and polypropylene caps using an orbital agitator shaking device. Fmoc-protected Rink Amide AM resin (loading 0.7 mmol/g) was purchased from Iris Biotech. SPOrT resin was prepared as previously described (D. Bonnet, S. Riché, S. Loison, R. Dagher, M. Frantz, L. Boudier, R. Rahmeh, B. Mouillac, J. Haiech, M. Hibert, *Chem.-Eur. J.* 2008, 14, 6247-6254). The completion of couplings and Fmoc cleavages was monitored with the Kaiser test and the TNBS test.

Analytical reverse-phase high performance liquid chromatography (RP-HPLC) was performed on a C18 Sunfire column (5 m, 4.6 mm×150 mm) using a linear gradient (5% to 95% in 20 min, flow rate of 1 mL·min$^{-1}$) of solvent B (0.1% TFA in MeCN, v/v) in solvent A (0.1% TFA in $H_2O$, v/v). Detection was set at 220 and 254 nm. Semi-preparative RP-HPLC chromatography was performed on a SunFire C18 column (5 m, 19×150 mm) using a gradient of solvent B (0.1% TFA in MeCN, v/v) in solvent A (0.1% TFA in $H_2O$, v/v) and a flow-rate of 20 ml·min$^{-1}$. High resolution mass spectra (FIRMS) were obtained on an Agilent Technology 6520 Accurare-Mass Q.T of LC/MS apparatus equipped with a Zorbax SB C18 column (1.8 m, 2.1×50 mm) using electrospray ionization (ESI) and a time-of-flight analyzer (TOF). $^{1}H$ and $^{13}C$ NMR spectra were recorded on a Bruker Advance spectrometer (400 MHz for $^{1}H$ spectra and 126 MHz for $^{13}C$) at 25° C. Chemical shifts are reported in parts per million (ppm) relative to residual solvent and coupling constants (J) are reported in Hertz (Hz). Signals are described as s (singlet), d (doublet), t (triplet), q (quartet), m (multiplet), br s (broad singlet) and br d (broad doublet).

Solid-Phase Synthesis - Scheme 1
Lys(N3)-CBT

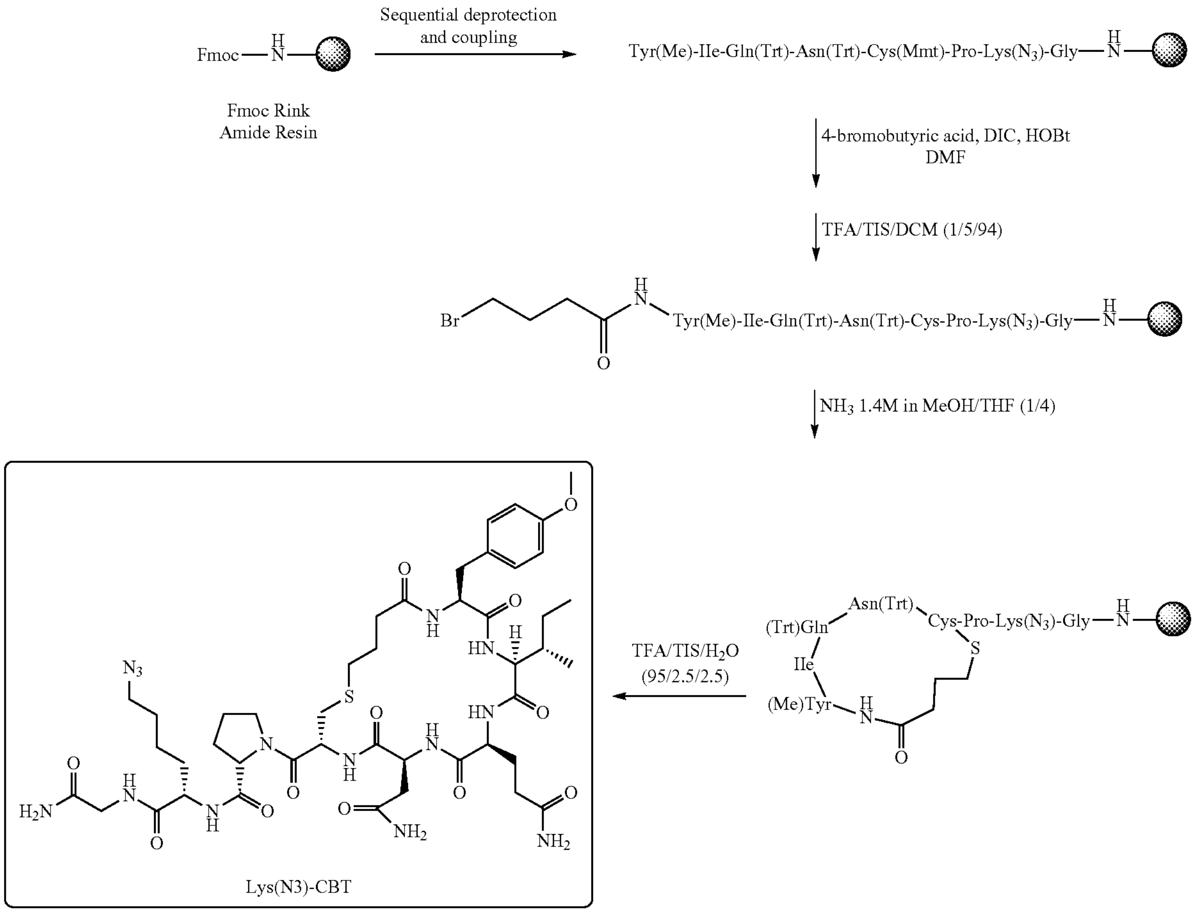

The synthesis was performed on Fmoc Rink Amide AM resin (0.21 mmol, loading 0.7 mmol/g, 300 mg). The cleavage of Fmoc protecting groups was performed in 20% piperidine in DMF (5 mL; 2 times for 15 min). Fmoc-protected amino acids were coupled in DMF (5 mL) for 45 min using HBTU (3.8 equiv.) and HOBt (4 equiv.) with DIEA (12 equiv.) as activating agents, except the introduction of Fmoc-Cys(Mmt)-OH (5 equiv.) which was carried out using HATU (4.9 equiv.) with tetramethylpiperidine (10 equiv.) in DMF (5 mL) for 45 min. 4-Bromobutyric acid (5 equiv.) was introduced using DIC (5 equiv.) and HOBt (5 equiv.) in DMF (5 mL) for 24 hours. To remove the cysteine Mmt protecting group the peptide was treated with TFA/TIS/DCM 1/5/94 (v/v/v; 12 mL; 7 times for 2 min). The removal of Mmt was monitored by analytical RP-HPLC. The intramolecular cyclisation was performed in 1.4 M $NH_3$ in MeOH/THF 1/4 (v/v, 5 mL) for 4 hours at room temperature. The peptide was cleaved from the resin by TFA/$H_2O$/TIS 95/2.5/5.5 (v/v/v; 15 mL) treatment for 3 hours at room temperature. The filtrate was added dropwise to 120 mL of cold $Et_2O$, centrifuged for 5 min at 3000 rpm at 4° C. The solvent was removed, the solid was washed once with cold $Et_2O$, which was then removed by centrifugation for 5 min at 3000 rpm at 4° C. and decantation. The crude peptide was dried and purified by semi-preparative RP-HPLC using a linear gradient (10% to 60% in 30 min) of solvent B in solvent A, affording Lys($N_3$)-CBT (60 mg, 28%) as a white solid. $T_R$=11.04 min (>95% purity [220.8 nm]); HRMS (ESI) calcd for $C_{45}H_{68}N_{14}NaO_{12}S$ ($[M+Na]^+$): 1051.4760; found: 1051.4776.

Dimeric PEG Chain 1

1

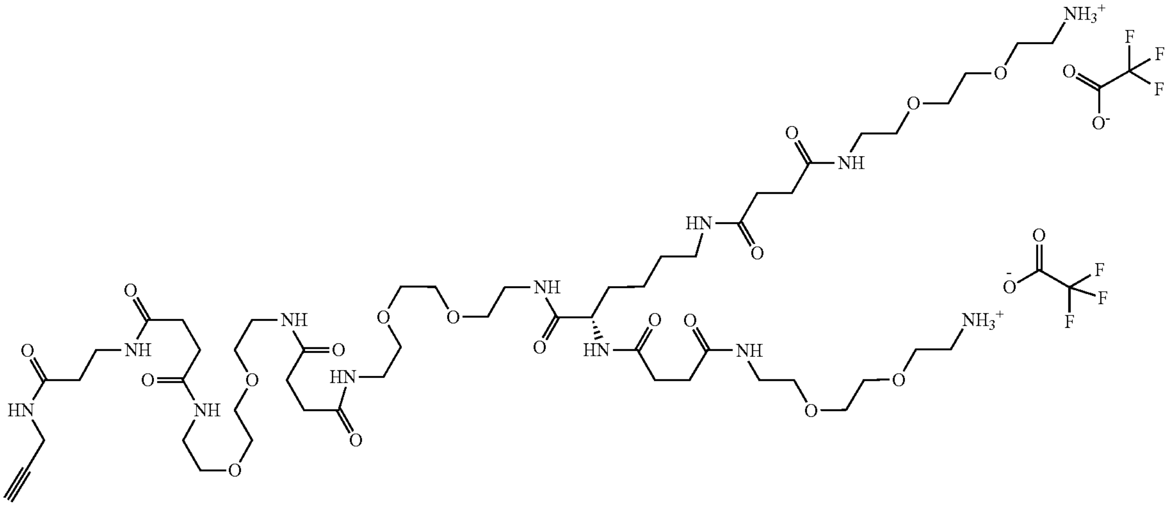

The synthesis was performed on SPOrT resin (0.12 mmol, loading 0.6 mmol/g, 200 mg). The cleavage of Fmoc protecting groups was performed in 20% piperidine in DMF (2 mL; 2 times for 20 min). Fmoc-NH-PEG3-COOH (2 equiv.) was introduced in DMF (2 mL) for 45 min using HBTU (1.9 equiv.) and HOBt (2 equiv.) with DIEA (6 equiv.) as activating agents. Fmoc-Lys(Fmoc)-OH (4 equiv.) was introduced in DMF (2 mL) for 45 min using HBTU (3.8 equiv.), HOBt (4 equiv.) and DIEA (12 equiv.). The dimeric chain was cleaved from the resin by TFA/$H_2O$/TIS 95/2.5/2.5 (v/v/v) treatment for 3 hours at room temperature. The filtrate was precipitated with cold $Et_2O$, centrifuged for 5 min at 3000 rpm at 4° C. and the solvent was removed by decantation. The residue was washed with cold $Et_2O$, centrifuged one more time and the solvent was removed by decantation. The crude peptide was dried and purified by semi-preparative RP-HPLC using a linear gradient (0% to 30% in 40 min) of solvent B in solvent A to obtain the dimeric PEG chain 1 (20 mg, 23%) as a brown oil. $T_R$=5.51 min (>95% purity [220.8 nm]); MS (ESI): calcd for $C_{52}H_{96}N_{12}O_{18}$ ([M+2H]2+/2) 588.35; found 588.35.

Monomeric PEG Chain 3

3

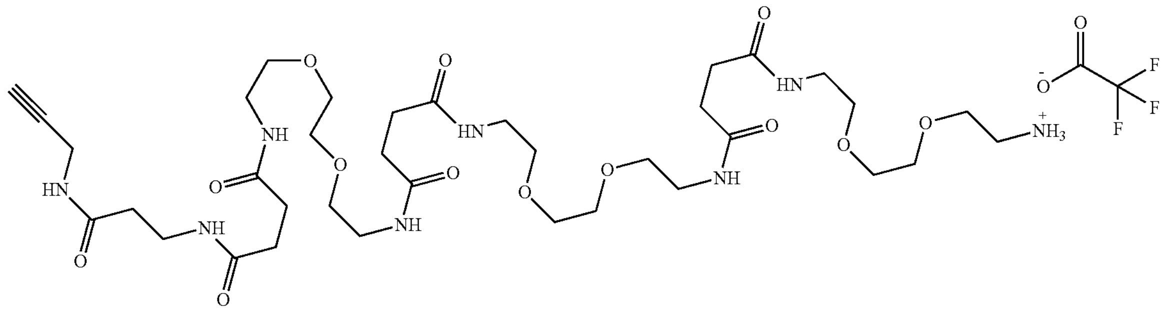

The monomeric chain was synthesized on a SPOrT resin (0.060 mmol, loading 0.6 mmol/g, 100 mg). The cleavage of Fmoc protecting groups was performed in 20% piperidine in DMF (0.5 mL; 2 times for 20 min). Fmoc-NH-PEG3-COOH (2 equiv.) was introduced in DMF (0.5 mL) for 45 min using HBTU (1.9 equiv.) and HOBt (2 equiv.) with DIEA (6 equiv.) as activating agents. The monomeric chain was cleaved from the resin by TFA/$H_2O$/TIS 95/2.5/2.5 (v/v/v) treatment for 3 hours at room temperature. The filtrate was precipitated with cold $Et_2O$, centrifuged for 5 min at 3000 rpm at 4° C. and the solvent was removed by decantation. The residue was washed with cold $Et_2O$, centrifuged one more time and the solvent was removed by decantation. The crude peptide was dried and purified by semi-preparative RP-HPLC using a linear gradient (0% to 30% in 40 min) of solvent B in solvent A, to obtained the monomeric PEG chain 3 (13.3 mg, 24%) as a brown oil. $T_R$=5.48 min (>95% purity [220.8 nm]); MS (ESI): calcd for $C_{36}H_{66}N_8O_{13}$ ([M+2H]2+/2) 409.24; found 409.24.

Solution-Phase Synthesis - Scheme 2

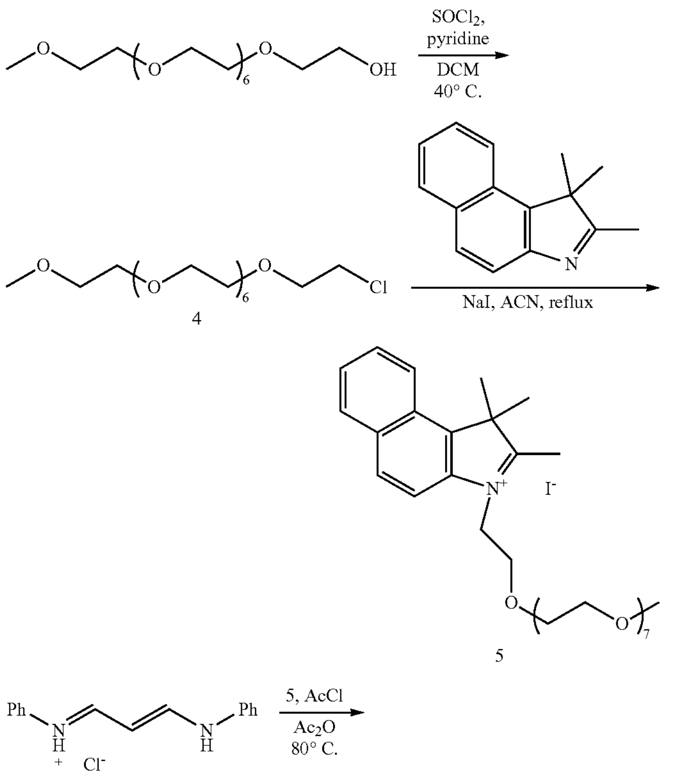

-continued

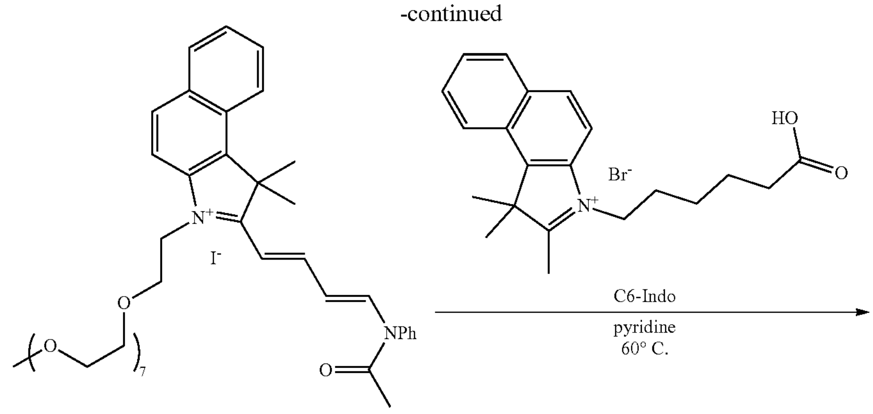

6

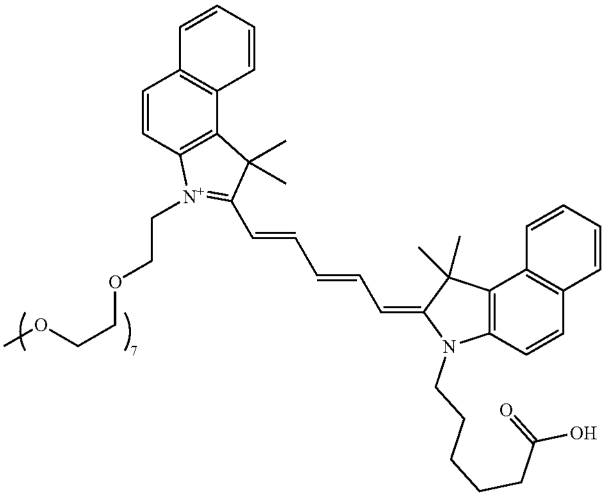

2

25-chloro-2,5,8,11,14,17,20,23-octaoxapentacosane 4

4

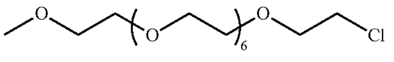

Octaethylene glycol monomethyl ether (3.58 g, 9.32 mmol) was dissolved in DCM (20 mL) and pyridine (1.5 mL). To this solution was added thionyl chloride (1 mL) the solution was allowed to stir at 40° C. overnight. The product was extracted with DCM and the organic phase was washed with HCl (1 M) then neutralised with a saturated solution of $NaHCO_3$ before being dried over anhydrous $MgSO_4$. The solution was filtered and evaporated to give 3.10 g of a yellowish oil (Yield=83%). The TLC showed that the product was pure (Rf=0.74, DCM/MeOH, 9/1). The product was used for the next step with no further purification.

1,1,2-trimethyl-3-(2,5,8,11,14,17,20,23-octaoxapentacosan-25-yl)-1H-benzo[e]indol-3-ium iodide 5

5

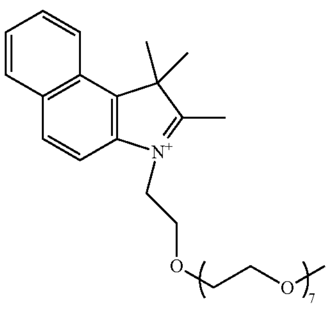

To a solution of 4 (3.00 g, 7.46 mmol) in I (20 mL) was added trimethyl-1H-benzo[e]indole (2.00, 9.57 mmol, 1.3 eq) followed by sodium iodide (5.00, 33.55 mmol, 4.5 eq). The solution was allowed to stir at 120° C. overnight. The deep night blue solution was evaporated and the product was extracted with DCM and the organic phase was washed with water three times before being dried over anhydrous $MgSO_4$. The solution was filtered and evaporated and the product was solubilized in a minimum of acetone and was poured in ether. The precipitation step was repeated until the TLC indicated that the product was pure. Rf=0.37 (DCM/MeOH, 96/4). 2.17 g of 5 were obtained as a blue oil (Yield=41%). $^1H$-NMR (400 MHz, $CDCl_3$): δ 8.10-8.01 (m, 4H, H Ar), 7.73 (t, J=7.6 Hz, 1H, H Ar), 7.65 (t, J=7.6 Hz, 1H, H Ar), 5.13 (t, J=4.9 Hz, 2H, $CH_2N^+$), 4.10 (t, J=4.9 Hz, 2H, $CH_2$ PEG), 3.64-3.53 (m, 22H, $CH_2$ PEG), 3.46 (m, 6H, $CH_2$ PEG), 3.36 (s, 3H, Ome PEG), 3.14 (s, 3H, $CH_3$ indolenine), 1.86 (s, 6H, 3 $CH_3$). $^{13}C$-NMR (101 MHz, $CDCl_3$): δ 197.7 ($CN^+$), 138.2 (C Ar), 136.7 (C Ar), 133.6 (C Ar), 131.3 (C Ar), 130.0 (C Ar), 128.4 (C Ar), 127.7 (C Ar), 127.4 (C Ar), 122.7 (C Ar), 113.2 (C Ar), 71.9, 70.5, 70.5, 70.5, 70.5, 70.4, 70.4, 70.3, 70.2, 70.2, 67.3, 58.9, 55.9, 50.5, 30.9, 22.5, 16.5. HRMS ($ESI^+$), calcd for $C_{32}H_{50}NO_8^+$ [M+]576.3531, found 576.3524.

1,1-dimethyl-3-(2,5,8,11,14,17,20,23-octaoxapentacosan-25-yl)-2-((E,3E)-4-(N-phenylacetamido)buta-1, 3-dien-1-yl)-1H-benzo[e]indol-3-ium iodide 6

6

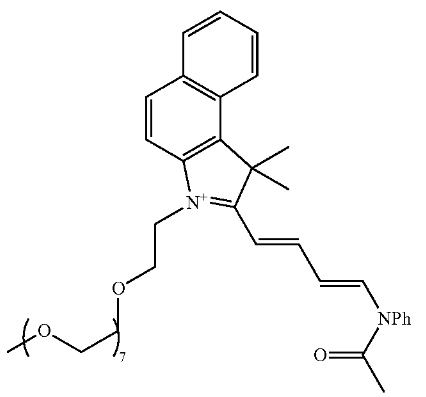

To a solution of 5 (1.00 g, 1.42 mmol) and malonaldehyde dianilide hydrochloride (0.40 g, 1.55 mmol, 1.1 eq) in acetic anhydride (10 mL) was added 1 mL of acyl chloride. The solution was allowed to stir at 100° C. before being evaporated. The crude was purified by column chromatography on silica gel (DCM/MeOH, 9/1) to obtain 1.00 g of 6 as a dark syrup (Yield=80%). Rf=0.62 (DCM/MeOH, 9/1). The product was involved in the next step without further characterization.

2-((1E,3E,5E)-5-(3-(5-carboxypentyl)-1,1-dimethyl-1,3-dihydro-2H-benzo[e]indol-2-ylidene)penta-1,3-dien-1-yl)-1,1-dimethyl-3-(2,5,8,11,14,17,20,23-octaoxapentacosan-25-yl)-1H-benzo[e]indol-3-ium iodide 2

2

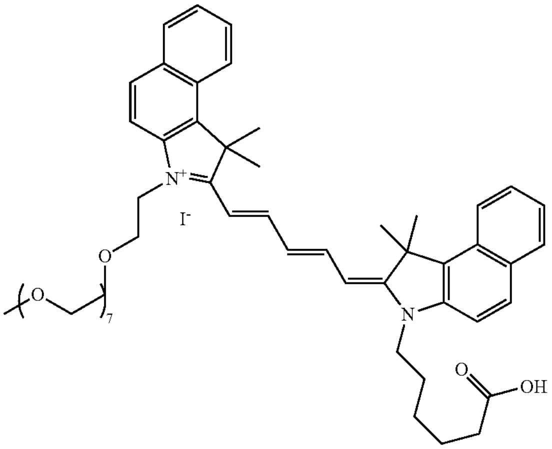

6 (1.00 g, 1.14 mmol) and $C_6$-Indo (K. Kiyose, K. Hanaoka, D. Oushiki, T. Nakamura, M. Kajimura, M. Suematsu, H. Nishimatsu, T. Yamane, T. Terai, Y. Hirata, et al., *J. Am. Chem. Soc.* 2010, 132, 15846-15848) (500 mg, 1.23 mmol, 1.1 eq) were dissolved in pyridine (15 mL) and the solution was allowed to stir at 60° C. for 1 h. The solvents were evaporated and the product was extracted with DCM and the organic phase was washed with HCl (1 M) before being dried over anhydrous $MgSO_4$. The solution was filtered and the crude was purified by column chromatography on silica gel (DCM/MeOH, 99/1 to 85/15) to obtain 490 mg of 2 as a dark blue syrup (Yield=40%). Rf=0.57 (DCM/MeOH, 9/1). $^1H$-NMR (400 MHz, $CDCl_3$): δ 8.42-8.33 (m, 2H, H Ar), 8.19-8.17 (m, 2H, H Ar), 7.95-7.89 (m, 4H, H Ar), 7.60 (dd, J=9.9, 5.4 Hz, 2H, H Ar), 7.48 (dt, J=16.8, 8.4 Hz, 3H, H Ar), 7.39-7.37 (m, 1H, H Ar), 6.96-6.90 (m, 1H, H Ar), 6.55-6.52 (m, 1H, H Ar), 6.33 (d, J=13.6 Hz, 1H, H Ar), 4.51-4.48 (m, 2H, $CH_2$), 4.20-4.16 (m, 2H, $CH_2$), 4.01-3.99 (m, 2H, $CH_2$), 3.65-3.51 (m, 32H, $CH_2$ PEG), 3.37 (s, 3H, Ome PEG), 2.45-2.42 (m, 2H, $CH_2$), 2.10 (s, 12H, 4 $CH_3$), 1.92-1.87 (m, 2H, $CH_2$), 1.78-1.74 (m, 2H, $CH_2$), 1.62-1.58 (m, 2H, $CH_2$). $^{13}C$-NMR (126 MHz, $CDCl_3$): δ 174.8 (CN), 174.1 (CN), 152.8 (CO), 140.0 (C Ar), 139.2 (C Ar), 134.0 (C Ar), 133.7 (C Ar), 131.7 (C Ar), 131.7 (C Ar), 130.5 (C Ar), 130.1 (C Ar), 129.9 (C Ar), 129.9 (C Ar), 128.2 (C Ar), 128.0 (C Ar), 127.7 (C Ar), 127.5 (C Ar), 126.5 (C Ar), 126.5 (C Ar), 125.0 (C Ar), 124.9 (C Ar), 122.3 (C Ar), 111.5 (C Ar), 110.4 (C Ar), 104.0 (C Ar), 103.2 (C Ar), 71.7, 71.0, 70.4, 70.3, 70.3, 70.3, 70.3, 70.3, 70.3, 70.2, 68.3, 59.0, 51.2, 51.2, 51.2, 45.0, 45.0, 45.0, 44.3, 33.9, 27.8 (2 $CH_3$), 27.8 (2 $CH_3$), 27.1 ($CH_2$), 26.2 ($CH_2$), 24.3 ($CH_2$), 24.3 ($CH_2$), 24.3 ($CH_2$). HRMS (ESI) calcd for $C_{56}H_{75}N_2O_{10}$ ($[M-I^-]^+$): 935.5422; found: 935.5393.

dCy5.5-PEG (Compound (2), According to the Invention, without a Ligand)

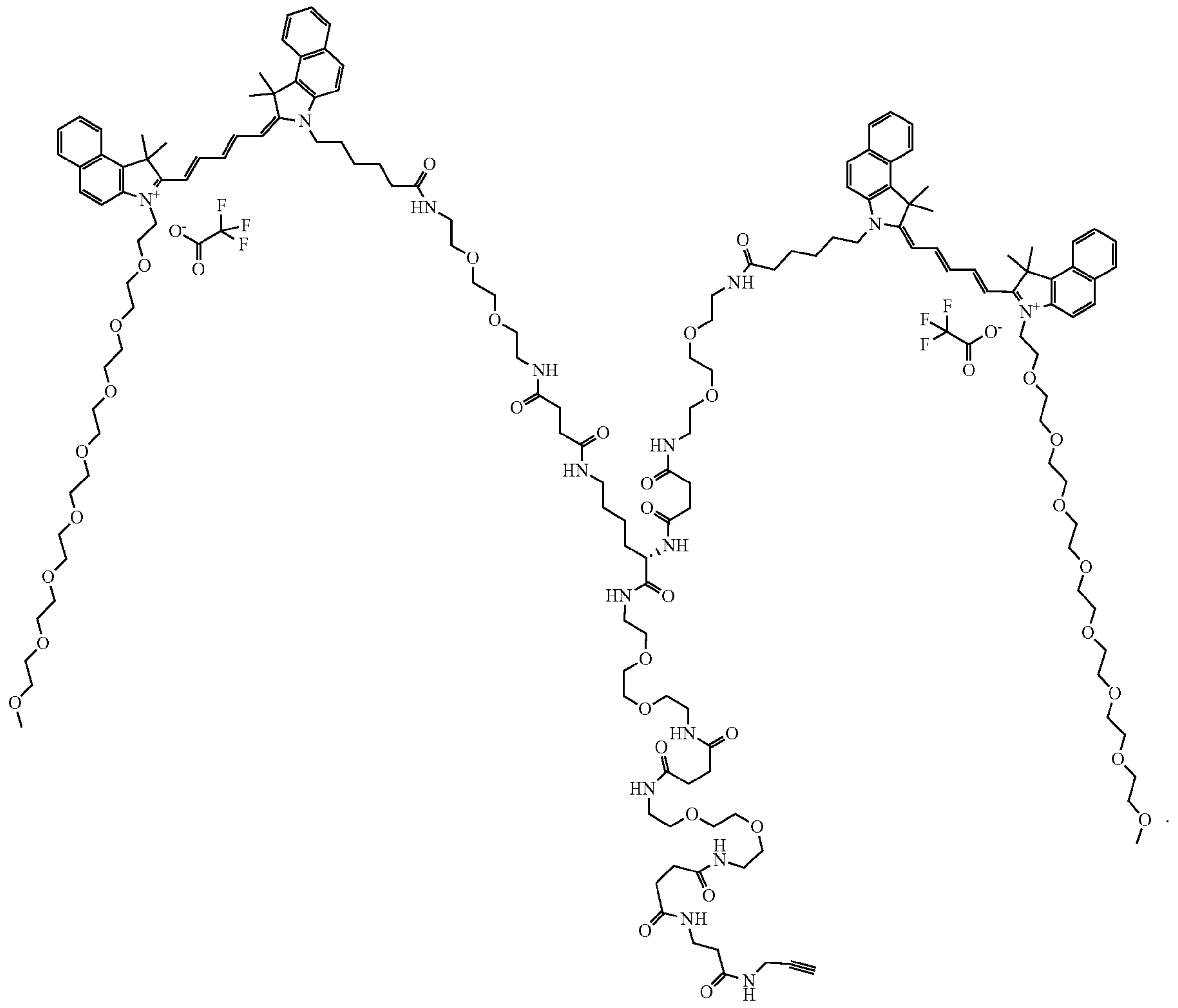

dCy5.5-PEG

Pegylated cyanine 2 (1.9 equiv., 13 mg, 0.012 mmol) and the dimeric PEG chain 1 (1 equiv., 9 mg, 0.006 mmol) were solubilized in 262 μL of dry DMF. PyBOP (2 equiv., 6.66 mg, 0.012 mmol) and DIEA (6 equiv., 6.36 μL, 0.0385 mmol) were added to the mixture. The reaction mixture was stirred for 1 hour at room temperature. The crude product was purified by semi-preparative RP-HPLC using a linear gradient (15% to 60% in 30 min) of solvent B in solvent A, to obtain dCy5.5-PEG (16 mg, 77%) as a blue solid. $T_R$=14.71 min (>95% purity [220.8 nm]); MS (ESI). calcd for $C_{164}H_{241}N_{16}O_{36}$ ($[M+H]^{3+}/3$) 1003.58; found 1003.58.

mCy5.5-PEG (not According to the Invention)

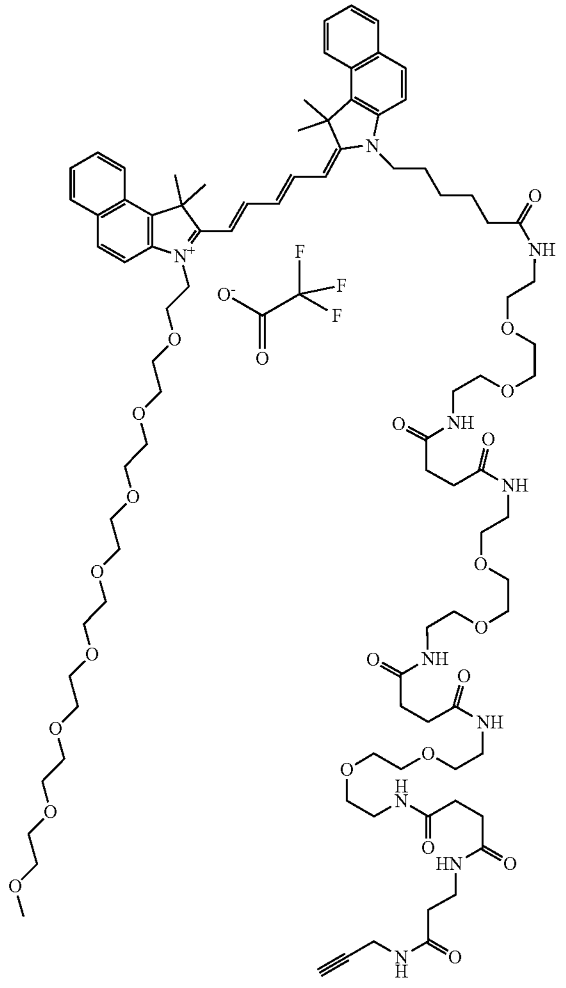

mCy5.5-PEG

Pegylated cyanine 2 (1.2 equiv., 9.59 mg, 0.009 mmol) and the monomeric PEG chain 3 (1 equiv., 7 mg, 0.008 mmol) were solubilized in 308 μL of dry DMF. PyBOP (1.2 equiv., 4.7 mg, 0.009 mmol) and DIEA (6 equiv., 7.46 μL, 0.045 mmol) were added and the reaction mixture was stirred for 1 hour at room temperature. The crude product was purified by semi-preparative RP-HPLC using a linear gradient (15% to 60% in 30 min) of solvent B in solvent A, to obtain the desired product (8.1 mg, 58%) as a blue solid. $T_R$=13.15 min (>95% purity [220.8 nm]); MS (ESI): calcd for $C_{92}H_{138}N_{10}O_{22}$ ([M+H]2+/2) 867.50; found 867.50.

dCy5.5-PEG-CBT (Compound (3), According to the Invention, with a Ligand: CBT)

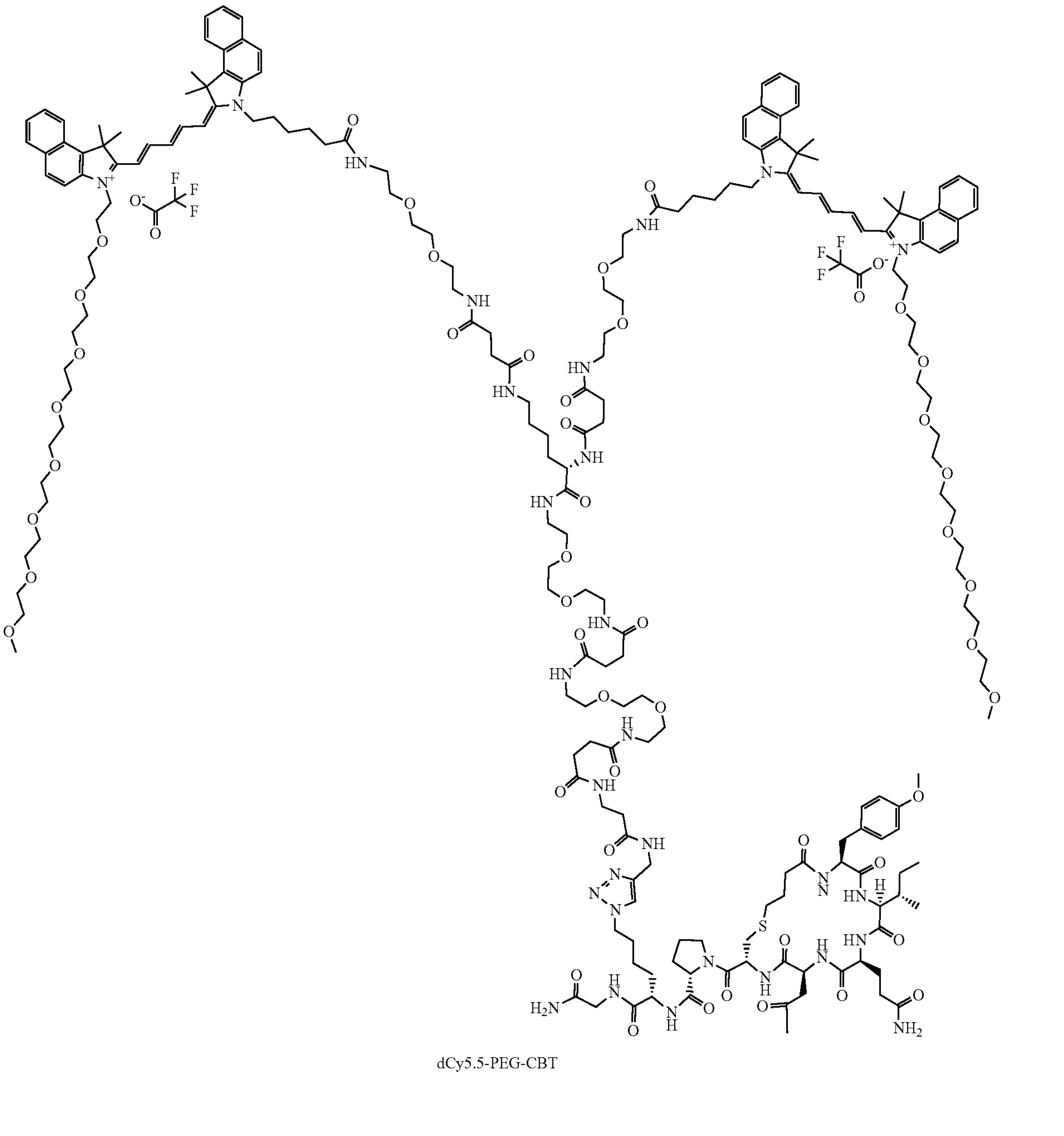

dCy5.5-PEG-CBT $CuSO_4$ (1 equiv., 2.04 μmol, 20.4 μL of 0.1 M aqueous solution), sodium ascorbate (1.2 equiv., 2.44 μmol, 24.4 μL of 0.1 M aqueous solution) and TBTA (1.2 equiv., 2.44 μmol, 24.4 μL of 0.1 M DMF solution) were pre-activated during 20 min at room temperature in a total volume of water/DMF 2/8 (v/v) of 70 μL. Lys($N_3$)-CBT (1.2 equiv., 2.44 μmol, 2.52 mg) and dCy5.5-PEG (1 equiv., 2.04 μmol, 6.6 mg) were added to the mixture followed by 700 μL of water/DMF 2/8 (v/v). The reaction mixture was stirred for 3 hours at 37° C. The crude product was purified by semi-preparative RP-HPLC using a linear gradient (200% to 70% in 30 min) of solvent B in solvent A, to obtain the desired product (3.5 mg, 40%) as a blue solid. $T_R$=14.2 min (>95% purity [220.8 nm]); FIRMS (ESI) calcd for $C_{209}H_{309}N_{30}O_{48}S$ ($[M+H]^3$+/3): 1346,4127; found: 1346.4097.

mCy5.5-PEG-CBT (not According to the Invention)

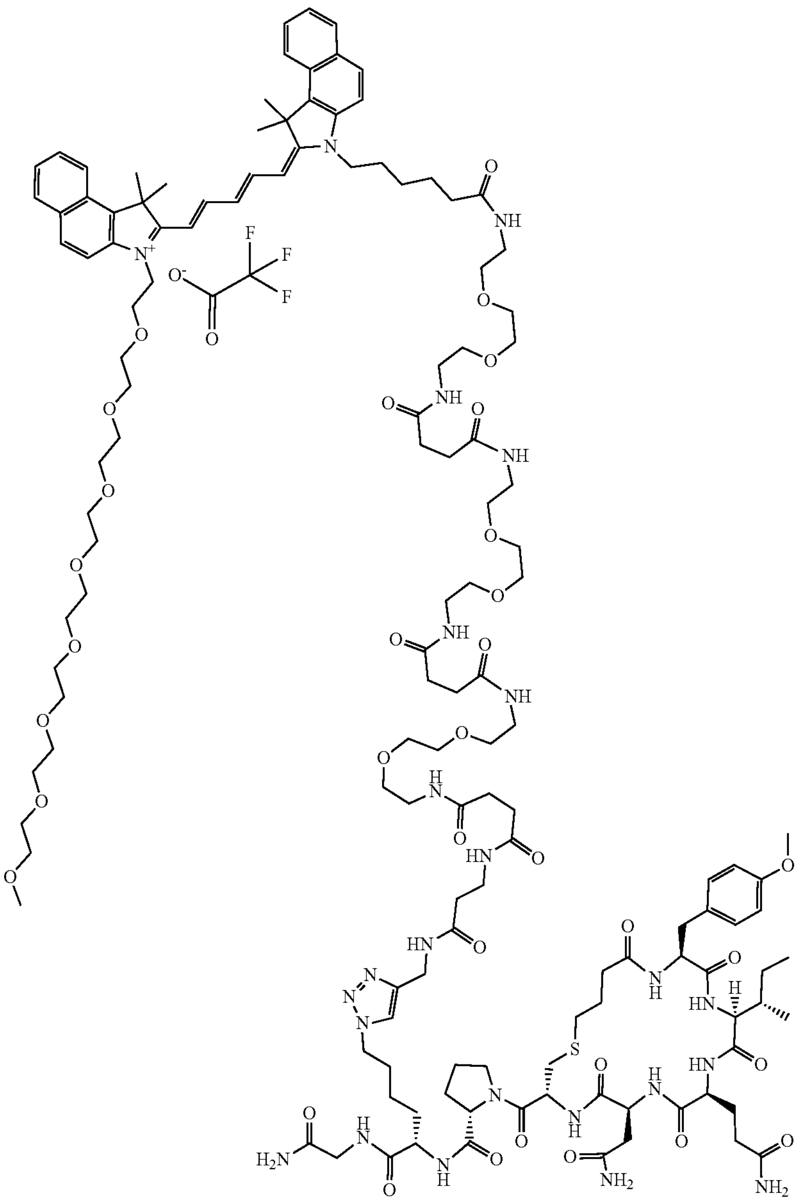

mCy5.5-PEG-CBT $CuSO_4$ (1 equiv., 3.25 mol, 32.5 μL of 0.1 M aqueous solution), sodium ascorbate (1.2 equiv., 3.9 μmol, 39 μL of 0.1 M aqueous solution) and TBTA (1.2 equiv., 3.9 μmol, 39 μL of 0.1 M DMF solution) were pre-activated during 20 min at room temperature in a total volume of water/DMF 2/8 (v/v) of 100 μL. Lys($N_3$)-CBT (1.2 equiv., 3.9 μmol, 4.01 mg) and mCy5.5-PEG (1 eq., 3.25 μmol, 6 mg) were added to the mixture followed by 1100 μL of water/DMF 2/8 (v/v). The reaction mixture was stirred for 3 hours at 37° C. The crude product was purified by semi-preparative RP-HPLC using a linear gradient (20% to 70% in 40 min) of solvent B in solvent A, to obtain the desired product (4.1 mg, 44%) as a blue solid. $T_R$=12.8 min (>95% purity [220.8 nm]); HRMS (ESI) calcd for $C_{137}H_{207}N_{24}O_{34}S$ ($[M+2H]^3$+/3): 921,4978; found: 921.4959.

Compounds (2) and (3) of the invention can also be prepared in solution as detailed below for compounds (4), (5), (6) and (7).

Absorption and Fluorescence Spectroscopy

General Information

Absorption spectra were recorded on a Cary 4000 spectrophotometer (Varian) and fluorescence spectra on a Fluoromax 3 (Jobin Yvon, Horiba) spectrofluorometer. Fluorescence emission spectra were systematically recorded at 630 nm excitation wavelength at 20° C. All fluorescence spectra were corrected for instrumental effects. Fluorescence quantum yields (QY) were measured using Rhodamine 800 in EtOH as a reference (QY=25%).

To characterize the fluorogenicity resulting from the dimerization of the NIR cyanine, the absorption and fluorescence properties of the dimer dCy5.5-PEG and the monomer mCy5.5-PEG were evaluated in solvents of different polarities. Both the dimer and the monomer were highly fluorescent in organic solvents, with fluorescence quantum yields (QY) ranging from 26 to 59% (Table 1) and the fluorescence maxima situating around 710 nm. However, in contrast to the monomer mCy5.5-PEG which was fluorescent in water (QY=22%), the fluorescence in aqueous medium of the dimer dCy5.5-PEG was almost negligible (QY=0.4%).

TABLE 1

Photophysical properties of mCy5.5-PEG and dCy5.5-PEG.

| | mCy5.5-PEG | | | dCy5.5-PEG | | |
|---|---|---|---|---|---|---|
| Solvent | $\lambda_{abs}$ nm[a] | $\lambda_{em}$ nm[b] | QY[c] | $\lambda_{abs}$ nm[a] | $\lambda_{em}$ nm[b] | QY[c] |
| 1,4-Dioxane | 689 | 712 | 59 | 689 | 718 | 28 |
| DMF | 686 | 709 | 50 | 685 | 709 | 56 |
| EtOH | 686 | 709 | 34 | 686 | 710 | 26 |
| MeOH | 681 | 705 | 32 | 682 | 705 | 26 |
| Water | 679 | 700 | 22 | 629 | 700 | 0.4 |

[a]Position of the absorption maximum.
[b]Position of the emission maximum.
[c]Fluorescence quantum yield.

To confirm the formation of the intramolecular dimer, the absorption spectra of two dyes were compared. The monomer presented similar absorption spectra in water and in MeOH with the absorption maxima around 680 nm. Although the absorption spectrum of the dimer in MeOH was identical to that of the monomer having the maximum at 682 nm, its absorption spectrum in water presented a blue-shifted maximum at 629 nm and a long-wavelength shoulder. This new band can be assigned to the non-fluorescent intramolecular dimer of the H-aggregate type, which is highly favored in aqueous medium. Indeed, the intramolecular H-aggregate in dCy5.5-PEG quickly disappeared upon the addition of MeOH to water, which resulted in the shift of the absorption maximum to 682 nm and the recovery of the fluorescence. As a consequence, dCy5.5-PEG presented excellent fluorogenic properties, with up to 140-fold higher QY in organic solvents than in water. For comparison, the monomer mCy5.5-PEG is characterized by only <2.7-fold difference in QY between water and organic solvents. As the absorption spectrum of dCy5.5-PEG in the open form (in MeOH) is the same as that of the cyanine 2, the extinction coefficient of the dimer should be ca double of the monomer. The extinction coefficient for the cyanine 2, was measured to be 222 000 $M^{-1}$ $cm^{-1}$ in MeOH, which allows estimation of the extinction coefficient for the dimer dCy5.5-PEG: 222 000 $M^{-1}$ $cm^{-1}\times2=444$ 000 $M^{-1}$ $cm^{-1}$. Then, given its strong QY (56% in DMF), dCy5.5-PEG appears to be one of the brightest fluorogenic NIR dyes reported to date.

Fluorescence Confocal Microscopy

Cell Lines, Culture Conditions and Treatment

HEK293 cells expressing the GFP-fused oxytocin receptor (GFP-OTR) and wild-type HEK293 cells were cultured in Eagle's minimal essential medium (MEM, Invitrogen 21090) with 10% of heat-inactivated fetal bovine serum, 100 U/mL of penicillin, 100 g/mL of streptomycin, 2 mM of glutamine and 50 g/mL of hygromycin B for GFP-OTR cells at 37° C. in a humidified 5% $CO_2$ atmosphere. 70-80% cell confluence was maintained by removal of a portion of the culture and replacement with fresh medium twice a week. For confocal microscopy studies, cells were seeded onto 35 mm ibiTreat Ibidi Polymer Coverslip at a density of 100 000 cells/Ibidi 24 h before microscopy.

Confocal Microscopy Experiments

Cells were washed two times by gentle rinsing with Hank's Balanced Salt Solution (HBSS, no phenol red), then solutions of fluorescent ligands at 10 nM in HBSS (1 mL) were added and the cells were incubated for 5 min at room temperature. For competition experiments, a mixture of 10 nM of fluorescent ligands and 2 μM of carbetocin was used. Fluorescence confocal microscopy experiments were performed on a Leica TCS SPE-II microscope with a HXC PL APO 63×/1.40 OIL CS objective. GFP excitation was performed with a 488 nm 10 mW laser, the excitation of Cy5.5 was performed with a 635 nm 18 mW laser. Image treatment was proceeded using ImageJ (Wayne Rasband, National Institute of Mental Health, Bethesda).

Results

As shown in FIG. 1, the addition of as few as 10 nM solution of dCy5.5-PEG-CBT revealed the OTR at the cell membrane. The competition experiment performed in the presence of a large excess of the unlabeled CBT ligand did not reveal any fluorescence membrane staining, demonstrating the absence of non-specific interactions of dCy5.5-PEG-CBT with cell membranes and its specific binding to the OTR. To highlight the advantage of using fluorogenic dyes in biological sensing, the OTR imaging was performed either in the presence of fluorogenic dCy5.5-PEG-CBT or non-fluorogenic mCy5.5-PEG-CBT at 500 nM concentration in no wash conditions. Thereby, the excess of unbound non-fluorogenic mCy5.5-PEG-CBT was highly fluorescent in aqueous solution, creating a strong background (FIG. 3). In sharp contrast, the background of the image with dCy5.5-PEG-CBT remained completely dark, probably because in solution the dimeric probe existed in the form of the non-fluorescent H-aggregate.

Small Animal Fluorescence Imaging

Animals

Twelve-week-old pregnant female Swiss mice were purchased from Janvier Laboratories (France). Animals were maintained under controlled environmental conditions (20±2° C.) with a relative humidity (50±10%) and a 12 hour light/dark cycle in Individually ventilated cages (GM500, Techniplast) with bedding made from spruce wood chips (Safe, villeAugy, France) and enriched with nestlets. Food (autoclavable diet, D04, Safe, France) and tap water were available ad libitum. Animal experimentation was conducted with the approval of the French ministry of agriculture and the Ethics local committee for animal experimentation of the Strasbourg University (CREMEAS) under the authorization number #11974-2017103010101372.

In Vivo Fluorescence Biodistribution Study

Animal fluorescence imaging was performed using a luminograph (NightOwl, Berthold Technologies). Lactating mice 11 days after delivery were anesthetized intraperitoneally (Ketamine 150 mg/kg, xylazine 10 mg/kg). Fluorescent compounds (100 μL containing 7.5 nmol in 0.9% NaCl) with or without non-fluorescent carbetocin (100 μL containing 450 nmol in 0.9% NaCl) were administered intravenously (tail vein). Mice were placed in the luminograph (30 min after intravenous administration of the probes), and positioned in decubitus dorsal. Mice were imaged using a halogen lamp (75 W, 340-750 nm) and emission of the dyes was recorded using a 630/700 nm filter. The experiments were repeated on three mice.

Results

Figure 2:
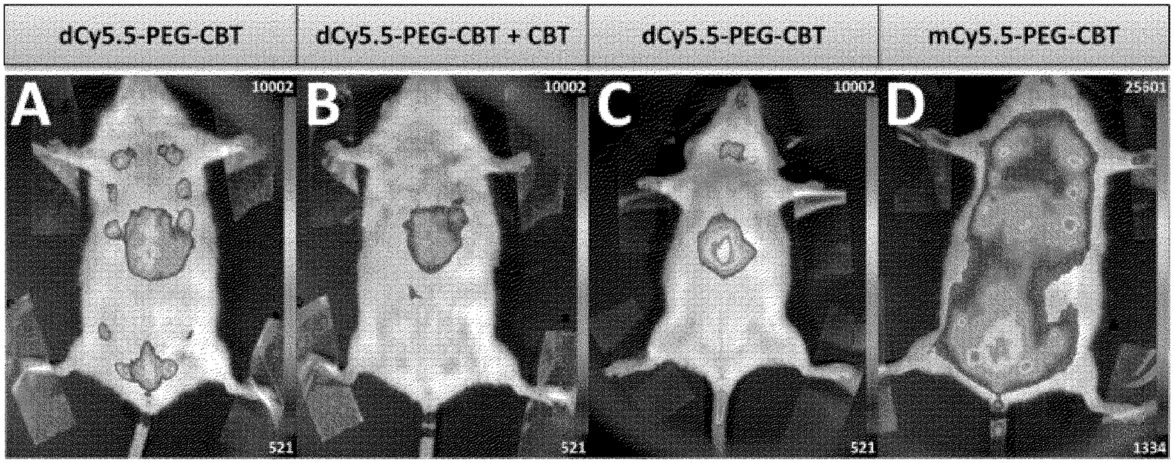
FIG. 2: In vivo images of lactating (A, B, D) or naive (C) mice injected i.v. with 7.5 nmol of dCy5.5-PEG-CBT (A and C), 7.5 nmol of dCy5.5-PEG-CBT and 450 nmol of CBT (B) or 7.5 nmol of mCy5.5-PEG-CBT (D) 30 min prior to the imaging. Representative images of at least 3 biological replicates.

As shown in FIG. 2A, strong fluorescence in mammary glands was detected, with practically negligible off-target signal, except for liver, the organ expected to accumulated the injected dyes. To demonstrate the specific labelling of OTR, dCy5.5-PEG-CBT was injected in the presence of a 60-fold excess of non-fluorescent CBT (FIG. 2B). In that case, only the liver of mice was fluorescent, leaving the mammary glands non-labelled. The absence of mammary gland labelling was also observed in naïve mice (FIG. 2C), which is not expected to overexpress oxytocin GPCR in the glands region. Finally, the administration of the monomeric probe mCy5.5-PEG-CBT resulted in a strong off-target fluorescence, which can be seen in the image (FIG. 2D) using the equivalent intensity scale (maximum value is 20-fold larger than the minimum value).

These results highlight the advantage of using a fluorogenic dimer probe according to the invention to increase the signal-to-noise ratio for the in vivo imaging.

In conclusion, the fluorogenic dimers concept presenting environment-sensitive folding allows to bright fluorogenic NIR probe giving rise to specific, background-free and unprecedented imaging of endogenous OTR in living mice. These results open up fascinating perspectives of non-invasive and non-ionizing fluorescence cartography of GPCRs in living animals.

Example 2

Chemical Synthesis 4 compounds were prepared as detailed below: compounds 4 and 5 (Cy5.5 dimers, formulas are as detailed above) and compounds A and B (DY647 dimers) which have the following formula:

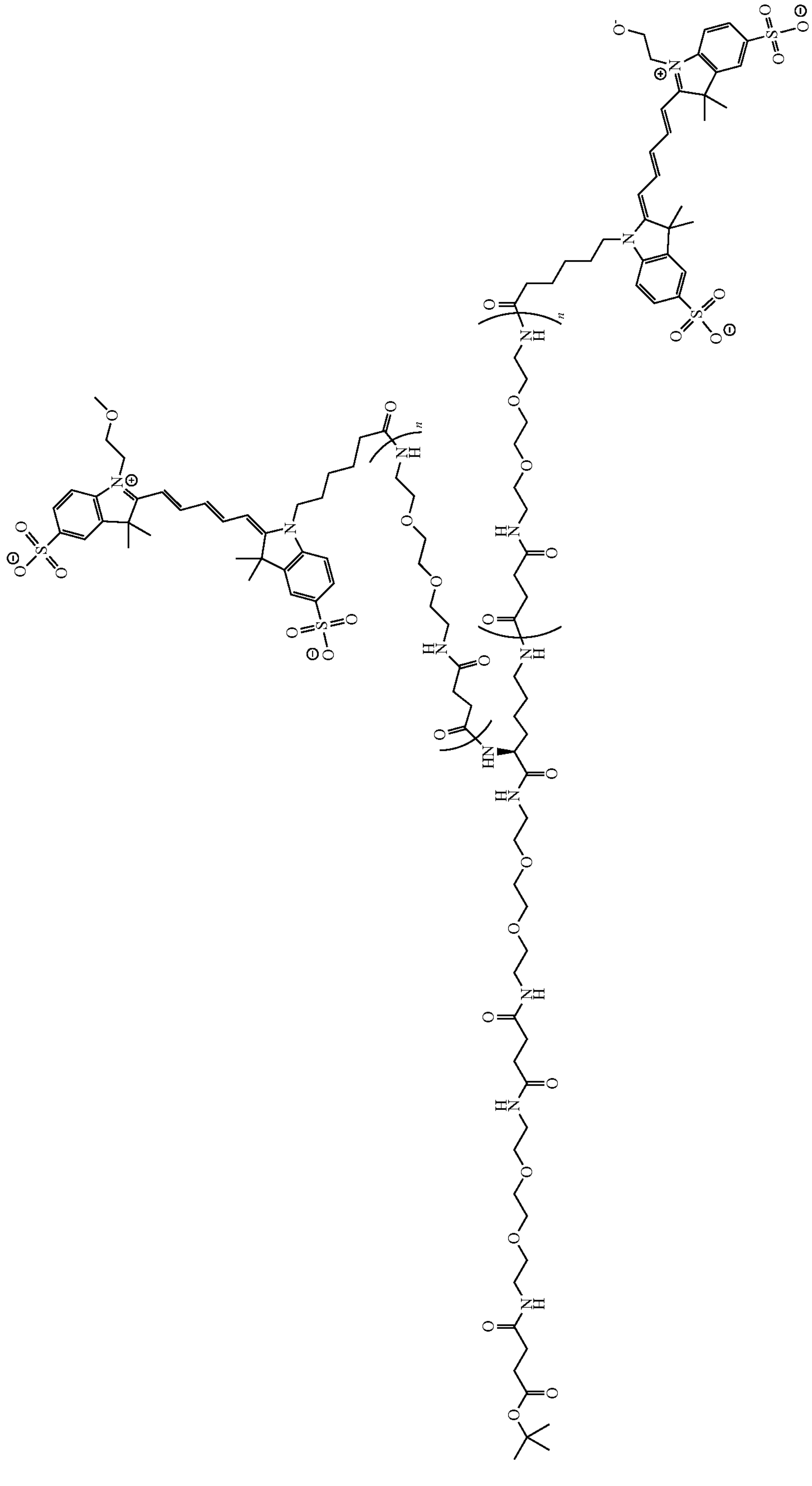

wherein n is 0 (compound A) and 1 (compound B).

Compounds A and B are not in the scope of the invention since they do not have cyanine derivatives (DY647 dimers, comparative examples).

Scheme 3 Syntheiss of dimeric chains in solution.
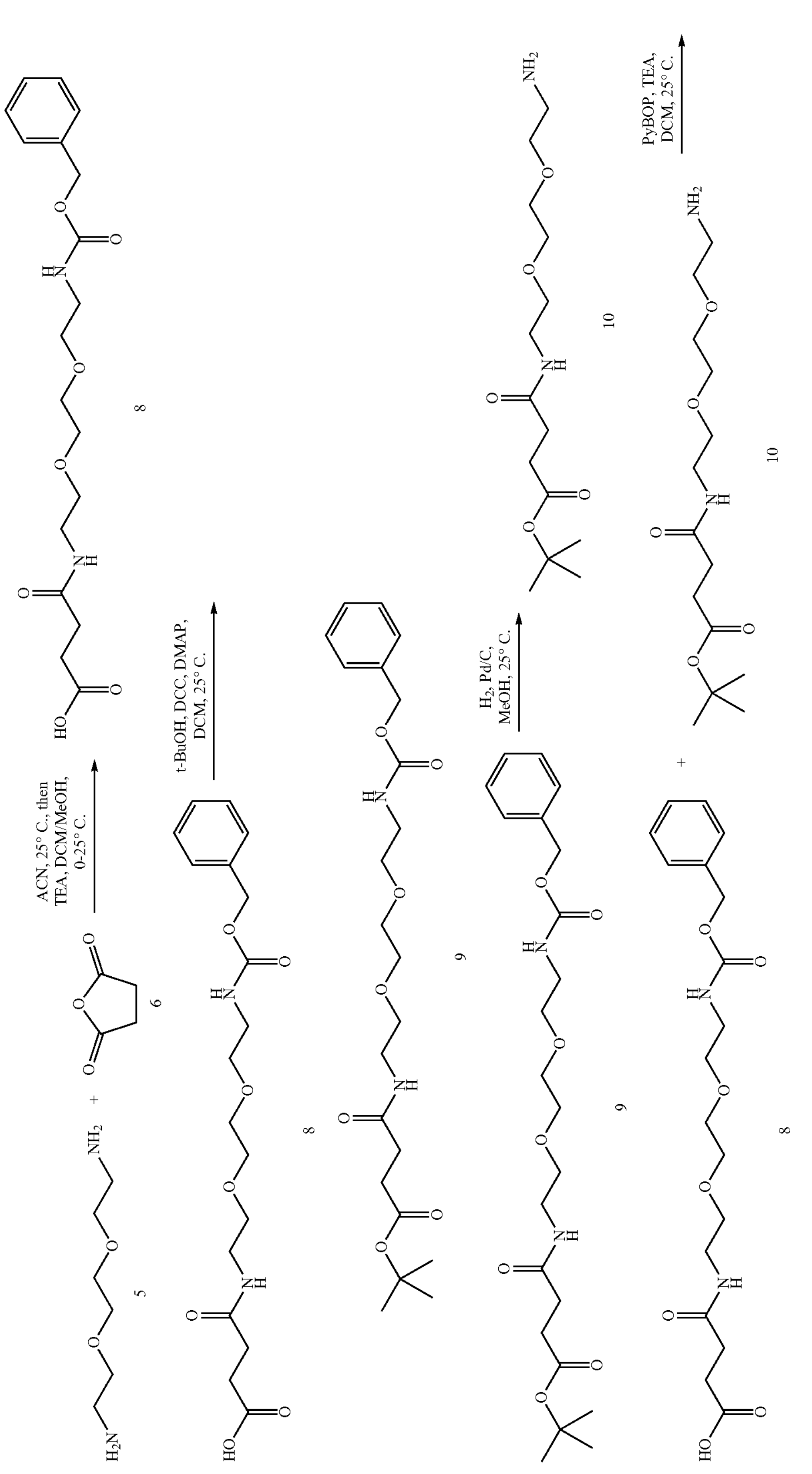
5 + 6 → 8
8 → 9
9 → 10
9 + 8 → 10

-continued
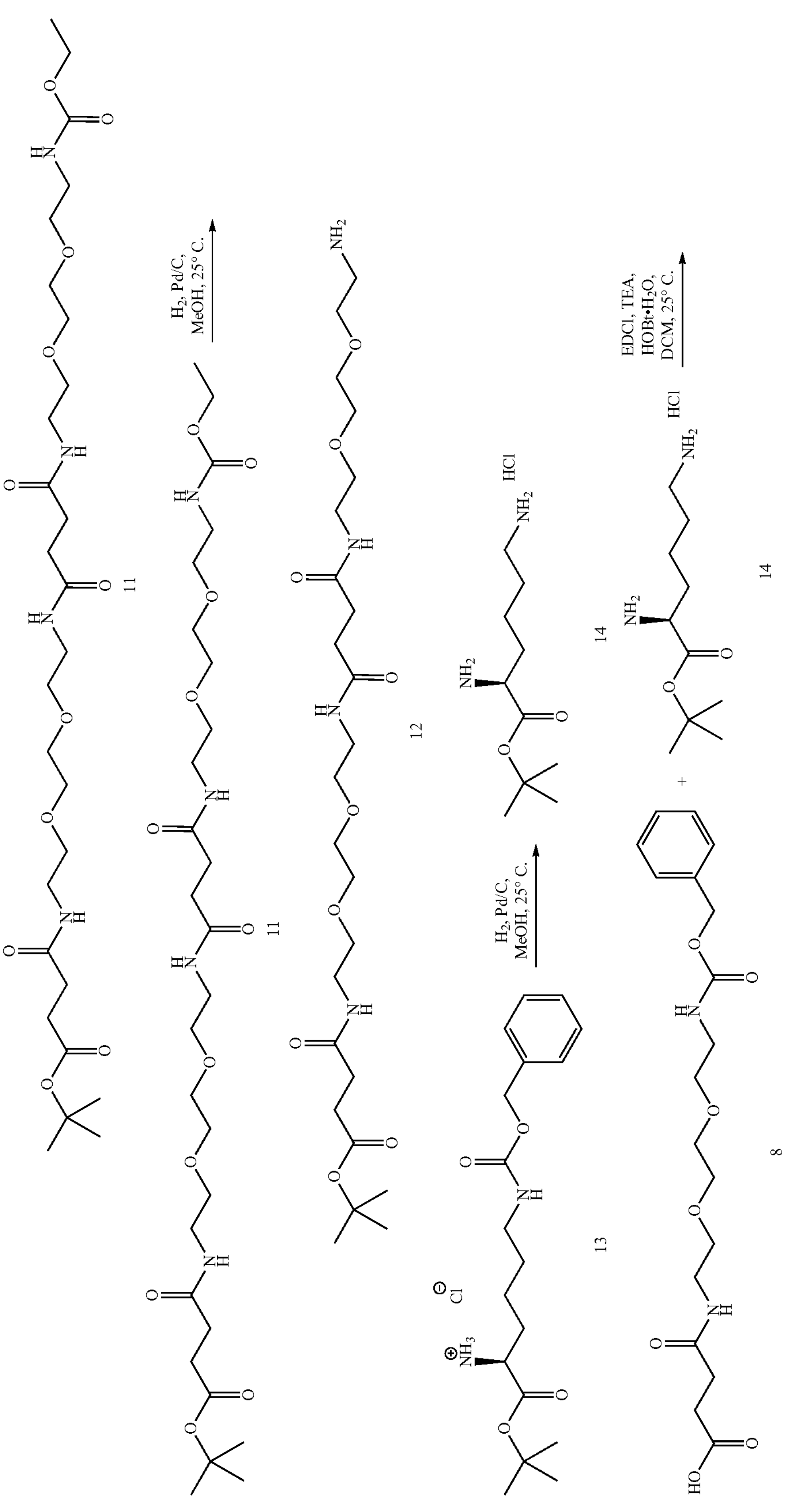
11
11
12
13
14
8
14

-continued
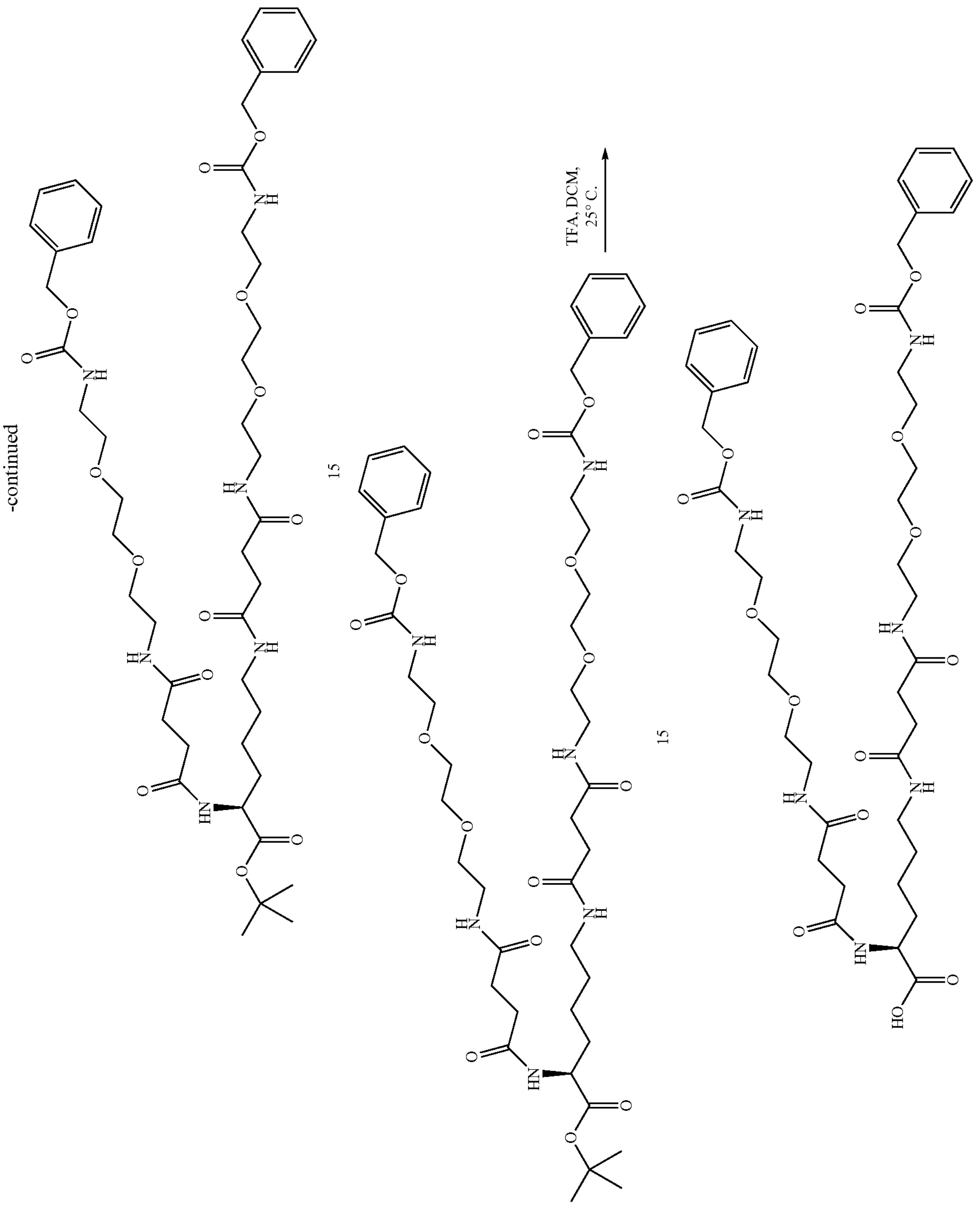
15
15
16

-continued
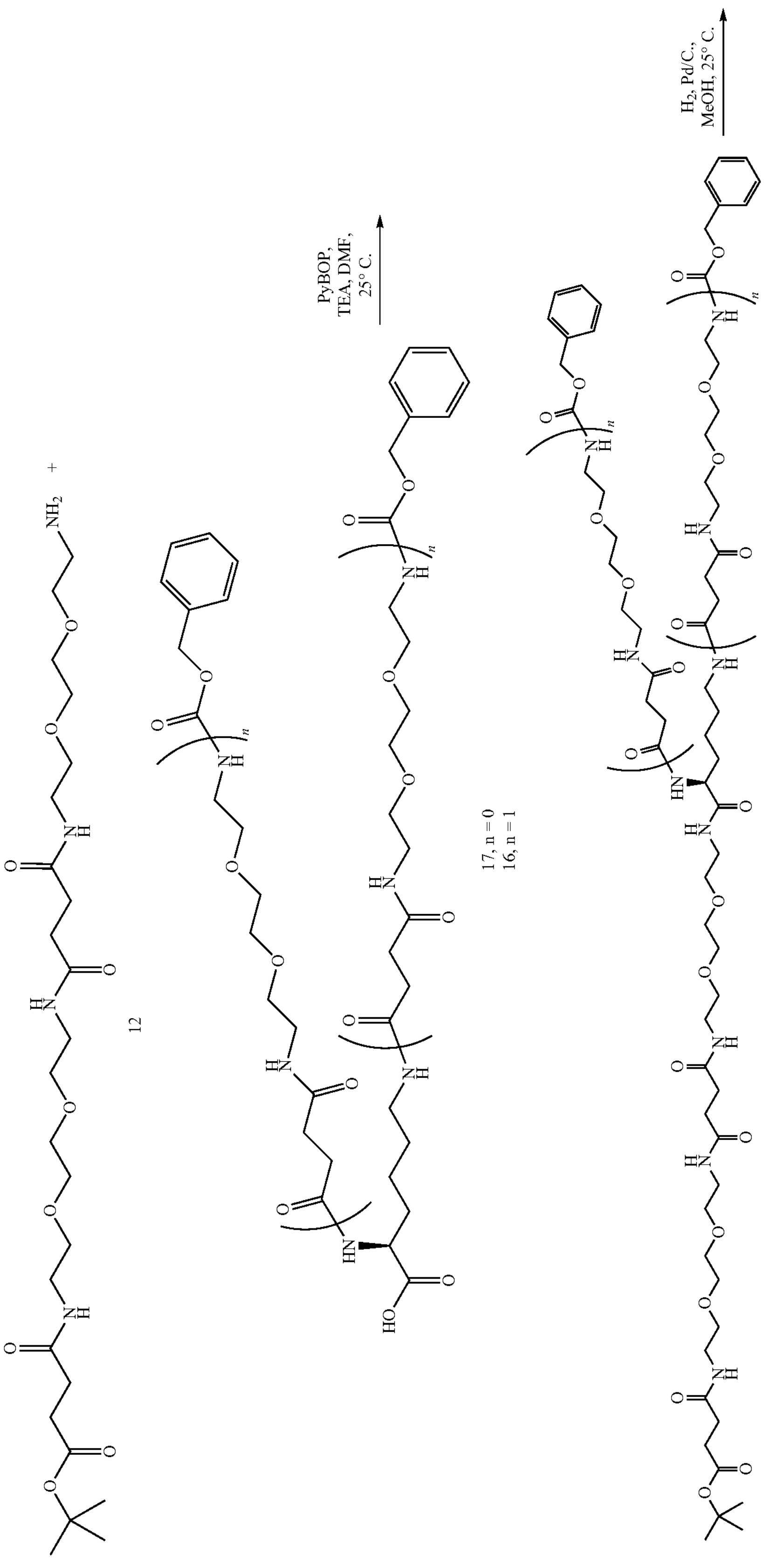
12
17, n = 0
16, n = 1
18, n = 0
19, n = 1

-continued
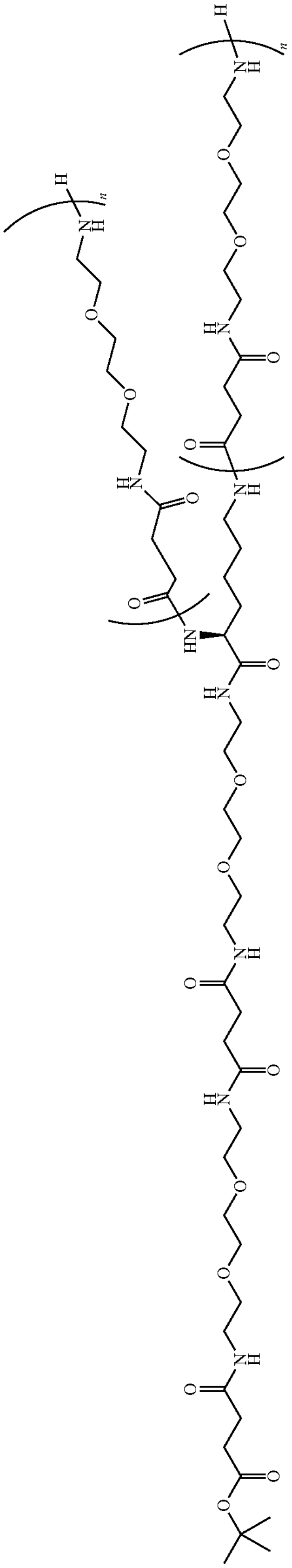
20, n = 0
21, n = 1

3,14-Dioxo-1-phenyl-2,7,10-trioxa-4,13-diazaheptadecan-17-oic acid (8)

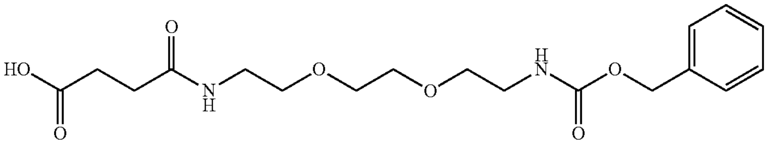 [SMILES: O=C(O)CCC(=O)NCCOCCOCCNC(=O)OCc1ccccc1]

To a solution of 5 (1 eq., 1.19 g, 1.17 mL, 8 mmol) in ACN (120 mL) was added dropwise over a period of 1.3 h a solution of 6 (1 eq., 801 mg, 8 mmol) in ACN (60 mL). The mixture was stirred at 25° C. for 21 h and then concentrated under reduced pressure. The obtained residue was dissolved in 2:1 v/v DCM/MeOH (120 mL). To the obtained mixture at iced water temperature were added TEA (2 eq., 1.62 g, 2.22 mL, 16 mmol) and dropwise 7 (1.3 eq., 1.77 g, 1.48 mL, 10.4 mmol). The mixture was stirred at 25° C. for 5 h. After evaporation under reduced pressure, a sat. $NaHCO_3$ aqueous solution (20 mL) was added and the aqueous layer was washed with EtOAc (3×15 mL). pH was adjusted to 1 with a concentrated HCl aqueous solution. The organic layer was extracted with EtOAc (3×15 mL), washed with water (10 mL), dried over anhydrous $Na_2SO_4$ and concentrated under vacuum to afford a colorless gel (2.04 g, 67%).

$^1$H NMR (400 MHz, $CDCl_3$) δ 9.85 (s, 1H), 7.39-7.26 (m, 5H), 6.93 (s, 1H), 6.53 (s, 1H), 5.13 (s, 1H), 5.08 (s, 1H), 3.63-3.55 (m, 4H), 3.57-3.47 (m, 4H), 3.46-3.34 (m, 4H), 2.70-2.57 (m, 2H), 2.45 (dt, J=13.0, 6.0 Hz, 2H). $^{13}$C NMR (101 MHz, $CDCl_3$) δ 175.54, 172.54, 156.71, 136.55, 128.65, 128.32, 128.24, 70.27, 70.17, 70.10, 69.69, 40.88, 39.50, 31.00, 30.01.

Tert-butyl 3,14-dioxo-1-phenyl-2,7,10-trioxa-4,13-diazaheptadecan-17-oate (9)

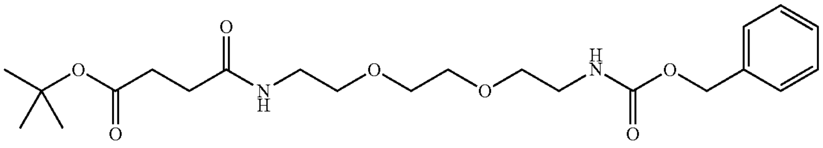 [SMILES: CC(C)(C)OC(=O)CCC(=O)NCCOCCOCCNC(=O)OCc1ccccc1]

To a solution of 8 (1 eq., 680 mg, 1.78 mmol) in DCM (2.34 mL) were added tert-butanol (2 eq., 263 mg, 0.338 mL, 3.56 mmol), DMAP (0.2 eq., 43.4 mg, 0.356 mmol) and DCC (1.1 eq., 403 mg, 1.96 mmol). The mixture was stirred at 25° C. for 20 h. After evaporation under vacuum, the crude product was purified by reverse-phase flash chromatography using a linear gradient of 10-55% v/v ACN (0.1% v/v TFA) in $H_2O$ (0.1% v/v TFA) to afford after lyophilization a colorless oil (208 mg, 27%).

$^1$H NMR (400 MHz, MeOD) δ 7.44-7.23 (m, 5H), 5.08 (s, 2H), 3.64-3.57 (m, 4H), 3.53 (dt, J=9.0, 5.5 Hz, 4H), 3.38-3.32 (m, 4H), 2.50 (td, J=6.5, 1.5 Hz, 2H), 2.42 (td, J=6.5, 1.5 Hz, 2H), 1.44 (s, 9H). $^{13}$C NMR (101 MHz, MeOD) δ 174.53, 173.61, 158.86, 138.37, 129.46, 128.98, 128.83, 81.67, 71.28, 70.95, 70.58, 67.43, 41.70, 40.37, 31.68, 31.57, 28.33. HRMS (ESI): calculated for $C_{22}H_{34}N_{207}Na^+[M+Na]^+$: 461.2264, found 461.2272.

Tert-butyl 4-((2-(2-(2-aminoethoxy)ethoxy)ethyl)amino)-4-oxobutanoate (10)

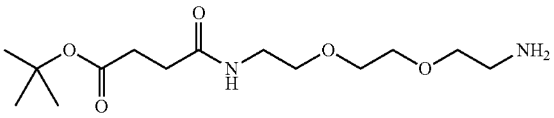 [SMILES: CC(C)(C)OC(=O)CCC(=O)NCCOCCOCCN]

To a solution of 9 (1 eq., 173 mg, 0.395 mmol) in anhydrous MeOH (2 mL) was added Pd/C (4.54%, 19.1 mg, 0.018 mmol). The mixture was stirred under $H_2$ (1 atm) at 25° C. for 2.5 h. The mixture was filtered through a hydrophobic PTFE syringe filter (pore: 0.22 M, diam.: 13 mm) and rinsed with MeOH. MeOH was evaporated under vacuum to afford a colorless oil (126 mg, quant.).

$^1$H NMR (400 MHz, MeOD) δ 3.67-3.59 (m, 6H), 3.55 (t, J=5.6 Hz, 2H), 3.38-3.35 (m, 2H), 2.98-2.92 (m, 2H), 2.55-2.48 (m, 2H), 2.48-2.41 (m, 2H), 1.44 (s, 9H). $^{13}$C NMR (101 MHz, MeOD) δ 174.59, 173.63, 81.69, 71.33, 71.29, 70.78, 70.61, 41.39, 40.31, 31.67, 31.57, 28.32. HRMS (ESI): calculated for $C_{14}H_{29}N_2O_5+[M+H]^+$: 305.2076, found 305.2084.

Tert-butyl 3,14,17,28-tetraoxo-1-phenyl-2,7,10,21,24-pentaoxa-4,13,18,27-tetraazahentriacontan-31-oate (11)

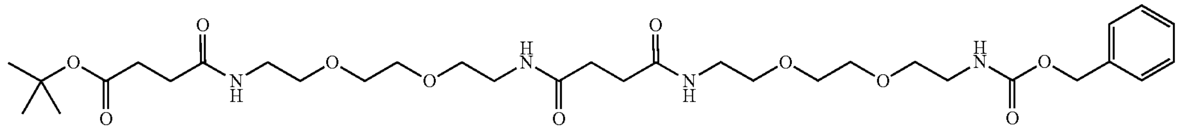 [SMILES: CC(C)(C)OC(=O)CCC(=O)NCCOCCOCCNC(=O)CCC(=O)NCCOCCOCCNC(=O)OCc1ccccc1]

To 10 (1 eq., 64.6 mg, 0.212 mmol) were added a solution of 8 (1 eq., 81.2 mg, 0.212 mmol) in anhydrous DMF (2.46 mL), PYBOP (1.5 eq., 165 mg, 0.318 mmol) and TEA (5 eq., 107 mg, 0.148 mL, 1.06 mmol). The mixture was stirred at 25° C. for 2 h. AcOH (4.1 eq., 50.0 μL, 0.873 mmol) was added and the crude product was purified by reverse-phase flash chromatography using a linear gradient of 10-65% v/v ACN (0.1% v/v TFA) in $H_2O$ (0.1% v/v TFA) to afford after lyophilization a colorless oil (37.6 mg, 26%).

$^1$H NMR (400 MHz, MeOD) δ 7.43-7.23 (m, 5H), 5.08 (s, 2H), 3.64-3.56 (m, 8H), 3.56-3.50 (m, 8H), 3.39-3.33 (m, 6H), 3.33-3.31 (m, 2H), 2.54-2.41 (m, 8H), 1.44 (s, 9H). BRMS (ESI): calculated for $C_{32}H_{53}N_{4}O_{11}$+$[M+H]^+$: 669.3711, found 669.3704.

Tert-butyl L-lysinate hydrochloride (14)

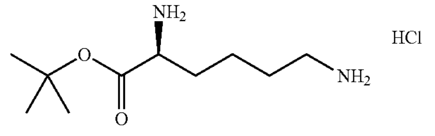

To a solution of 13 (1 eq., 120 mg, 322 μmol) in anhydrous MeOH (2.5 mL) was added Pd/C (3.57%, 12.2 mg, 11.5 μmol). The mixture was stirred under $H_2$ (1 atm) at 25° C. for 18.5 h.

The mixture was filtered through celite, rinsed with MeOH. MeOH was evaporated under vacuum to afford a pale yellow solid (80.9 mg, quant.).

Tert-butyl 1-amino-10,13,24-trioxo-3,6,17,20-tetraoxa-9,14,23-triazaheptacosan-27-oate (12)

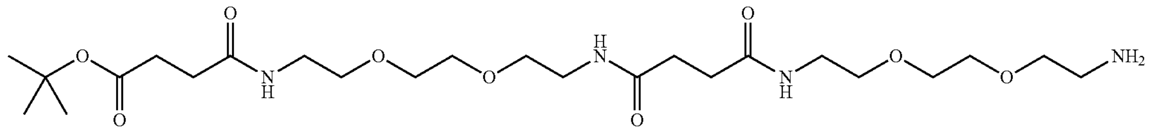 [SMILES: CC(C)(C)OC(=O)CCC(=O)NCCOCCOCCNC(=O)CCC(=O)NCCOCCOCCN]

To a solution of 11 (1 eq., 35 mg, 52.3 μmol) in anhydrous MeOH (1 mL) was added Pd/C (4.54%, 2.53 mg, 2.38 μmol). The mixture was stirred under $H_2$ (1 atm) at 25° C. for 18 h. The mixture was filtered through a hydrophobic PTFE syringe filter (pore: 0.22 M, diam.: 13 mm), rinsed with MeOH. MeOH was evaporated under vacuum to afford a colorless gel (28.7 mg, quant.).

$^1$H NMR (400 MHz, MeOD) δ 3.67-3.61 (m, 10H), 3.55 (td, J=5.6, 1.6 Hz, 6H), 3.38-3.34 (m, 6H), 3.03-2.95 (m, 2H), 2.54-2.42 (m, 8H), 1.44 (s, 9H).

$^1$H NMR (400 MHz, MeOD) δ 3.39 (dd, J=7.0, 5.6 Hz, 1H), 2.93 (t, J=7.6 Hz, 2H), 1.82-1.58 (m, 5H), 1.53-1.49 (m, 1H), 1.48 (s, 9H), 1.48-1.31 (m, 4H). $^{13}$C NMR (101 MHz, MeOD) δ 175.01, 82.70, 55.23, 40.55, 34.53, 28.45, 28.29, 23.46.

Tert-butyl (S)-23-(3,14-dioxo-1-phenyl-2,7,10-trioxa-4,13-diazaheptadecan-17-amido)-3,14,17-trioxo-1-phenyl-2,7,10-trioxa-4,13,18-triazatetracosan-24-oate (15)

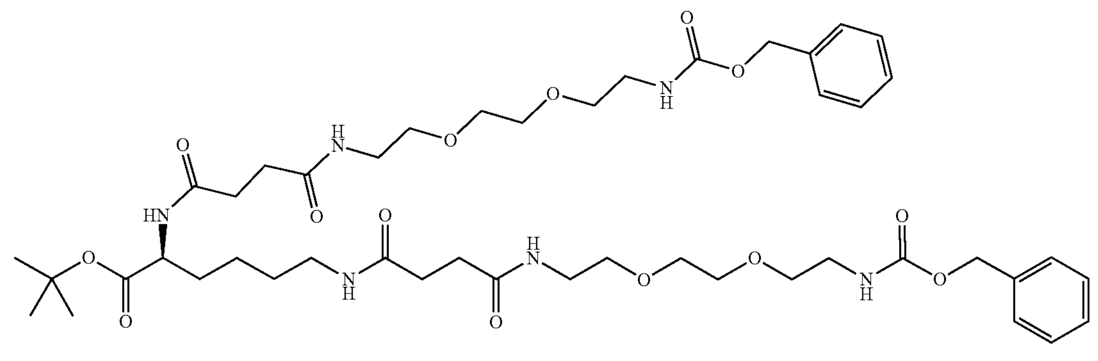 [SMILES: CC(C)(C)OC(=O)[C@H](CCCCNC(=O)CCC(=O)NCCOCCOCCNC(=O)OCc1ccccc1)NC(=O)CCC(=O)NCCOCCOCCNC(=O)OCc1ccccc1]

To 14 (1 eq., 50.0 mg, 0.209 mmol) were added a solution of 8 (3 eq., 240 mg, 0.628 mmol) in anhydrous DCM (5.7 mL), TEA (3 eq., 63.6 mg, 0.0873 mL, 0.628 mmol), EDCI (3 eq., 120 mg, 0.628 mmol) and HOBt·$H_2O$ (0.3 eq., 9.62 mg, 0.063 mmol). The mixture was stirred at 25° C. for 6.5 h. DCM (30 mL) was added and the organic layer was washed with water (20 mL), a saturated $NaHCO_3$ aqueous solution (20 mL), dried over anhydrous $Na_2SO_4$ and concentrated under reduced pressure. The crude product was purified on a silica gel column eluted with 5-10% v/v MeOH in DCM to afford after evaporation under vacuum an orange oil (152 mg, 78%).

$^1H$ NMR (400 MHz, $CDCl_3$) δ 7.37-7.27 (m, 10H), 6.81 (s, 1H), 6.72 (s, 1H), 6.60 (s, 1H), 5.82-5.44 (m, 3H), 5.07 (s, 4H), 4.46-4.31 (m, 1H), 3.60-3.52 (m, 12H), 3.49 (t, J=4.5 Hz, 4H), 3.42-3.33 (m, 8H), 3.30-3.17 (m, 1H), 3.15-3.04 (m, 1H), 2.62-2.39 (m, 8H), 1.81-1.68 (m, 1H), 1.66-1.53 (m, 1H), 1.50-1.44 (m, 2H), 1.42 (s, 9H), 1.34-1.25 (m, 2H). $^{13}C$ NMR (101 MHz, $CDCl_3$) δ 172.70, 172.60, 172.37, 172.27, 171.58, 156.64, 136.70, 128.59, 128.18, 81.87, 70.31, 70.09, 69.78, 66.71, 52.51, 40.97, 39.39, 38.76, 31.74, 31.67, 31.59, 31.43, 31.40, 30.99, 28.08, 22.03.

(S)-23-(3,14-Dioxo-1-phenyl-2,7,10-trioxa-4,13-diazaheptadecan-17-amido)-3,14,17-trioxo-1-phenyl-2,7,10-trioxa-4,13,18-triazatetracosan-24-oic acid (16)

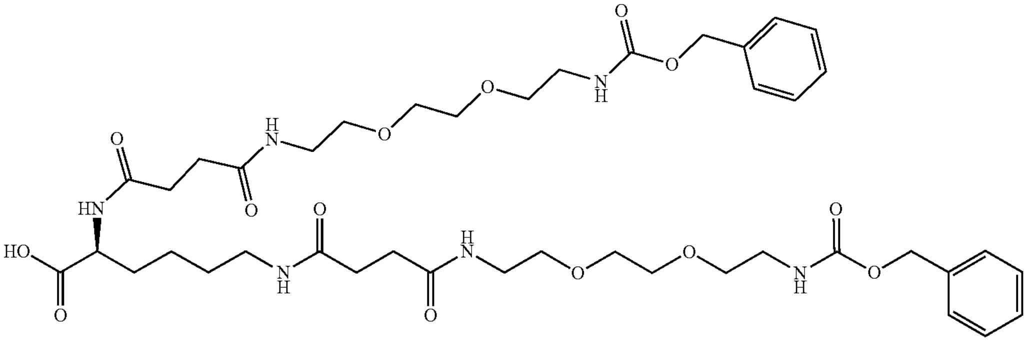 [SMILES: O=C(CCC(=O)NCCOCCOCCNC(=O)OCc1ccccc1)NCCCC[C@H](NC(=O)CCC(=O)NCCOCCOCCNC(=O)OCc1ccccc1)C(=O)O]

To a solution of 15 (1 eq., 34.1 mg, 0.037 mmol) in DCM (1 mL) was added TFA (244 eq., 666 L, 8.966 mmol). The mixture was stirred at 25° C. for 6.5 h. After evaporation under vacuum, $H_2O$ (200 μL) was added to afford after lyophilization a pale yellow oil (33.5 mg, quant.).

$^1H$ NMR (400 MHz, MeOD) δ 7.40-7.23 (m, 10H), 5.07 (s, 4H), 4.40-4.31 (m, 1H), 3.63-3.49 (m, 16H), 3.37-3.31 (m, 8H), 3.16 (t, J=5.2 Hz, 2H), 2.60-2.38 (m, 8H), 1.90-1.77 (m, 1H), 1.76-1.63 (m, 1H), 1.57-1.46 (m, 2H), 1.45-1.34 (m, 2H). $^{13}C$ NMR (101 MHz, MeOD) δ 175.50, 174.78, 158.93, 138.32, 129.46, 128.97, 128.78, 71.24, 71.07, 70.66, 67.43, 53.56, 41.67, 40.32, 40.02, 32.35, 32.19, 32.05, 29.83, 24.12.

Tert-butyl (S)-9-(((benzyloxy)carbonyl)amino)-3,10,21,24,35-pentaoxo-1-phenyl-2,14,17,28,31-pentaoxa-4,11,20,25,34-pentaazaoctatriacontan-38-oate (18)

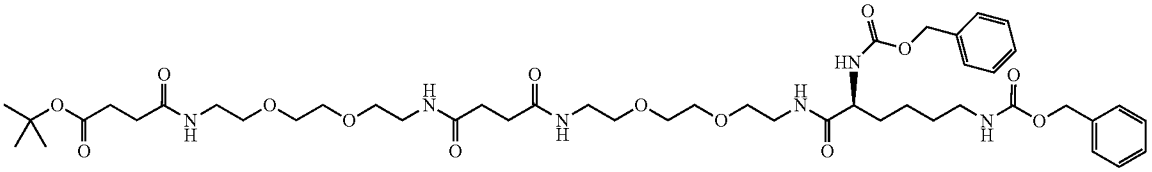 [SMILES: CC(C)(C)OC(=O)CCC(=O)NCCOCCOCCNC(=O)CCC(=O)NCCOCCOCCNC(=O)[C@H](CCCCNC(=O)OCc1ccccc1)NC(=O)OCc1ccccc1]

To a solution of 17 (1 eq., 10.9 mg, 0.026 mmol) in anhydrous DMF (152 μL) were added a solution of 12 (1 eq., 14 mg, 0.026 mmol) in anhydrous DMF (152 μL), PYBOP (1.5 eq., 20.4 mg, 0.039 mmol) and TEA (5 eq., 13.2 mg, 18.2 μL, 0.131 mmol). The mixture was stirred at 25° C. for 4.5 h. AcOH (5 eq., 7.5 μL, 0.131 mmol) was added and the crude product was purified by reverse-phase semi-preparative HPLC using a linear gradient of 10-70% v/v ACN (0.1% v/v TFA) in $H_2O$ (0.1% v/v TFA) to afford after lyophilization a colorless oil (15.7 mg, 64%).

$^1$H NMR (400 MHz, MeOD) δ 7.38-7.25 (m, 10H), 5.08 (s, 2H), 5.05 (s, 2H), 4.12-3.98 (m, 1H), 3.62-3.49 (m, 16H), 3.41-3.32 (m, 8H), 3.10 (t, J=6.8 Hz, 2H), 2.54-2.40 (m, 8H), 1.82-1.58 (m, 2H), 1.54-1.46 (m, 2H), 1.43 (s, 9H), 1.41-1.30 (m, 2H). BRMS (ESI): calculated for $C_{46}H_{71}N_6O_{14}$+[M+H]$^+$: 931.5028, found 931.5047.

Tert-butyl (S)-23-(3,14-dioxo-1-phenyl-2,7,10-trioxa-4,13-diazaheptadecan-17-amido)-3,14,17,24,35,38,49-heptaoxo-1-phenyl-2,7,10,28,31,42,45-heptaoxa-4,13,18,25,34,39,48-heptaazadopentacontan-52-oate (19)

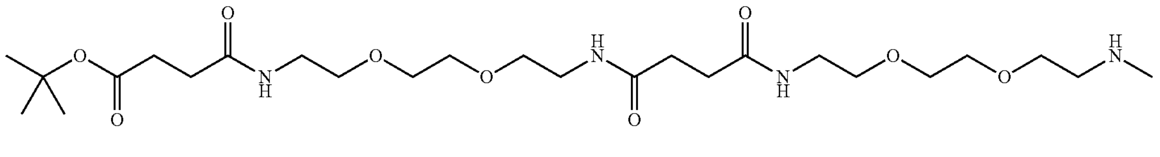

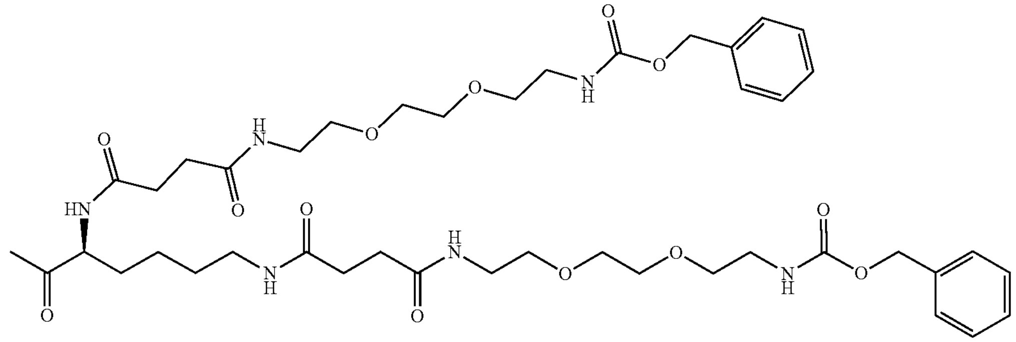

To a solution of 16 (0.978 eq., 22.4 mg, 0.026 mmol) in anhydrous DMF (152 μL) were added a solution of 12 (1 eq., 14.0 mg, 0.026 mmol) in anhydrous DMF (152 μL), PYBOP (1.5 eq., 20.4 mg, 0.039 mmol) and TEA (5 eq., 13.2 mg, 18.2 L, 0.131 mmol). The mixture was stirred at 25° C. for 4.5 h. AcOH (5 eq., 7.5 L, 0.131 mmol) was added and the crude product was purified by reverse-phase semi-preparative HPLC using a linear gradient of 10-70% v/v ACN (0.1% v/v TFA) in $H_2O$ (0.1% v/v TFA) to afford after lyophilization a colorless oil (13.1 mg, 37%).

$^1$H NMR (400 MHz, MeOD) δ 7.39-7.26 (m, 10H), 5.07 (s, 4H), 4.26 (dd, J=9.2, 4.8 Hz, 1H), 3.63-3.57 (m, 16H), 3.57-3.49 (m, 16H), 3.40-3.31 (m, 16H), 3.15 (t, J=7.0 Hz, 2H), 2.55-2.39 (m, 16H), 1.88-1.76 (m, 1H), 1.69-1.58 (m, 1H), 1.56-1.46 (m, 2H), 1.44 (s, 9H), 1.41-1.32 (m, 2H). BRMS (ESI): calculated for $C_{66}H_{108}N_{10}O_{22}^{2+}$ [M+2H]2+/2: 696.3820, found 696.3862.

Tert-butyl (S)-30,34-diamino-4,15,18,29-tetraoxo-8,11,22,25-tetraoxa-5,14,19,28-tetraazatetratriacontanoate (20)

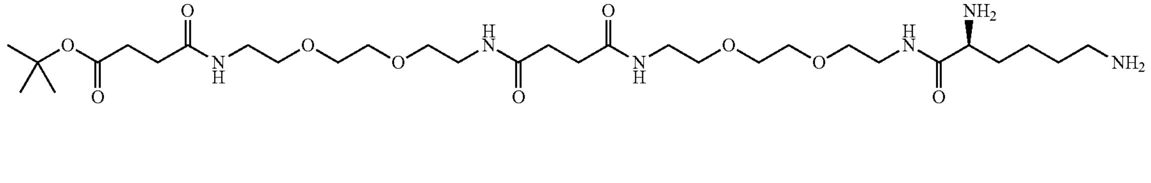 [SMILES: CC(C)(C)OC(=O)CCC(=O)NCCOCCOCCNC(=O)CCC(=O)NCCOCCOCCNC(=O)[C@@H](N)CCCCN]

To a solution of 18 (1 eq., 15.7 mg, 16.9 mol) in anhydrous MeOH (mL) was added Pd/C (16.2%, 2.9 mg, 2.73 mol). The mixture was stirred under $H_2$ (1 atm) at 25° C. for 3 h. The mixture was filtered through a hydrophobic PTFE syringe filter (pore: 0.22 M, diam.: 13 mm), rinsed with MeOH. MeOH was evaporated under vacuum to afford a colorless gel (11.5 mg, quant.).

$^1H$ NMR (400 MHz, MeOD) δ 3.65-3.51 (m, 16H), 3.46-3.35 (m, 8H), 2.88-2.80 (m, 2H), 2.56-2.41 (m, 8H), 1.75-1.51 (m, 4H), 1.44 (s, 9H), 1.43-1.32 (m, 2H). BRMS (ESI): calculated for $C_{30}H_{59}N_6O_1$+[M+H]: 663.4292, found 663.4307.

Tert-butyl (S)-1-amino-19-(4-((2-(2-(2-aminoethoxy)ethoxy)ethyl)amino)-4-oxobutanamido)-10,13,20,31,34,45-hexaoxo-3,6,24,27,38,41-hexaoxa-9,14,21,30,35,44-hexaazaoctatetracontan-48-oate (21)

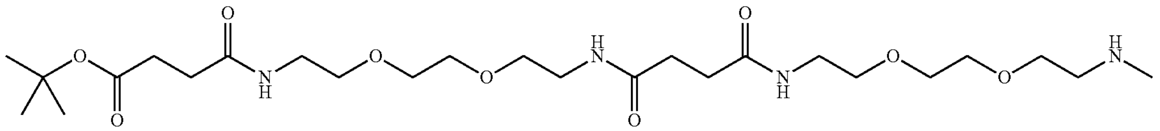

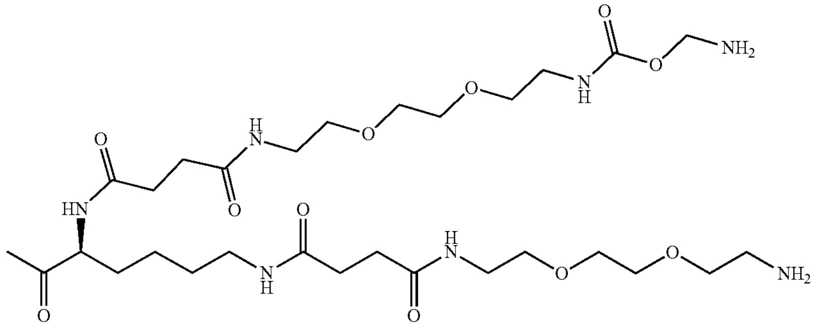

To a solution of 19 (1 eq., 13.1 mg, 9.41 mol) in anhydrous MeOH (1 mL) was added Pd/C (84.8%, 8.5 mg, 7.99 mol). The mixture was stirred under $H_2$ (1 atm) at 25° C. for 4 h. The mixture was filtered through a hydrophobic PTFE syringe filter (pore: 0.22 M, diam.: 13 mm), rinsed with MeOH. MeOH was evaporated under vacuum to afford a colorless gel (10.5 mg, 99%).

$^1H$ NMR (400 MHz, MeOD) δ 4.25 (dd, J=9.2, 5.0 Hz, 1H), 3.68-3.59 (m, 20H), 3.58-3.51 (m, 12H), 3.39-3.35 (m, 12H), 3.17 (t, J=7.2 Hz, 2H), 3.06-3.00 (m, 4H), 2.55-2.42 (m, 16H), 1.89-1.76 (m, 1H), 1.70-1.59 (m, 1H), 1.56-1.46 (m, 2H), 1.44 (s, 9H), 1.43-1.34 (m, 2H). BRMS (ESI): calculated for $C_{50}H_{96}N_{10}O_{18}^{2+}$ [M+2H]2+/2: 562.3452, found 562.3481.

Scheme 4 Synthesis of the Cy5.5 and DY547 dimers.
1st generation Cy5.5 dimers
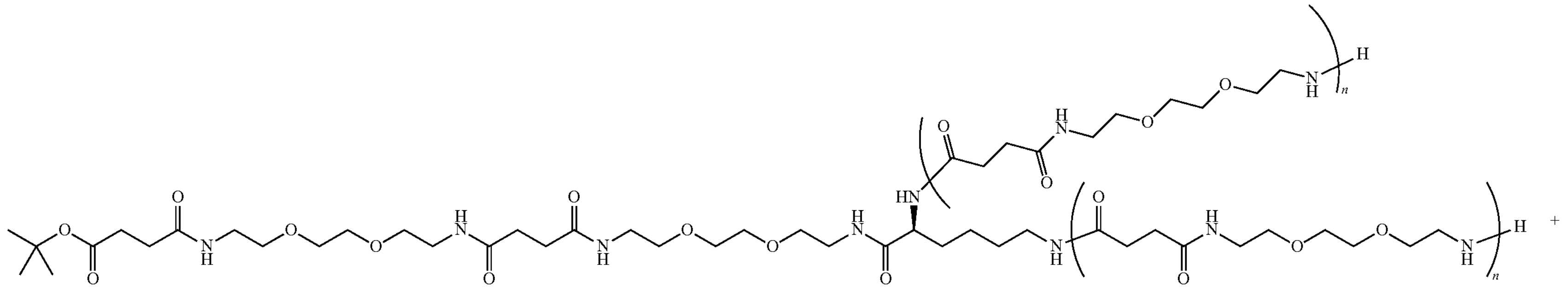
20, n = 0
21, n = 1
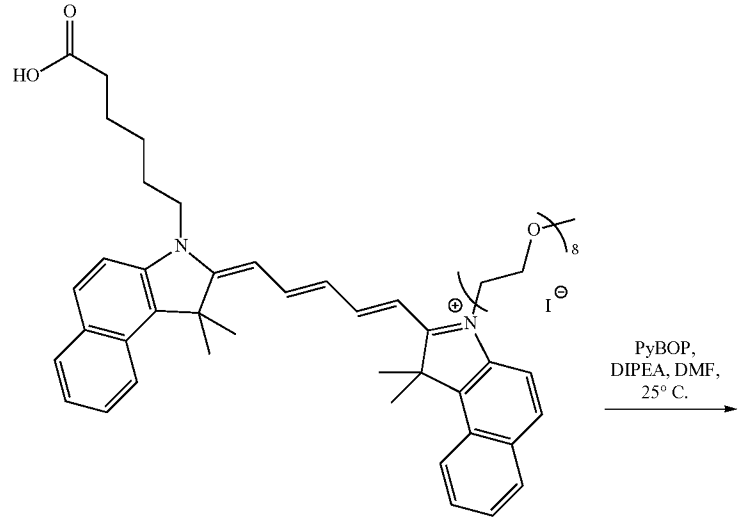
22

-continued
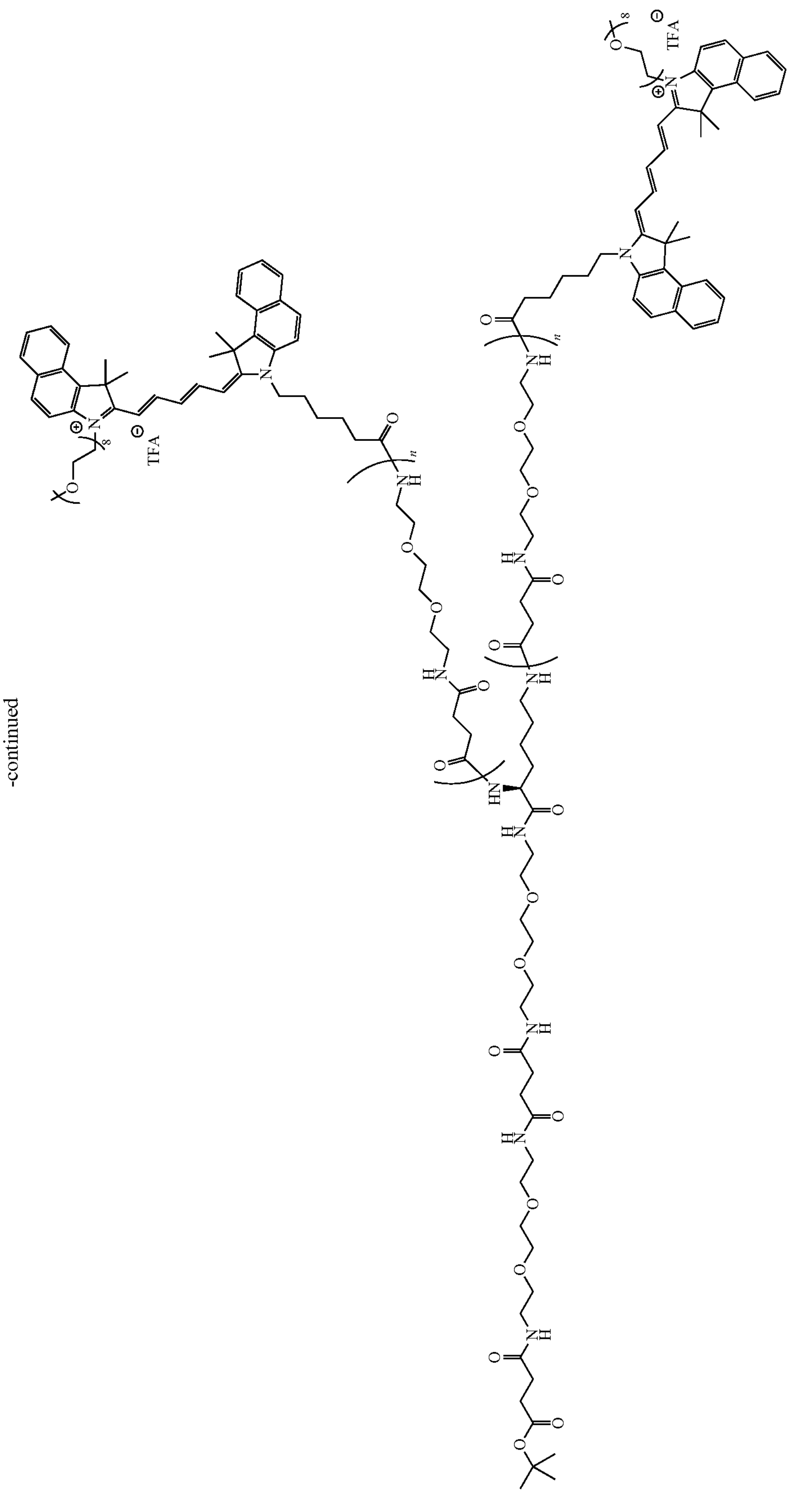
1, n = 0
2, n = 1

-continued
1st generation DY647 dimers
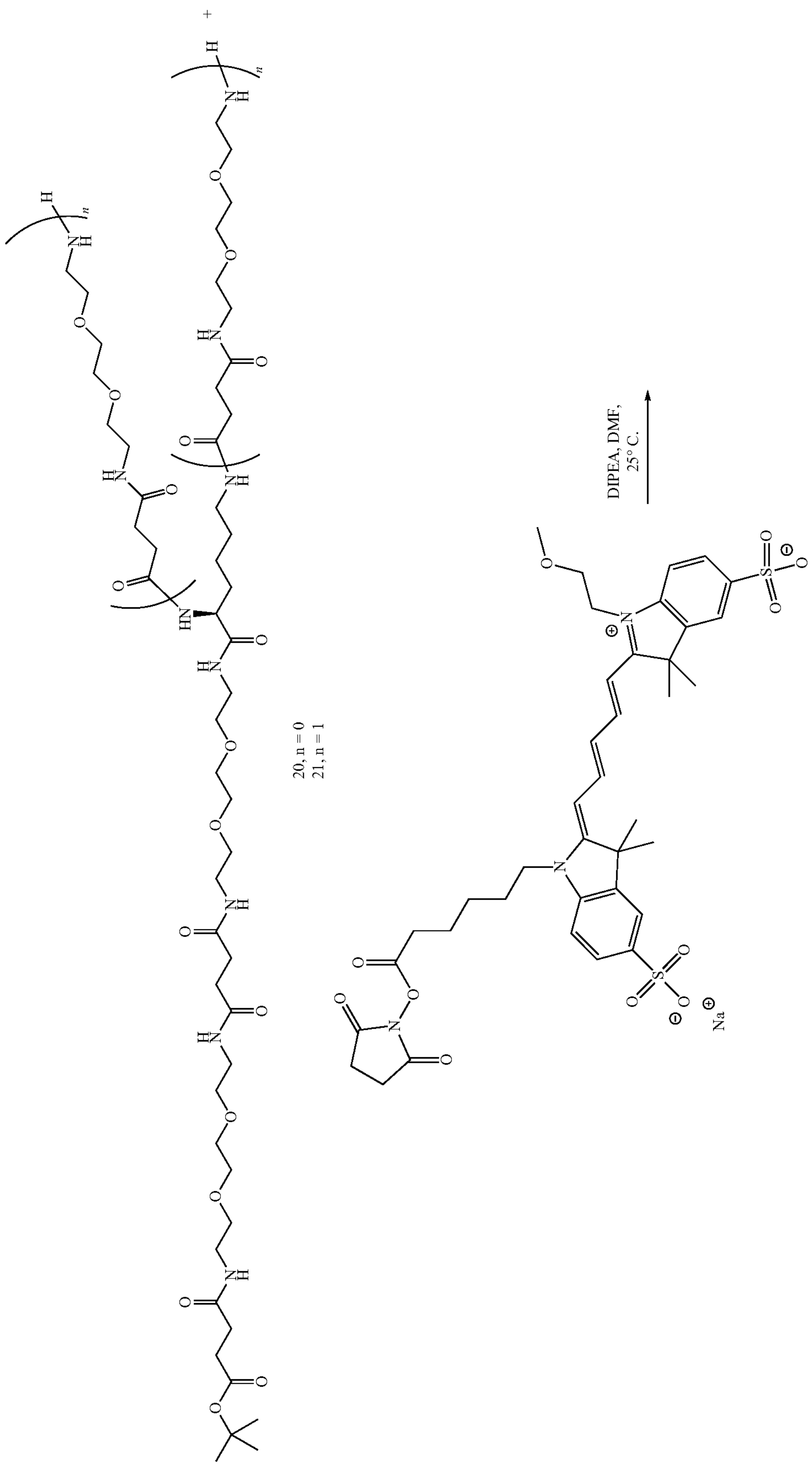
20, n = 0
21, n = 1
23

-continued
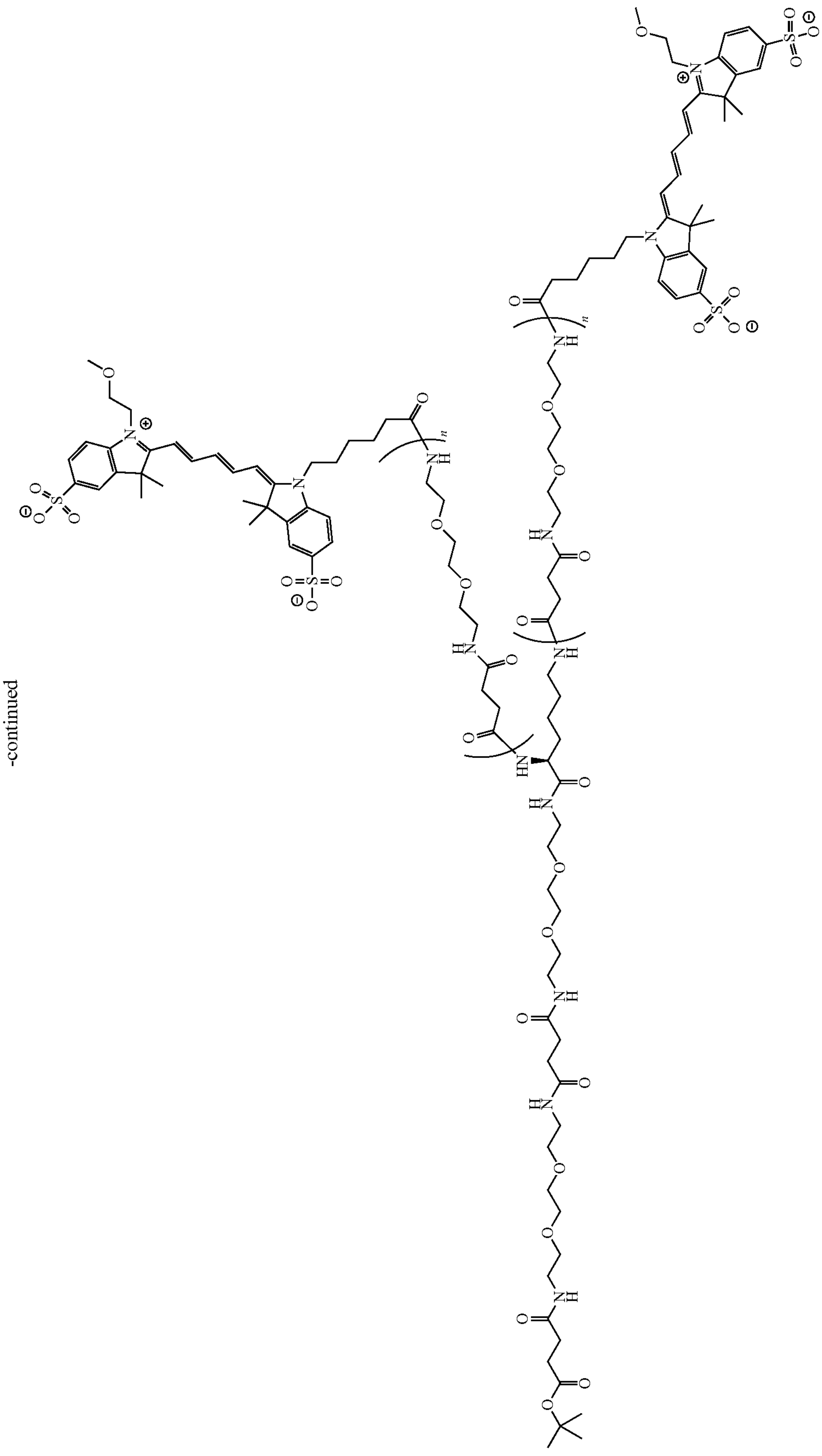
3, n = 0
4, n = 1

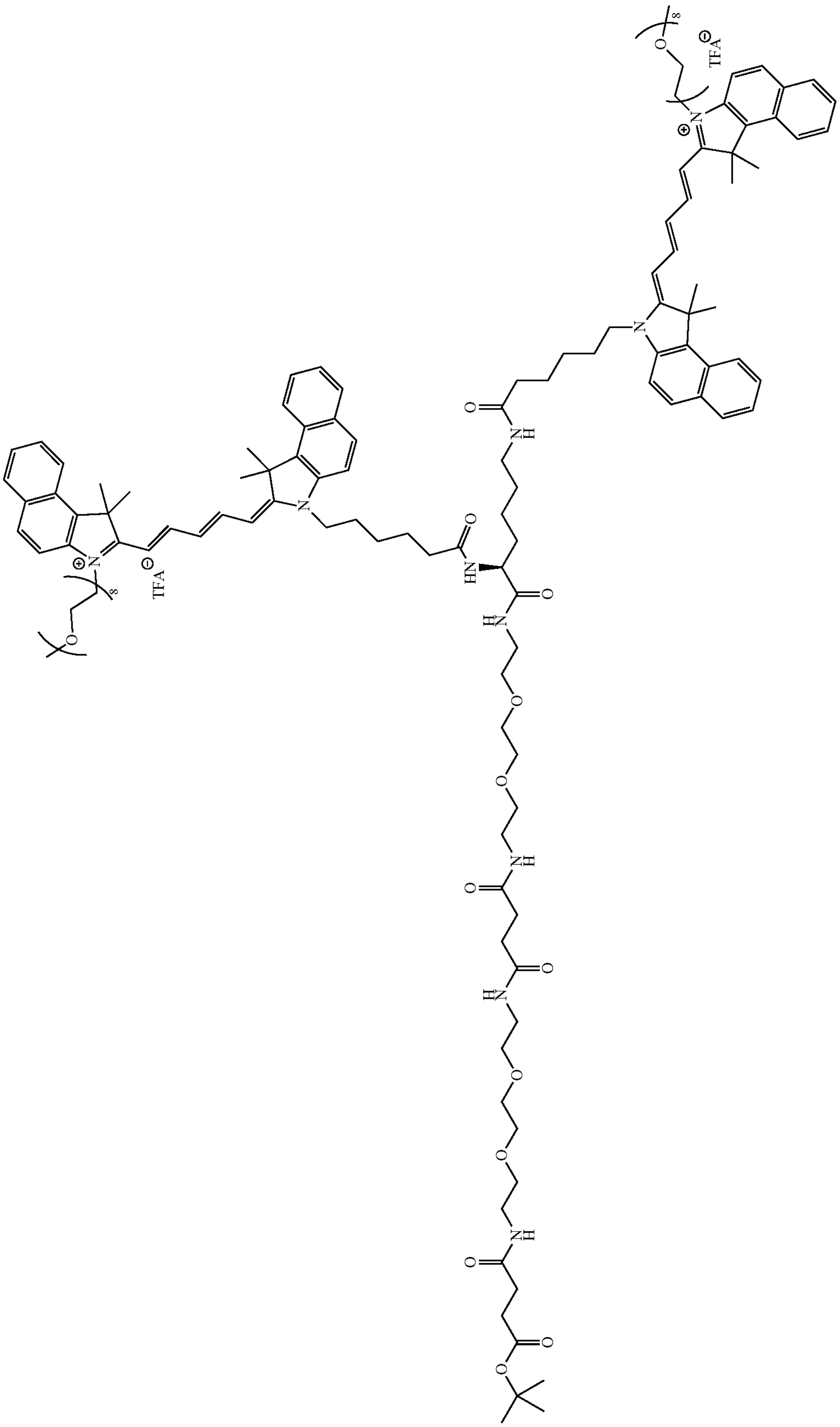

To a solution of 20 (1 eq., 0.2 mg, 0.33 mol) in anhydrous DMF (50 μL) were added a solution of 22 (1.9 eq., 0.7 mg, 0.62 mol) in anhydrous DMF (50 μL), PYBOP (2 eq., 0.3 mg, 0.65 mol) and DIPEA (4 eq., 0.2 μL, 1.31 mol). The mixture was stirred at 25° C. for 3 h. $H_2O$ (100 μL) was added and the crude product was purified by reverse-phase semi-preparative HPLC using a linear gradient of 30-95% v/v ACN (0.1% v/v TFA) in $H_2O$ (0.10% v/v TFA) to afford after lyophilization a blue solid (0.6 mg, 67%).

HRMS (ESI): calculated for $C_{142}H_{204}N_{10}O_{28}^{2+}$ [M]2+/2: 1248.7423, found 1249.2413.

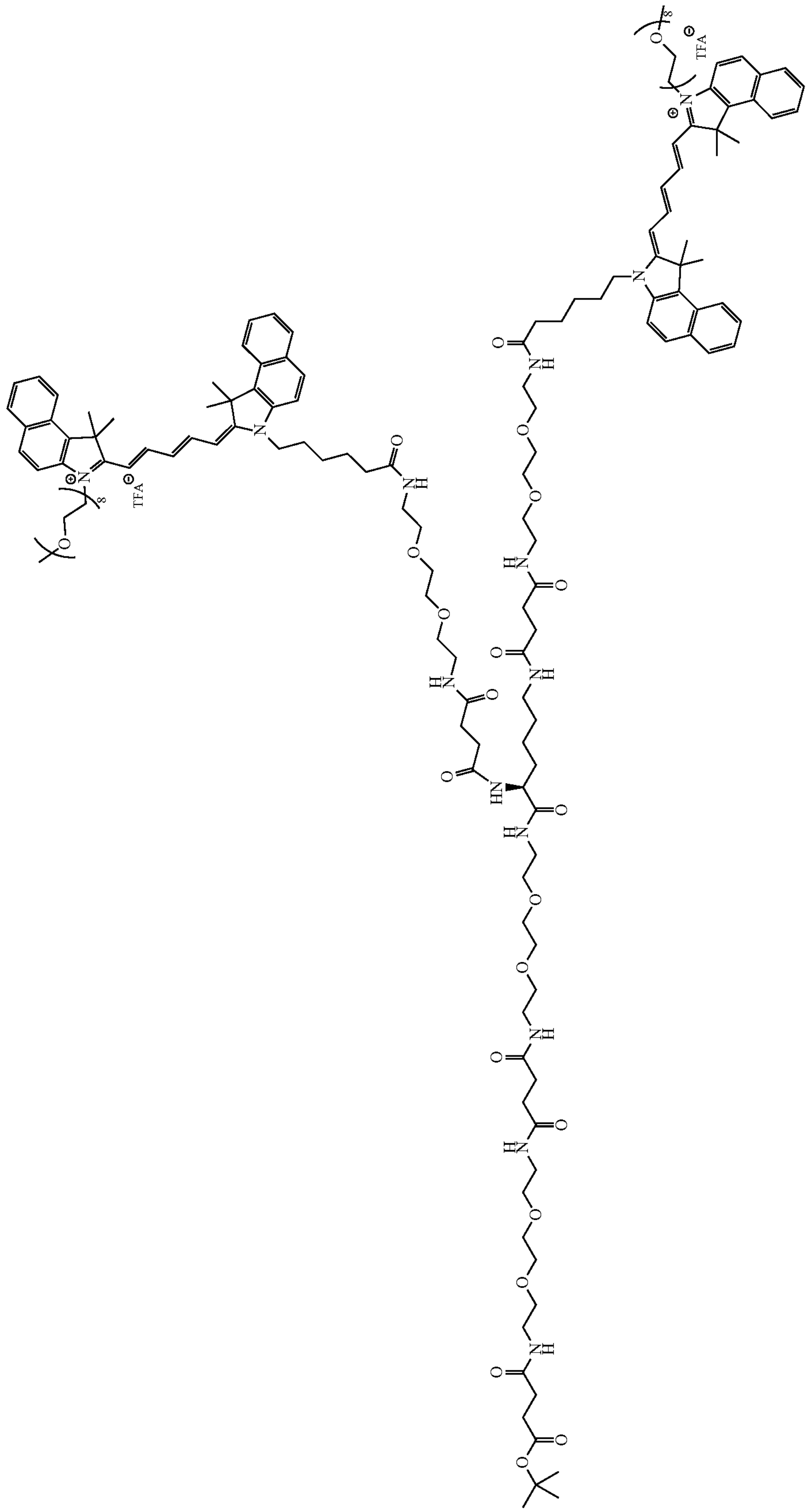

To a solution of 21 (1 eq., 0.4 mg, 0.33 mol) in anhydrous DMF (50 μL) were added a solution of 22 (1.9 eq., 0.7 mg, 0.62 mol) in anhydrous DMF (50 μL), PYBOP (2 eq., 0.3 mg, 0.65 mol) and DIPEA (4 eq., 0.2 μL, 1.31 mol). The mixture was stirred at 25° C. for 3 h. $H_2O$ (100 μL) was added and the crude product was purified by reverse-phase semi-preparative HPLC using a linear gradient of 30-95% v/v ACN (0.1% v/v TFA) in $H_2O$ (0.10% v/v TFA) to afford after lyophilization a blue solid (0.5 mg, 48%).

HRMS (ESI): calculated for $C_{162}H_{240}N_{14}O_{36}^{2+}$[M]2+/2: 1478.8690, found 1479.3667.

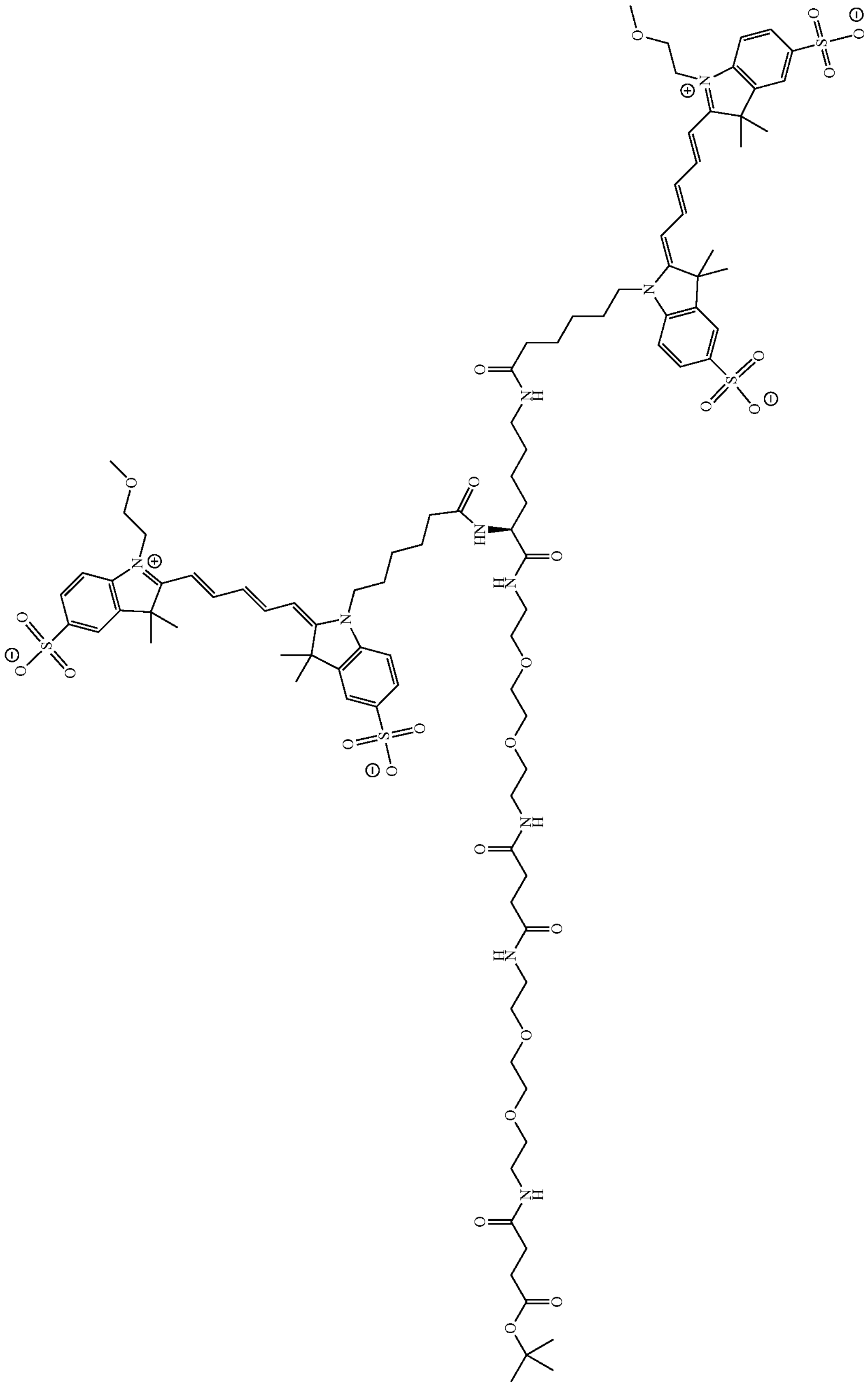

To a solution of 20 (1 eq., 0.2 mg, 0.33 mol) in anhydrous DMF (50 μL) were added a solution of 23 (1.9 eq., 0.5 mg, 0.62 mol) in anhydrous DMF (50 μL) and DIPEA (4 eq., 0.2 μL, 1.31 μmol). The mixture was stirred at 25° C. for 4.5 h. $H_2O$ (100 μL) was added and the crude product was purified by reverse-phase semi-preparative HPLC using a linear gradient of 10-75% v/v ACN (0.1% v/v TFA) in $H_2O$ (0.1% v/v TFA) to afford after lyophilization a blue solid (0.4 mg, 61%).

HRMS (ESI): calculated for $C_{98}H_{14}N_{10}O_{26}S_4^{2+}$ [M+4H] 2+/2: 1000.4412, found 1000.4409.

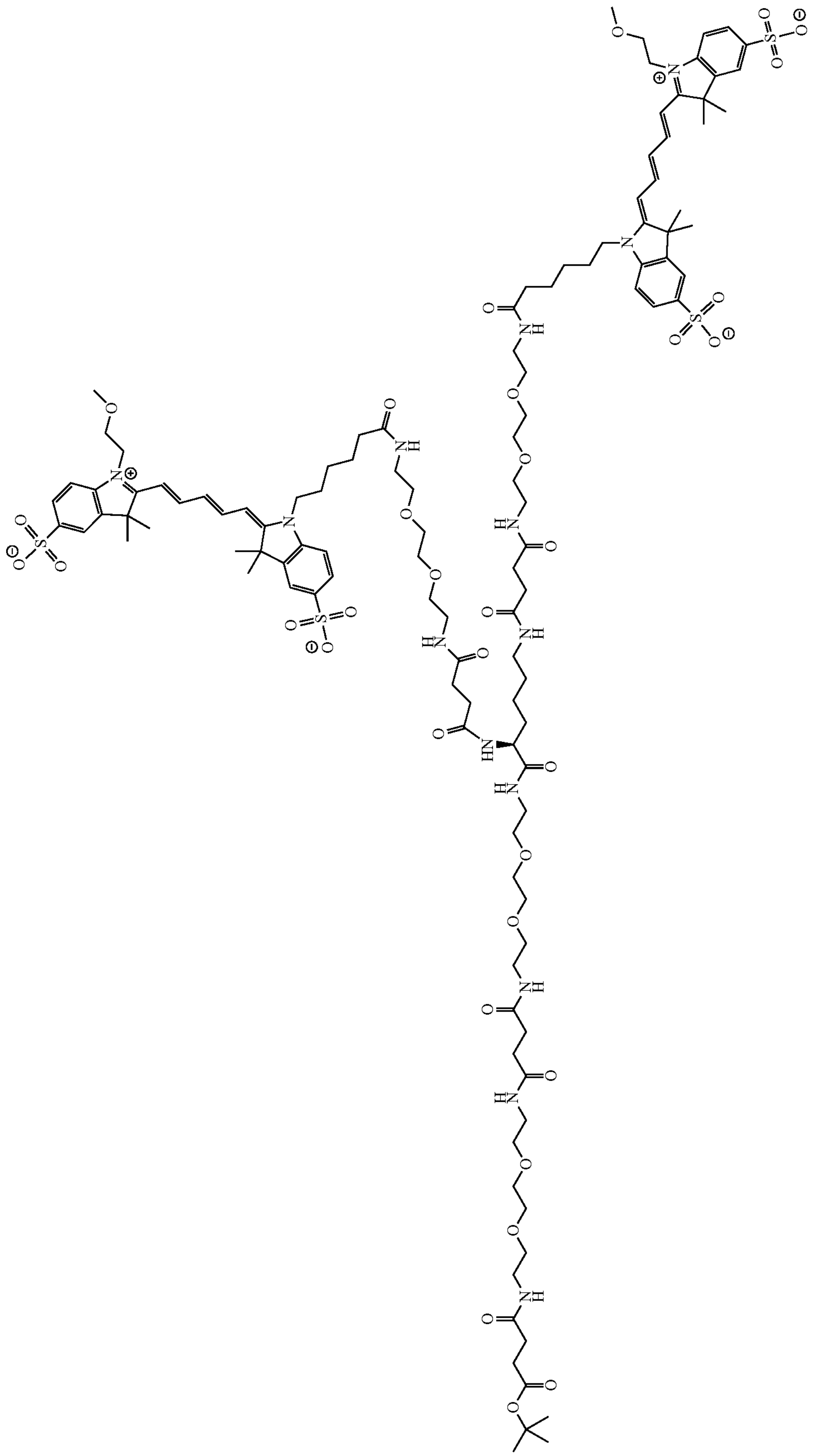

To a solution of 21 (1 eq., 0.4 mg, 0.33 mol) in anhydrous DMF (50 μL) were added a solution of 23 (1.9 eq., 0.5 mg, 0.62 mol) in anhydrous DMF (50 μL) and DIPEA (4 eq., 0.2 μL, 1.31 μmol). The mixture was stirred at 25° C. for 4.5 h. $H_2O$ (100 μL) was added and the crude product was purified by reverse-phase semi-preparative HPLC using a linear gradient of 10-75% v/v ACN (0.1% v/v TFA) in $H_2O$ (0.1% v/v TFA) to afford after lyophilization a blue solid (0.5 mg, 62%).

HRMS (ESI): calculated for $C_{118}H_{176}N_{14}O_{34}S_4^{2+}$[M+4H]2+/2: 1230.5678, found 1230.5693.

Absorption and Fluorescence Spectroscopy

General Information

Cy5.5 Dimers

Absorption spectra were recorded on a Shimadzu UV-2700i spectrophotometer and fluorescence spectra on a Horiba Fluoromax 4 spectrofluorometer. Fluorescence emission spectra were systematically recorded at 630 nm excitation wavelength at 20° C. All fluorescence spectra were corrected for instrumental effects. Fluorescence quantum yields (QY) were measured using Rhodamine 800 in EtOH as a reference (QY=25%).[ref] Turn-ON were calculated as a ratio of OY of compounds in EtOH to OY in water.

Ref A. Alessi, M. Salvalaggio, G. Ruzzon, *J. Lumin.* 2013, 134, 385-389.

DY647 Dimers

Absorption spectra were recorded on a Shimadzu UV-2700i spectrophotometer and fluorescence spectra on a Horiba Fluoromax 4 spectrofluorometer. Fluorescence emission spectra were systematically recorded at 600 nm excitation wavelength at 20° C. All fluorescence spectra were corrected for instrumental effects. Fluorescence quantum yields (QY) were measured using DID in MeOH as a reference (QY=33%).[ref] Turn-ON were calculated as a ratio of QY of compounds in EtOH to QY in water.

Ref I. Texier, et al., *J. Biomed. Opt.* 2009, 14, 054005.

TABLE 2

| | Compounds 4 and 5 | | | | | | Compounds A and B | | | | | |
|---|---|---|---|---|---|---|---|---|---|---|---|---|
| | Cpd 4 (n = 0) | | | Cpd 5 (n = 1) | | | Cpd A (n = 0) | | | Cpd B (n = 1) | | |
| Solvent | $\lambda_{abs}$, nm[a] | $\lambda_{em}$, nm[b] | QY, %[c] | $\lambda_{abs}$, nm[a] | $\lambda_{em}$, nm[b] | QY, %[c] | $\lambda_{abs}$, nm[a] | $\lambda_{em}$, nm[b] | QY, %[c] | $\lambda_{abs}$, nm[a] | $\lambda_{em}$, nm[b] | QY, %[c] |
| Acetone | 684 | 708 | 22.5 | 683 | 708 | 25.0 | 661 | 684 | 3.4 | 660 | 683 | 0.4 |
| Acetonitrile | 680 | 703 | 18.8 | 681 | 703 | 22.7 | 656 | 678 | 19.8 | 658 | 677 | 6.6 |
| EtOH | 684 | 708 | 22.1 | 685 | 708 | 26.5 | 654 | 676 | 31.1 | 653 | 673 | 35.1 |
| MeOH | 682 | 708 | 19.2 | 682 | 708 | 21.1 | 651 | 673 | 28.2 | 650 | 673 | 33.0 |
| $H_2O$ | 628 | 702 | 0.7 | 630 | 708 | 0.4 | 647 | 671 | 4.1 | 648 | 666 | 7.6 |

Photophysical properties of the dimers.
[a]Position of the absorption maximum.
[b]Position of the emission maximum.
[c]Fluorescence quantum yield.

TABLE 3

Fluorescence turn-on for the dimers, calculated as a ratio of quantum yields in EtOH to that in water (200 nM).

| Fluorogenic dimer | Turn-on |
|---|---|
| 4 (Cy5.5, n = 0) | 32 |
| 5 (Cy5.5, n = 1) | 66 |
| A (DY647, n = 0) | 7.6 |
| B (DY647, n = 1) | 4.6 |

Conclusions

1) Substitution of Cy5.5 fluorophore by Dy647 (a negatively charged fluorophore) reduces the Turn-ON efficacy harshly.
2) The presence of a PEG moiety between the fluorophore moiety and the lysine moiety allows to get a better Turn-ON response (table 3-compounds 4 and 5).

Example 3

Compounds 6 and 7 and comparative compounds C and D have the following formulas:

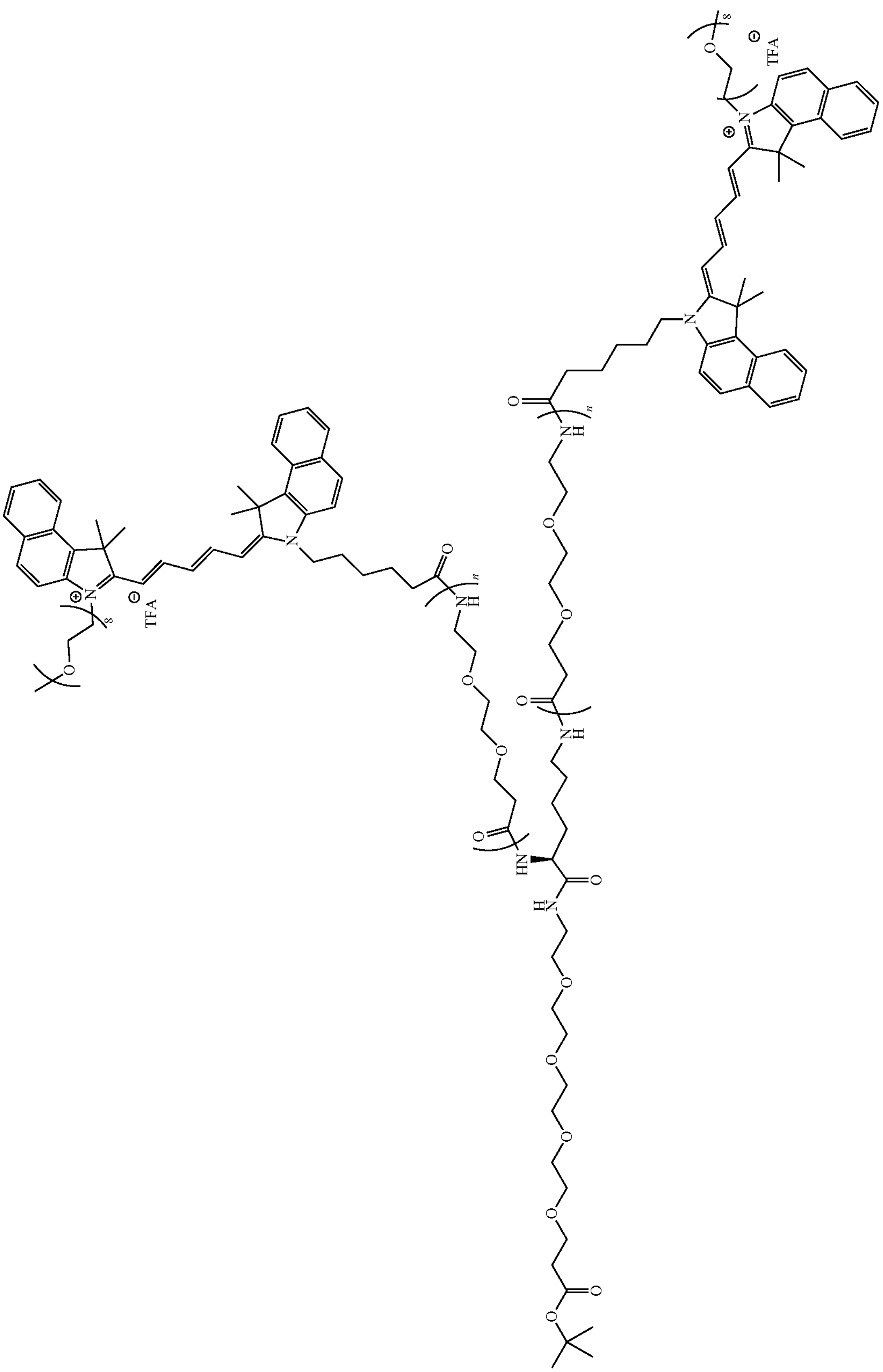

where n is 0 (compound 6) and n is 1 (compound 7); and

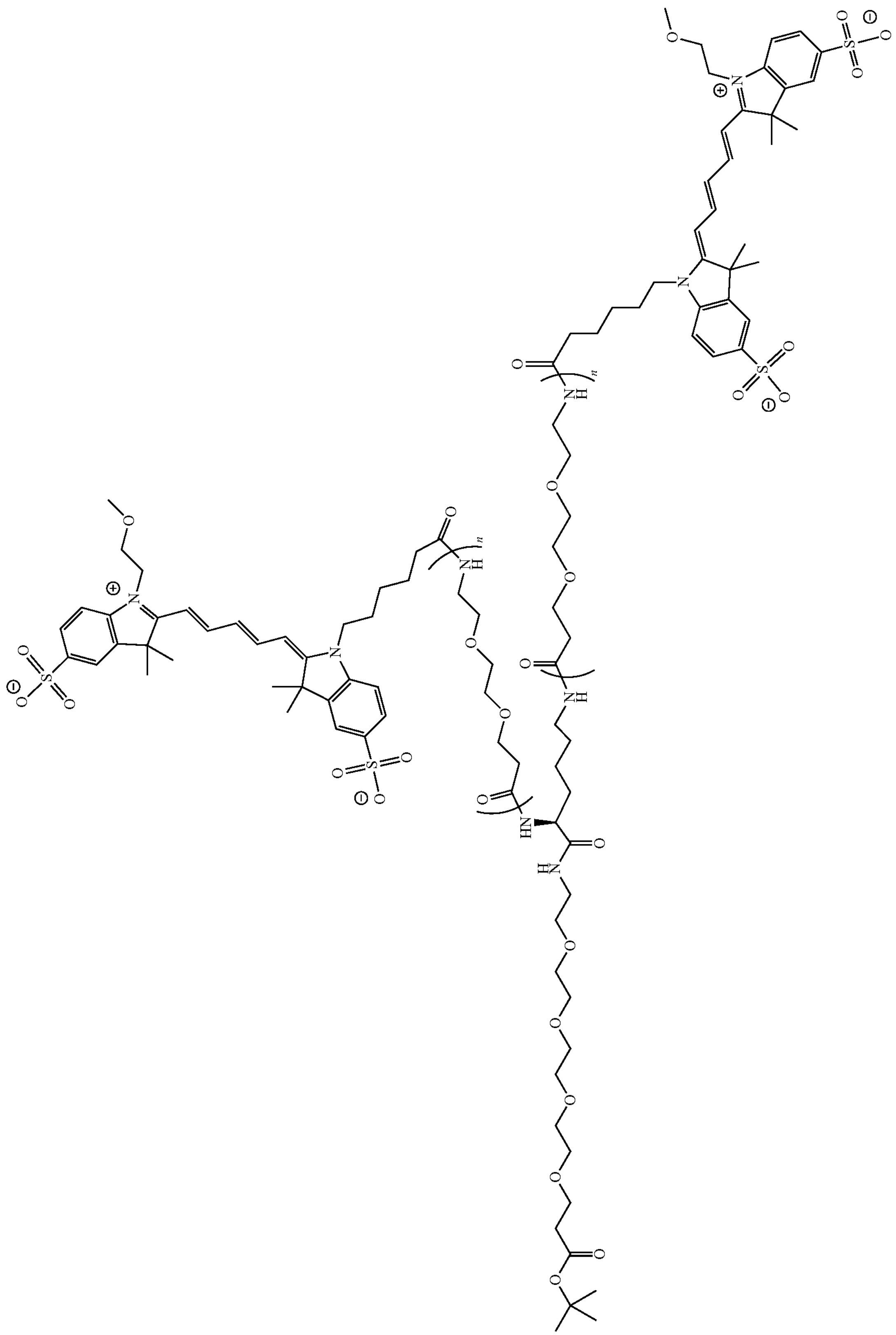

where n is 0 (compound C) and n is 1 (c<

Chemical Synthesis

Scheme 5 Synthesis of dimeric chains in solution.
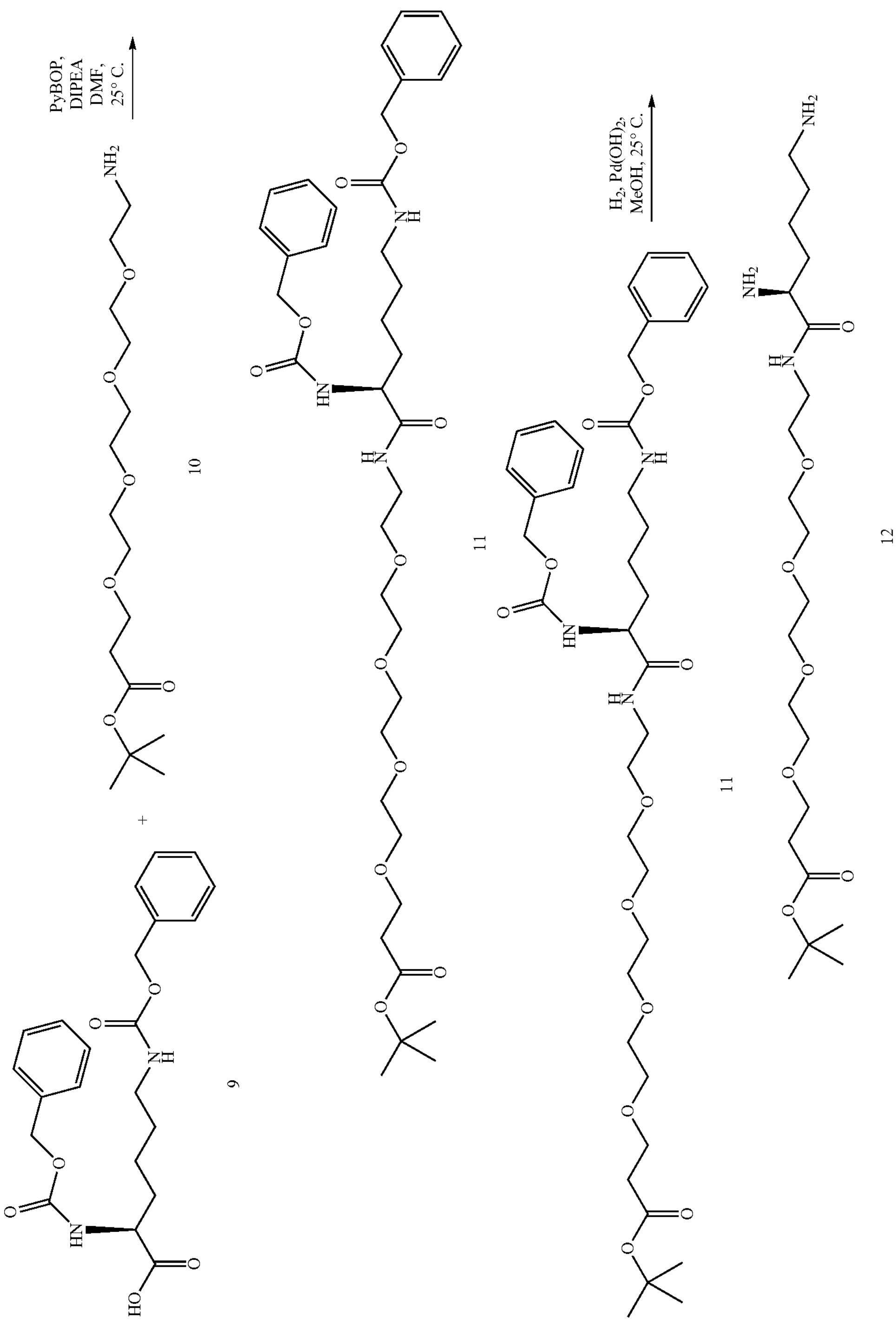
9 + 10
11
11
12

-continued
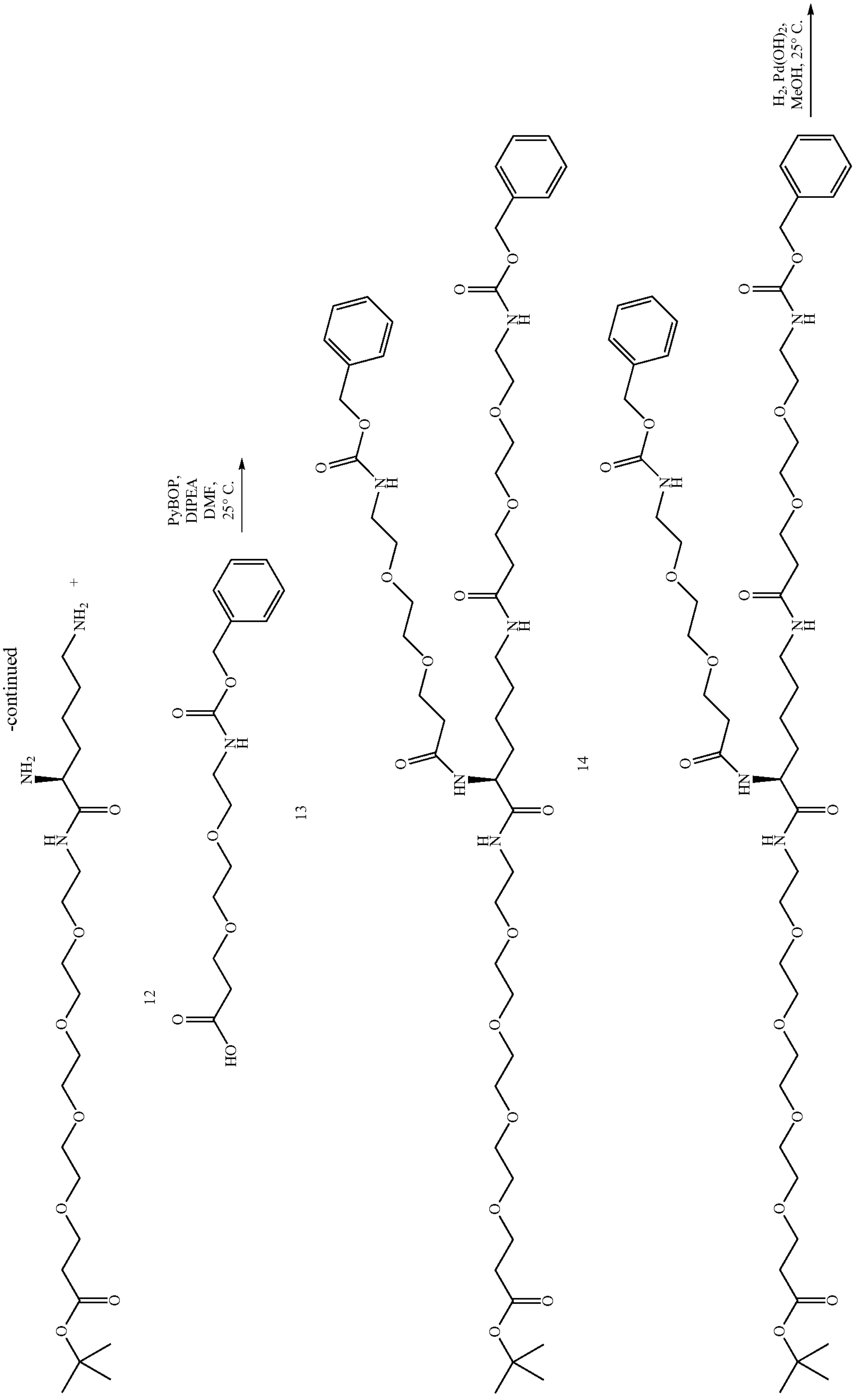
12
13
14
14

-continued
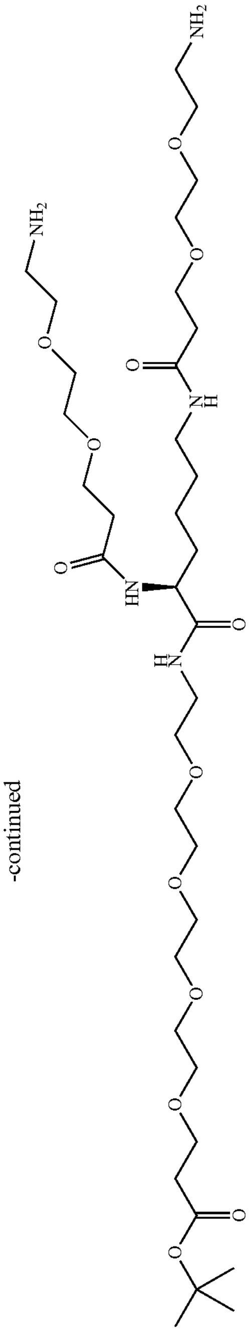
15

Tert-butyl (S)-9-(((benzyloxy)carbonyl)amino)-3,10-dioxo-1-phenyl-2,14,17,20,23-pentaoxa-4,11-diaza-hexacosan-26-oate (11)

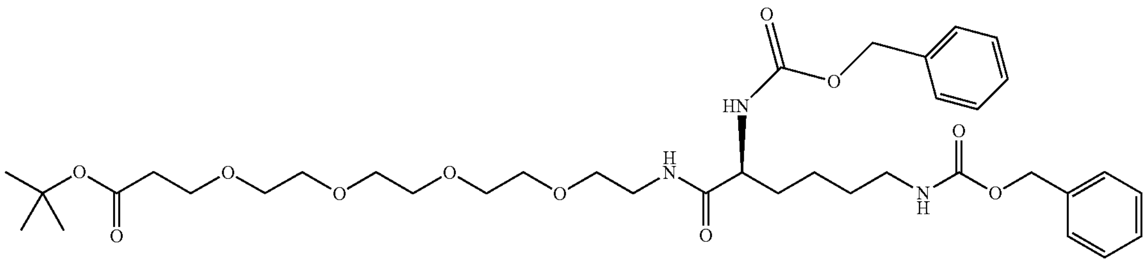 [SMILES: CC(C)(C)OC(=O)CCOCCOCCOCCOCCNC(=O)[C@H](CCCCNC(=O)OCc1ccccc1)NC(=O)OCc1ccccc1]

To a solution of 10 (1 eq., 500.0 mg, 1.56 mmol.) and 9 (1 eq., 644.7 mg, 1.56 mmol.) in anhydrous DMF (15.6 mL), PYBOP (1.5 eq., 1.21 g, 2.33 mmol.) was added followed by DIPEA (5 eq., 1.00 g, 1.29 mL, 7.78 mmol.). The mixture was stirred at r.t. overnight.

The crude was evaporated until dryness and purified on silica gel (EtOAc): Yield 90% (1.00 g, 1.39 mmol).

Rf: 0.15 (EtOAc), $^1$H NMR (400 MHz, $CDCl_3$) δ=1.32-1.39 (m, 2H), 1.43 (s, 9H), 1.46-1.54 (m, 2H), 1.60-1.69 (m, 1H), 1.78-1.86 (m, 1H), 2.47 (t, J=6.5, 2H), 3.16 (q, J=6.7, 2H), 3.39-3.46 (m, 2H), 3.51-3.53 (m, 2H), 3.55-3.64 (m, 12H), 3.67 (t, J=6.6, 2H), 4.14 (q, J=7.3, 1H), 5.05-5.08 (m, 5H), 5.68 (d, J=8.1, 1H), 6.74 (d, J=5.4, 1H), 7.26-7.41 (m, 10H). $^{13}$C NMR (101 MHz, $CDCl_3$) δ 22.4, 28.2, 29.5, 32.5, 36.3, 39.4, 40.5, 54.9, 66.7, 66.9, 67.0, 69.7, 70.3, 70.4, 70.5, 70.6, 70.6, 80.7, 128.1, 128.2, 128.2, 128.2, 128.6, 128.6, 136.4, 136.8, 156.3, 156.7, 171.0, 171.8. HRMS (ESI): calculated for $C_{37}H_{56}N_{3011}$+[M+H]$^+$: 718,3909, found 718.3917.

Tert-butyl (S)-18,22-diamino-17-oxo-4,7,10,13-tetraoxa-16-azadocosanoate (12)

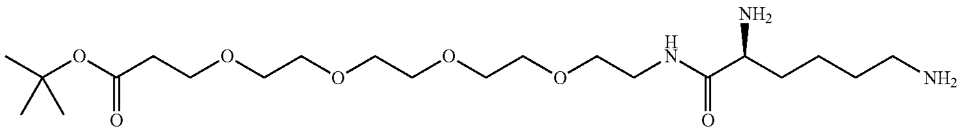 [SMILES: CC(C)(C)OC(=O)CCOCCOCCOCCOCCNC(=O)[C@@H](N)CCCCN]

To a degazed solution of 11 (1 eq., 1.00 g, 1.39 mmol) in MeOH (20 mL) was added $Pd(OH)_2$ (100.0 mg). The suspension was stirred overnight under $H_2$ atmosphere.

The crude was filtered over celite and evaporated until dryness to produce the title compound: Yield 99% (621.0 mg, 1.38 mmol).

$^1$H NMR (400 MHz, $CDCl_3$) δ=1.44 (s, 14H), 1.78-1.86 (m, 5H), 2.51 (t, J=6.5, 2H), 2.74 (tq, J=12.7, 6.6, 2H), 3.37 (dd, J=7.6, 5.8, 2H), 3.50-3.67 (m, 14H), 3.72 (t, J=6.5, 2H), 7.80 (s, 1H). $^{13}$C NMR (101 MHz, $CDCl_3$) δ 23.1, 28.2, 32.3, 35.1, 36.4, 38.9, 41.8, 55.2, 67.1, 70.0, 70.3, 70.4, 70.6, 70.7, 76.8, 77.2, 77.5, 80.7, 171.1, 175.6. HRMS (ESI): calculated for $C_{21}H_{44}N_3O_7$+[M+H]$^+$: 450.3174, found 450.3191.

Tert-butyl 1-[2,6-bis({3-[2-(2-{[(benzyloxy)carbonyl]amino}ethoxy)ethoxy]propanamido})hexanamido]-3,6,9,12-tetraoxapentadecan-15-oate (14)

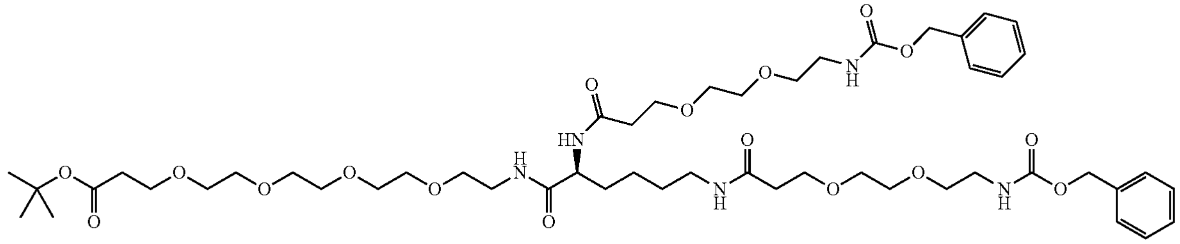 [SMILES: CC(C)(C)OC(=O)CCOCCOCCOCCOCCNC(=O)[C@H](CCCCNC(=O)CCOCCOCCNC(=O)OCc1ccccc1)NC(=O)CCOCCOCCNC(=O)OCc1ccccc1]

To a solution of 12 (1 eq., 300.0 mg, 0.67 mmol.) and 13 (2.1 eq., 436.3 mg, 1.40 mmol.) in anhydrous DMF (6.7 mL), PYBOP (3 eq., 1.04 g, 2.00 mmol.) was added followed by DIPEA (10 eq., 862.4 mg, 1.10 mL, 6.67 mmol.). The mixture was stirred at r.t. overnight.

The crude was evaporated until dryness and purified reverse phase: $H_2O/CH_3CN$ to isolate the title compound: Yield: 71% (489.0 mg, 0.47 mmol).

Rf: 0.45 (DCM/MeOH: 9/1), $^1$H NMR (400 MHz, Methanol-$d_4$) δ=1.31-1.41 (m, 2H), 1.45-1.53 (s+m, 11H), 1.58-1.67 (m, 1H), 1.74-1.83 (m, 1H), 2.41 (t, J=6.2, 2H), 2.45-2.50 (m, 4H), 3.15 (t, J=6.9, 2H), 3.27-3.31 (m, 3H), 3.33-3.37 (m, 3H), 3.50-3.54 (m, 6H), 3.57-3.63 (m, 20H), 3.67-3.74 (m, 6H), 4.31 (dd, J=8.9, 5.3, 1H), 5.07 (large s, 4H), 7.08-7.58 (m, 10H). $^{13}$C NMR (101 MHz, Methanol-$d_4$) δ 24.2, 28.4, 30.0, 32.9, 37.2, 37.5, 37.7, 40.1, 40.4, 41.7, 54.6, 67.4, 67.9, 68.2, 68.3, 70.5, 70.9, 71.0, 71.2, 71.2, 71.3, 71.3, 71.3, 71.4, 71.5, 71.6, 71.6, 81.7, 128.8, 128.9, 129.0, 129.5, 138.4, 158.9, 172.8, 173.8, 173.9, 174.3. HRMS (ESI): calculated for $C_{51}H_{82}N_5O_{17}{}^+[M+H]^+$: 1036.5718, found 1036.5700.

Tert-butyl 1-[2,6-bis({3-[2-(2-aminoethoxy)ethoxy]propanamido})hexanamido]-3,6,9,12-tetraoxapentadecan-15-oate (15)

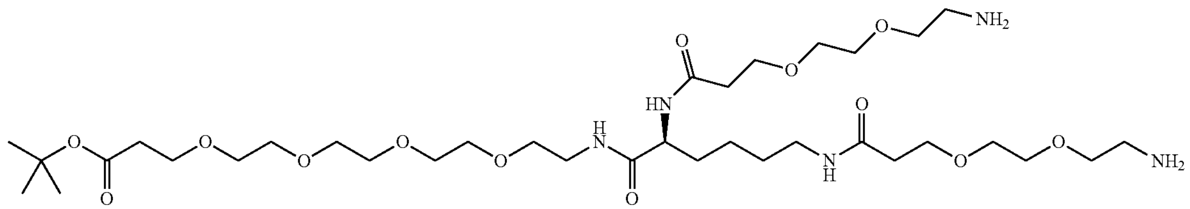 [SMILES: CC(C)(C)OC(=O)CCOCCOCCOCCOCCNC(=O)[C@H](CCCCNC(=O)CCOCCOCCN)NC(=O)CCOCCOCCN]

To a degazed solution 14 (1 eq., 480.0 mg, 0.46 mmol.) in MeOH (10 mL) was added $Pd(OH)_2$ (48.0 mg). The suspension was stirred overnight under $H_2$ atmosphere. The crude was filtered over celite and evaporated until dryness to produce the title compound: Yield 100% (355.0 mg, 0.46 mmol).

$^1$H NMR (400 MHz, Methanol-$d_4$) δ=1.23-1.33 (m, 2H), 1.36 (s, 9H), 1.40-1.47 (m, 2H), 1.53-1.61 (m, 1H), 1.66-1.74 (m, 1H), 2.34-2.51 (m, 6H), 3.01-3.10 (m, 6H), 3.27-3.30 (m, 2H), 3.44-3.47 (m, 2H), 3.49-3.72 (m, 30H), 4.20 (dd, J=8.6, 5.5, 1H). $^{13}$C NMR (101 MHz, Methanol-$d_4$) δ 24.2, 28.4, 30.0, 32.9, 37.2, 37.2, 37.5, 40.1, 40.3, 40.7, 40.8, 54.8, 67.9, 67.9, 68.1, 68.3, 70.6, 71.2, 71.3, 71.3, 71.3, 71.4, 71.5, 81.8, 173.7, 173.9, 173.9, 174.5. HRMS (ESI): calculated for $C_{35}H_{70}N_5O_{13}{}^+[M+H]$: 768.4965, found 768.4972.

Scheme 6 Synthesis of the Cy5.5 dimers (compounds 6 and 7) and DY647 dimers (compounds C and D).
2nd generation CY5.5 dimers
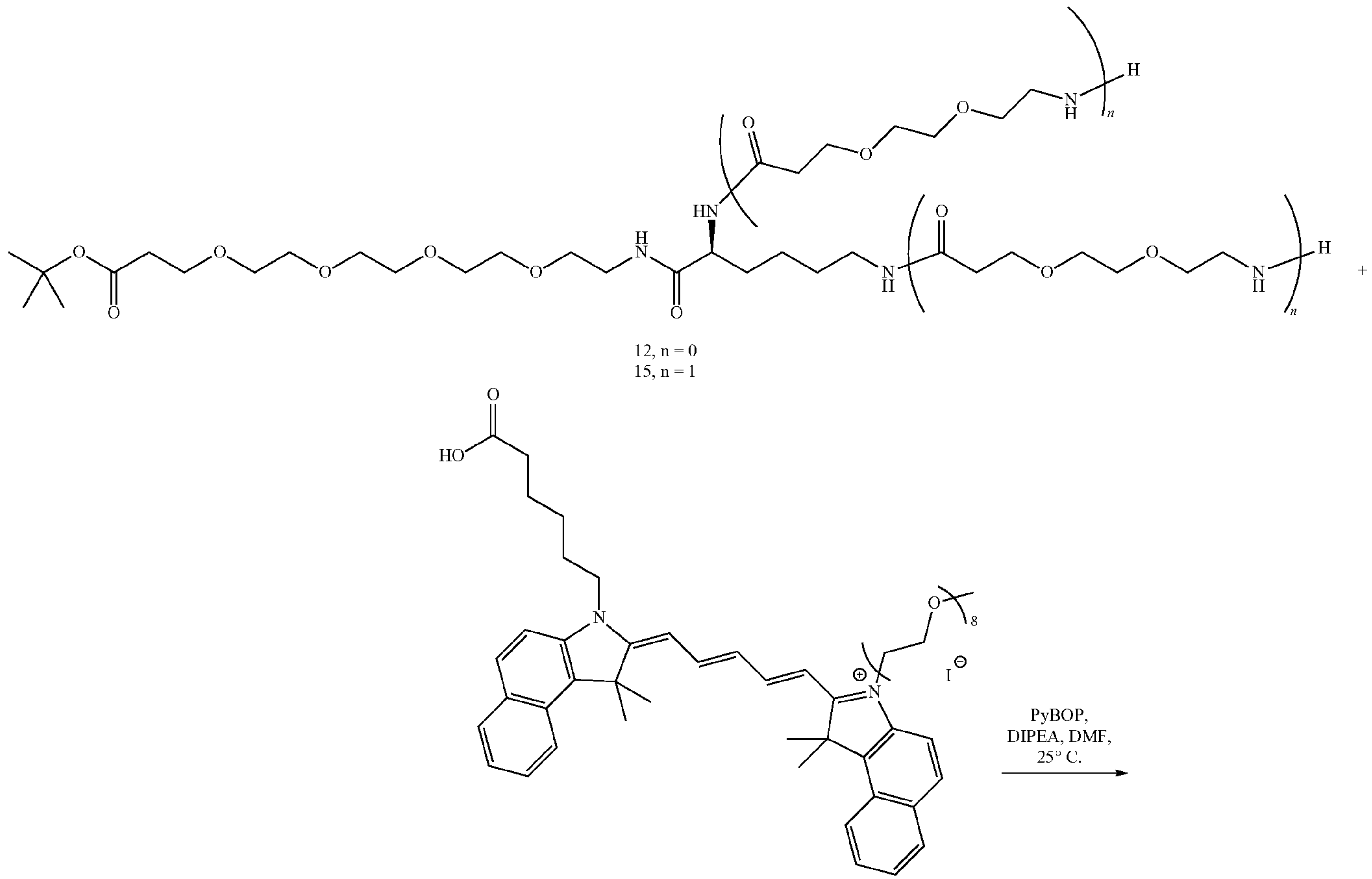
12, n = 0
15, n = 1
16

-continued
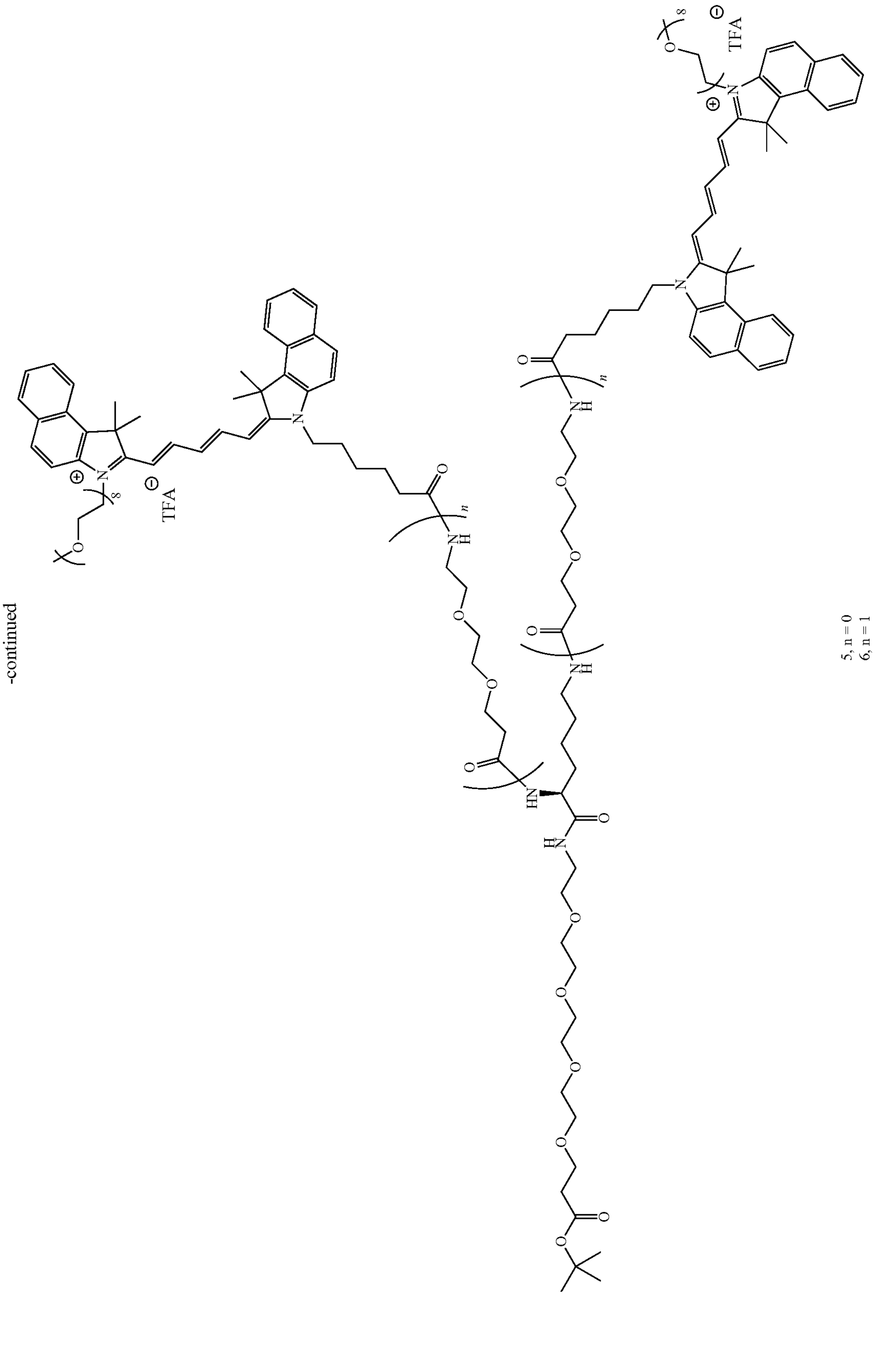
5, n = 0
6, n = 1

-continued
2nd generation DY647 dimers
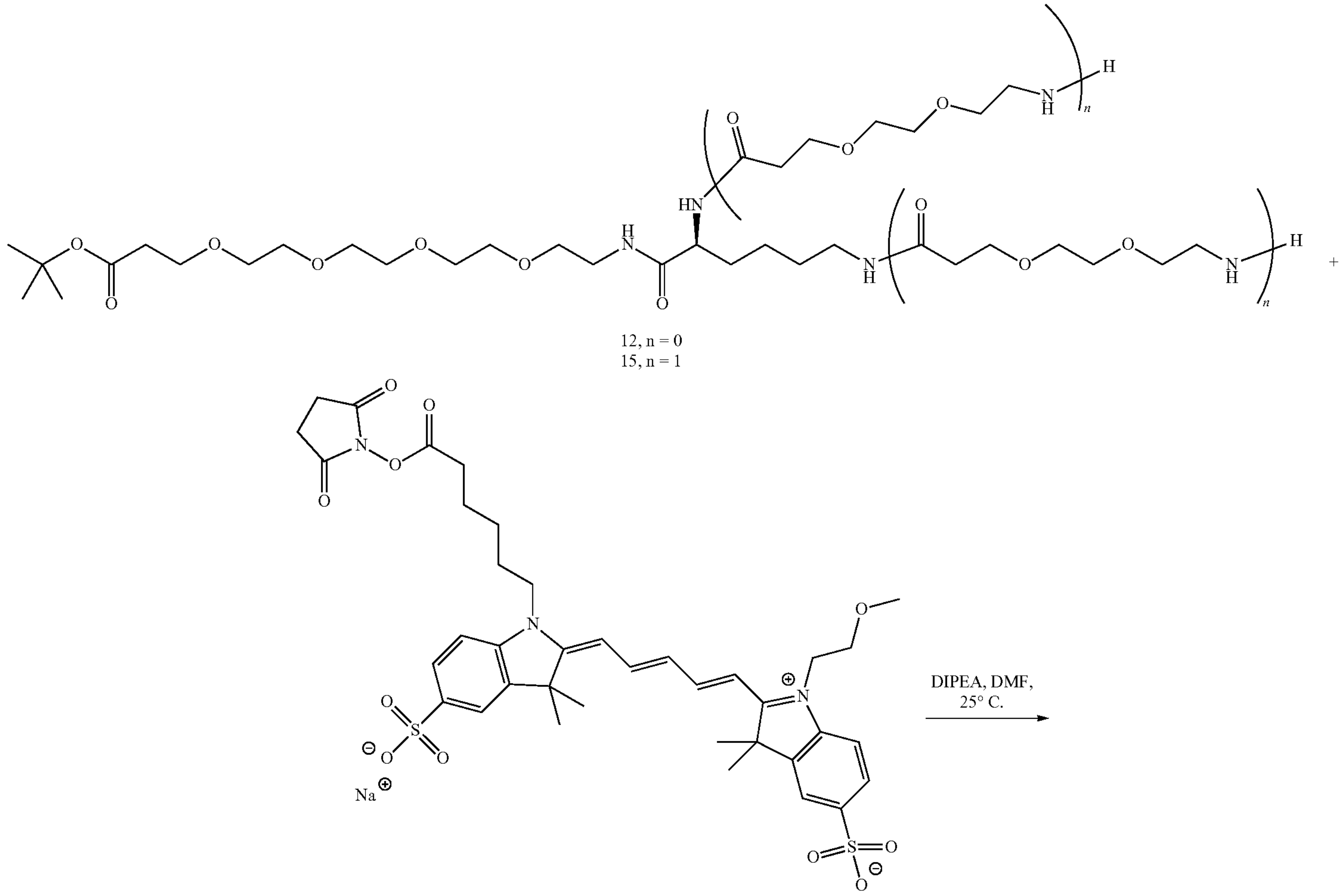
12, n = 0
15, n = 1
17

-continued
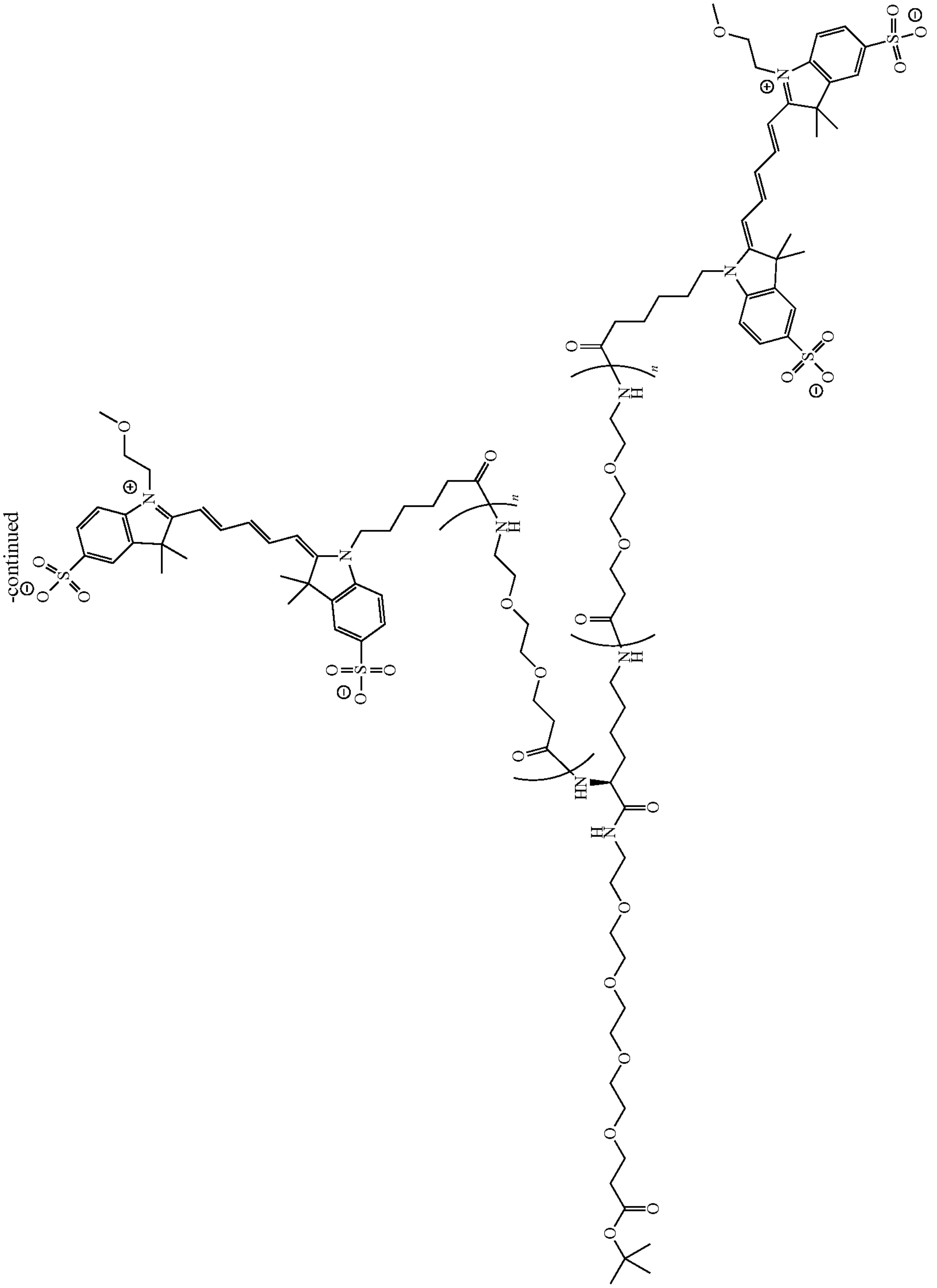
7, n = 0
8, n = 1

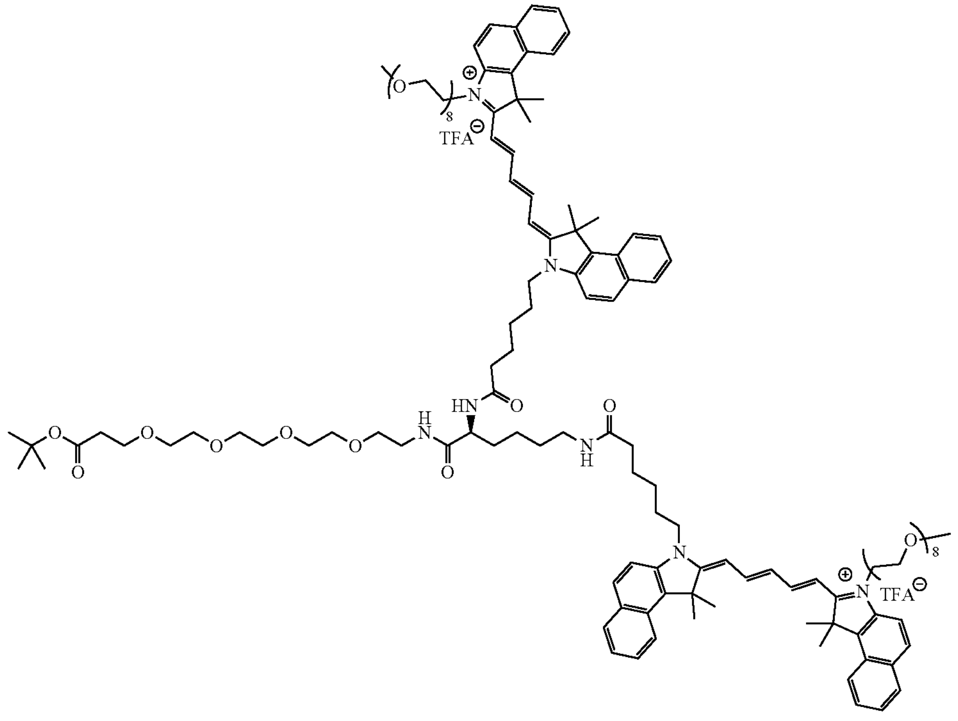

To a solution of 12 (1 eq., 0.1 mg, 0.33 μmol) in anhydrous DMF (50 μL) were added a solution of 16 (1.9 eq., 0.7 mg, 0.62 μmol) in anhydrous DMF (50 μL), PYBOP (2 eq., 0.3 mg, 0.65 μmol) and DIPEA (4 eq., 0.2 μL, 1.31 μmol). The mixture was stirred at 25° C. for 3 h. $H_2O$ (100 μL) was added and the crude product was purified by reverse-phase semi-preparative HPLC using a linear gradient of 30-95% v/v ACN (0.1% v/v TFA) in $H_2O$ (0.10% v/v TFA) to afford after lyophilization a blue solid (0.5 mg, 61%).

HRMS (ESI): calculated for $C_{133}H_{189}N_{7025}$+-M]$^2$+: 2284.3733, found 2284.3803.

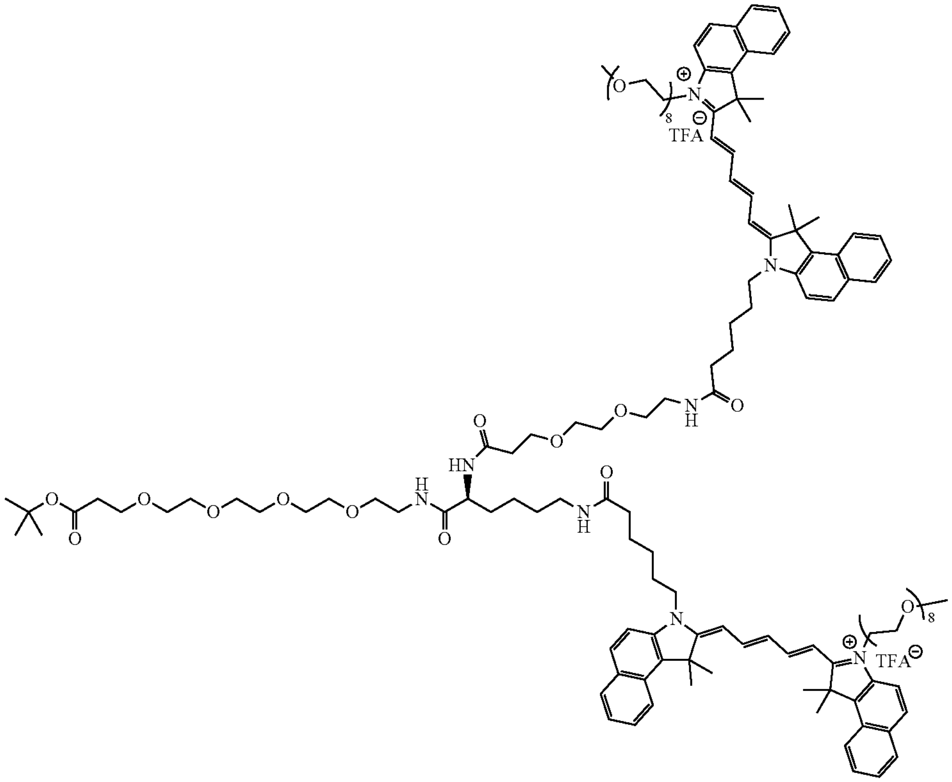

To a solution of 15 (1 eq., 0.3 mg, 0.33 mol) in anhydrous DMF (50 μL) were added a solution of 16 (1.9 eq., 0.7 mg, 0.62 mol) in anhydrous DMF (50 μL), PYBOP (2 eq., 0.3 mg, 0.65 mol) and DIPEA (4 eq., 0.2 μL, 1.31 mol). The mixture was stirred at 25° C. for 3 h. $H_2O$ (100 μL) was added and the crude product was purified by reverse-phase semi-preparative HPLC using a linear gradient of 30-95% v/v ACN (0.1% v/v TFA) in $H_2O$ (0.1% v/v TFA) to afford after lyophilization a blue solid (0.6 mg, 65%).

HRMS (ESI): calculated for $C_{147}H_{215}N_9O_{31}^{2+}$ [M]2+: 2602.5524, found 2602.5580.

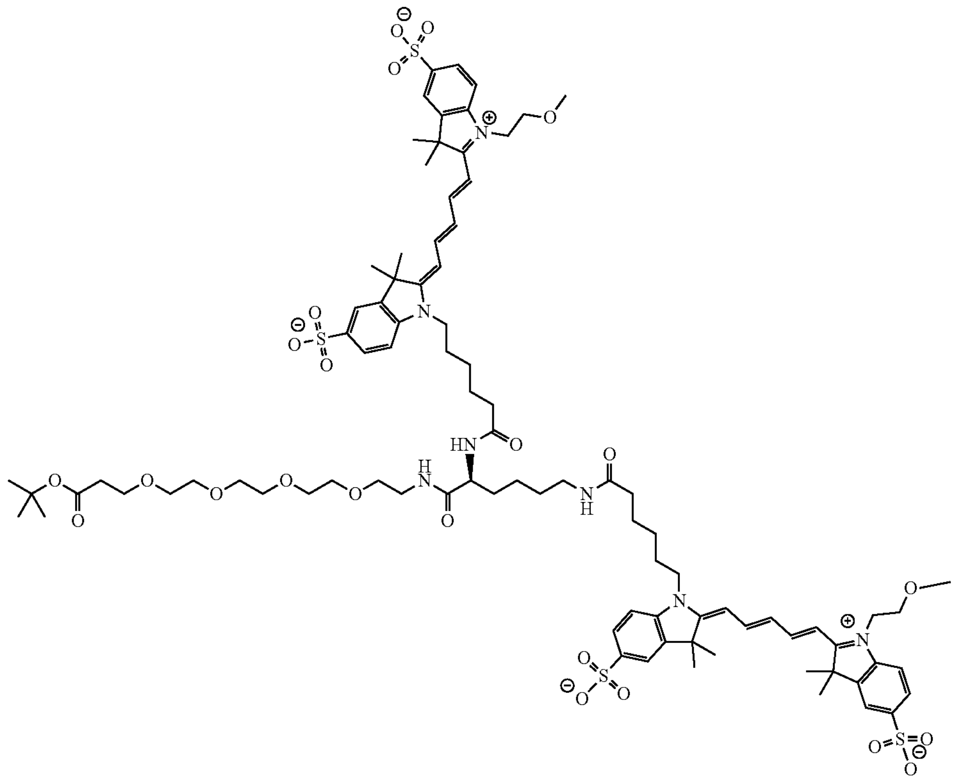

To a solution of 12 (1 eq., 0.1 mg, 0.33 mol) in anhydrous DMF (50 μL) were added a solution of 17 (1.9 eq., 0.5 mg, 0.62 mol) in anhydrous DMF (50 μL) and DIPEA (4 eq., 0.2 μL, 1.31 μmol). The mixture was stirred at 25° C. for 4.5 h. $H_2O$ (100 μL) was added and the crude product was purified by reverse-phase semi-preparative HPLC using a linear gradient of 10-75% v/v ACN (0.1% v/v TFA) in $H_2O$ (0.1% v/v TFA) to afford after lyophilization a blue solid (0.4 mg, 69%).

HRMS (ESI): calculated for $C_{89}H_{125}N_7O_{23}S_4^{2+}$[M+4H] 2+/2: 893.8855, found 893.8863.

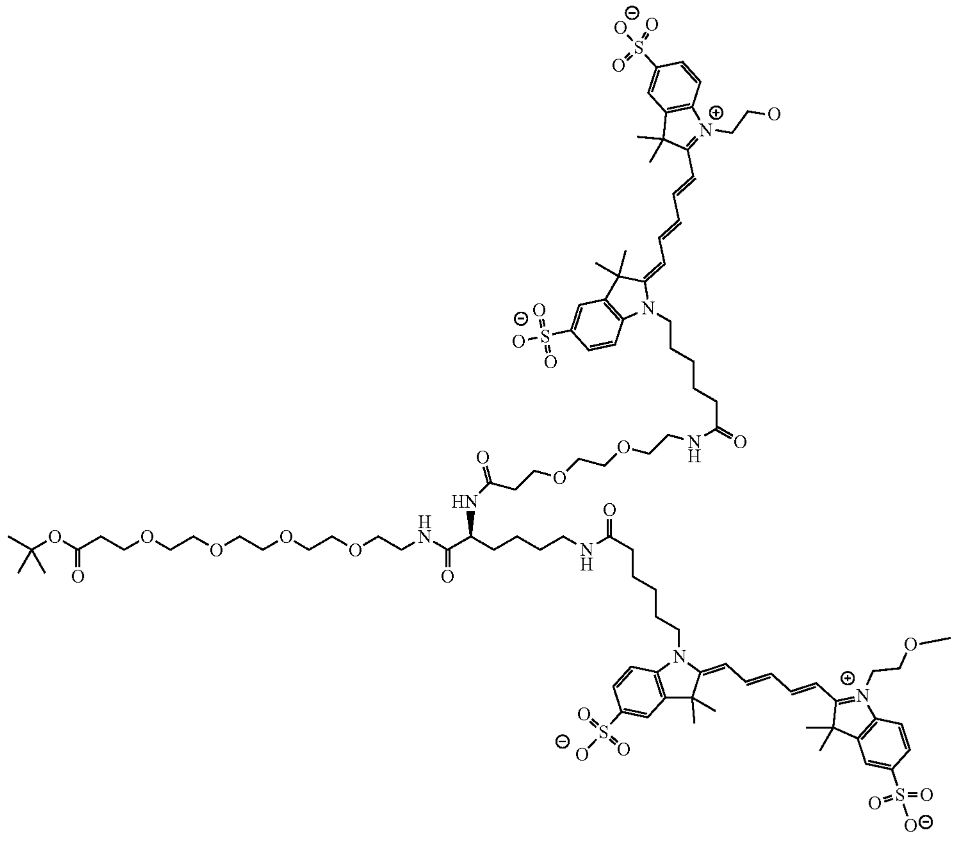

To a solution of 15 (1 eq., 0.3 mg, 0.33 mol) in anhydrous DMF (50 μL) were added a solution of 17 (1.9 eq., 0.5 mg, 0.62 mol) in anhydrous DMF (50 μL) and DIPEA (4 eq., 0.2 μL, 1.31 μmol). The mixture was stirred at 25° C. for 4.5 h. $H_2O$ (100 μL) was added and the crude product was purified by reverse-phase semi-preparative HPLC using a linear gradient of 10-75% v/v ACN (0.1% v/v TFA) in $H_2O$ (0.1% v/v TFA) to afford after lyophilization a blue solid (0.3 mg, 44%).

HRMS (ESI): calculated for $C_{103}H_{151}N_9O_{29}S_4^{2+}$[M+4H] 2+/2: 1052.9750, found 1052.9744.

Absorption and Fluorescence Spectroscopy

General Information

Cy5.5 Dimers

Absorption spectra were recorded on a Shimadzu UV-2700i spectrophotometer and fluorescence spectra on a Horiba Fluoromax 4 spectrofluorometer. Fluorescence emission spectra were systematically recorded at 630 nm excitation wavelength at 20° C. All fluorescence spectra were corrected for instrumental effects. Fluorescence quantum yields (QY) were measured using Rhodamine 800 in EtOH as a reference (QY=25%).[ref] Turn-ON were calculated as a ratio of QY of compounds in EtOH to QY in water.

Ref A. Alessi, M. Salvalaggio, G. Ruzzon, *J. Lumin.* 2013, 134, 385-389.

DY647 Dimers

Absorption spectra were recorded on a Shimadzu UV-2700i spectrophotometer and fluorescence spectra on a Horiba Fluoromax 4 spectrofluorometer. Fluorescence emission spectra were systematically recorded at 600 nm excitation wavelength at 20° C. All fluorescence spectra were corrected for instrumental effects. Fluorescence quantum yields (QY) were measured using DID in MeOH as a reference (QY=33%).[ref] *Turn-ON were calculated as a ratio of QY of compounds in EtOH to QY in water.*

Ref I. Texier, et al., *J. Biomed. Opt.* 2009, 14, 054005.

TABLE 4

| | Cy5.5 dimers | | | | | | DY647 dimers | | | | | |
|---|---|---|---|---|---|---|---|---|---|---|---|---|
| | 6 (n = 0) | | | 7 (n = 1) | | | C (n = 0) | | | D (n = 1) | | |
| Solvent | $\lambda_{abs}$, nm[a] | $\lambda_{em}$, nm[b] | QY, %[c] | $\lambda_{abs}$, nm[a] | $\lambda_{em}$, nm[b] | QY, %[c] | $\lambda_{abs}$, nm[a] | $\lambda_{em}$, nm[b] | QY, %[c] | $\lambda_{abs}$, nm[a] | $\lambda_{em}$, nm[b] | QY, %[c] |
| Acetone | 684 | 709 | 17.2 | 685 | 709 | 23.3 | 667 | 685 | 18.6 | 663 | 683 | 11.7 |
| Acetonitrile | 681 | 705 | 14.7 | 681 | 703 | 20.7 | 657 | 678 | 23.7 | 654 | 677 | 21.1 |
| EtOH | 685 | 710 | 21.2 | 685 | 711 | 25.5 | 656 | 679 | 29.4 | 655 | 676 | 32.0 |

TABLE 4-continued

| | Cy5.5 dimers | | | | | | DY647 dimers | | | | | |
|---|---|---|---|---|---|---|---|---|---|---|---|---|
| | 6 (n = 0) | | | 7 (n = 1) | | | C (n = 0) | | | D (n = 1) | | |
| Solvent | $\lambda_{abs}$, nm[a] | $\lambda_{em}$, nm[b] | QY, %[c] | $\lambda_{abs}$, nm[a] | $\lambda_{em}$, nm[b] | QY, %[c] | $\lambda_{abs}$, nm[a] | $\lambda_{em}$, nm[b] | QY, %[c] | $\lambda_{abs}$, nm[a] | $\lambda_{em}$, nm[b] | QY, %[c] |
| MeOH | 682 | 705 | 15.8 | 681 | 707 | 19.7 | 649 | 674 | 27.3 | 650 | 672 | 31.7 |
| $H_2O$ | 629 | 701 | 0.2 | 628 | 708 | 0.4 | 646 | 669 | 3.8 | 648 | 669 | 6.1 |

Photophysical properties of the 2nd generation dimers.
[a]Position of the absorption maximum.
[b]Position of the emission maximum.
[c]Fluorescence quantum yield.

TABLE 5

| Fluorescence turn-on for the dimers, calculated as a ratio of quantum yields in EtOH to that in water (200 nM). | |
|---|---|
| Fluorogenic dimer | Turn-on |
| 6 (Cy5.5, n = 0) | 106 |
| 7 (Cy5.5, n = 1) | 64 |
| C (DY647, n = 0) | 7.7 |
| D (DY647, n = 1) | 5.2 |

Conclusions

1) The results show that the PEG moiety between the fluorophore moiety and the lysine moiety is not necessary to get a better Turn-ON response. The turn-on response is even better without a PEG linker (106 vs 64, respectively for compounds 6 and 7).
2) Substitution of Cy5.5 fluorophore by Dy647 (a negatively charged fluorophore) reduces the Turn-ON efficacy harshly.

The invention claimed is:

1. A compound, which is a fluorogenic dimer with two cyanine moieties (D) and a branched linker having three branches (L), which is represented by the following formula (1): D-L-D (1);

where (D) is represented by the following formula (I) or (I'):

(I)

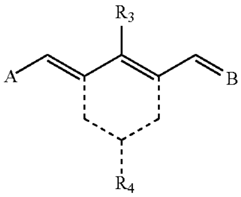

or (I')

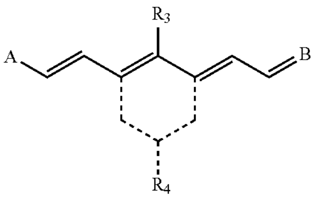

wherein:

(A) has the following formula:

(A)

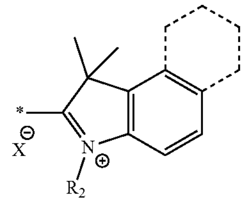

(B) has the following formula:

(B)

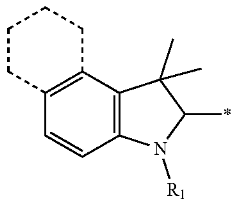

where the dashed lines are present or not, and, when they are present, they represent single or double carbon bonds;

$R_2$ is a $(C_2\text{-}C_{10})$alkyl group substituted by a functional group selected from —COOH, —$SO_3H$, and OH; a polyethylene glycol represented by the formula —$(CH_2CH_2O)_n$—R'; or a polypropylene glycol represented by the formula —$(CH_2CH_2(CH_3)O)_n$—R', wherein n is an integer from 1 to 40 and R' is an alkyl group in $C_1\text{-}C_{12}$, comprising optionally at least one functional group consisting of —COOH, —$SO_3H$, and OH;

$R_3$ represents:

a hydrogen atom, a halogen atom, a group selected from a $(C_1\text{-}C_{20})$alkyl, a cyclo$(C_3\text{-}C_{20})$alkyl, a $(C_2\text{-}C_{20})$alkenyl, a $(C_2\text{-}C_{20})$alkynyl, a $(C_1\text{-}C_5)$alkyl-NR"R"' (R" and R"' being independently H or a $(C_1\text{-}C_5)$alkyl), a heterocyclic group, a cyclo$(C_3\text{-}C_{20})$alkenyl, a heterocyclo$(C_2\text{-}C_{20})$alkenyl, an aryl, a heteroaryl, a hetero$(C_1\text{-}C_{20})$alkyl, a $(C_1\text{-}C_{20})$alkylaryl, and a $(C_1\text{-}C_{20})$alkylheteroaryl, said group being unsubstituted or substituted by one or two substituents selected from a $(C_1\text{-}C_5)$ alkyl, an aryl, an aryl$(C_1\text{-}C_5)$alkyl, —$CONR_{11}R_{12}$, or —$R_{13}$COOH, $R_{11}$ and $R_{12}$ being independently a hydrogen, a $(C_1\text{-}C_{20})$ alkyl, a di$(C_1\text{-}C_5)$alkylamino$(C_1\text{-}C_5)$alkyl, optionally substituted by one or more halogen atoms or hydroxy groups, polyethylene glycol represented by the formula —$(CH_2CH_2O)_n$—R'; or a polypropylene glycol represented by the formula —$(CH_2CH_2(CH_3)O)_n$—R', wherein n is an integer from 1 to 40 and R' is an alkyl group in $C_1$-$C_{12}$, or, alternatively, $R_{11}$ and $R_{12}$ represents with the nitrogen to which they are attached an heterocycle optionally substituted by a ($C_1$-$C_4$)alkyl, $R_{13}$ being a ($C_1$-$C_{10}$) alkyl, one substituent can optionally be substituted by one or two substituents as defined herein, or a group of formula -E-$R_{10}$, wherein E is selected from —O—, —S—, —NR"—(R" being H or a ($C_1$-$C_4$)alkyl), and —$CH_2$—; and $R_{10}$ is selected from a ($C_1$-$C_{20}$)alkyl, a cyclo($C_3$-$C_{20}$)alkyl, a ($C_2$-$C_{20}$)alkenyl, a ($C_2$-$C_{20}$)alkynyl, a ($C_1$-$C_5$)alkyl-NR"R'" (R" and R'" being independently H or a ($C_1$-$C_5$)alkyl), a heterocyclic group, a cyclo($C_3$-$C_{20}$)alkenyl, a heterocyclo($C_2$-$C_{20}$)alkenyl, an aryl, a heteroaryl, a hetero($C_1$-$C_{20}$)alkyl, a ($C_1$-$C_{20}$)alkylaryl, a ($C_1$-$C_{20}$)alkylheteroaryl, $R_{10}$ being unsubstituted or substituted by one to three substituents selected from a ($C_1$-$C_5$) alkyl, an aryl, an aryl($C_1$-$C_5$)alkyl, —$CONR_{11}R_{12}$, or —$R_{13}COOH$;

$R_{11}$ and $R_{12}$ being independently a hydrogen, a ($C_1$-$C_{20}$) alkyl, a di($C_1$-$C_5$)alkylamino($C_1$-$C_5$)alkyl, optionally substituted by one or more halogen atoms or hydroxy groups, or, alternatively, or alternatively $R_{11}$ and $R_{12}$ represents with the nitrogen to which they are attached an heterocycle optionally substituted by a ($C_1$-$C_4$)alkyl, $R_{13}$ being a ($C_1$-$C_{10}$) alkyl, one substituent can optionally be substituted by one or two substituents as defined herein, $R_4$, if present, represents:

a hydrogen atom, a group selected from a ($C_1$-$C_{20}$)alkyl, a cyclo($C_3$-$C_{20}$)alkyl, a ($C_2$-$C_{20}$)alkenyl, a ($C_2$-$C_{20}$)alkynyl, a heterocyclic group, a cyclo($C_3$-$C_{20}$)alkenyl, a heterocyclo($C_2$-$C_{20}$)alkenyl, an aryl, a heteroaryl, a hetero($C_1$-$C_{20}$)alkyl, a ($C_1$-$C_{20}$)alkylaryl, or a ($C_1$-$C_{20}$)alkylheteroaryl, said group being unsubstituted or substituted by one or two substituents selected from a ($C_1$-$C_5$) alkyl, an aryl, or —$R_{13}COOH$, $R_{13}$ being a ($C_1$-$C_{20}$) alkyl, or a group of formula -E-$R_{10}$, wherein E is selected from —O—, —S—, —NH—, or —$CH_2$—; $R_{10}$ is selected from a ($C_1$-$C_{20}$)alkyl, a cyclo($C_3$-$C_{20}$)alkyl, a ($C_2$-$C_{20}$)alkenyl, a ($C_2$-$C_{20}$)alkynyl, a heterocyclic group, a cyclo($C_3$-$C_{20}$)alkenyl, a heterocyclo($C_2$-$C_{20}$)alkenyl, an aryl, a heteroaryl, a hetero($C_1$-$C_{20}$)alkyl, a ($C_1$-$C_{20}$)alkylaryl, a ($C_1$-$C_{20}$)alkylheteroaryl, $R_{10}$ being unsubstituted or substituted by one to three substituents selected from a ($C_1$-$C_5$) alkyl, an aryl, or —$R_{13}COOH$, $R_{13}$ being a ($C_1$-$C_{10}$) alkyl;

$R_1$, on each cyanine moiety, is a saturated or unsaturated hydrocarbon chain covalently bonded to a branch of in formula (1), L is a branched saturated or unsaturated hydrocarbon group of 2 to 40 carbon atoms having three branches, two of said branches being covalently bonded to cyanine moieties of formulae (I) or (I') via $R_1$ on each cyanine moiety and the third branch is the remainder of the branched saturated or unsaturated hydrocarbon group and comprises a group able to react through a click reaction or a bioconjugation reaction or is attached to a ligand;

wherein $R_1$ and L, independently, is optionally interrupted by one or several heteroatoms, by one or several connecting groups, or by one or several carbon cycles or heterocycles, $R_1$ and L, independently, may be further substituted by one or several groups selected from $C_1$-$C_3$ alkyl groups, halogens, —OH, —OMe, and —$CF_3$; and X is an anion bearing a negative charge.

2. The compound according to claim 1, wherein $R_1$ is a saturated hydrocarbon chain from 3 to 6 carbon atoms.

3. The compound according to claim 1, wherein linker L is a branched hydrocarbon group interrupted by one or more ethyleneoxy groups, ethylene groups, and interrupted by one or more connecting groups selected from the group consisting of: —O—, —NH—, —C(═O)—, —C(═O)NH—, —OC(═O)—, —(C═O)O—, —NHC(═O)—, —C(═O)NH—, —NHC(═O)NH—, —NHC(═O)O—, and —OC(═O)NH—.

4. The compound according to claim 1, wherein (D) is represented by the following formula (I) or (I'):

(I)

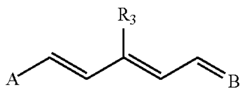

or (I')

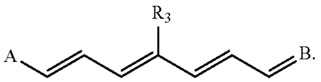

5. The compound according to claim 1, wherein (D) is represented by the following formula (I):

(I)

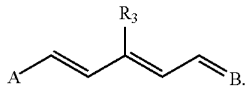

6. The compound according to claim 1, wherein the formula (A) is as follows:

(A1)

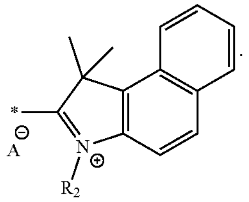

7. The compound according to claim 1, wherein the formula (B) is as follows:

(B1)

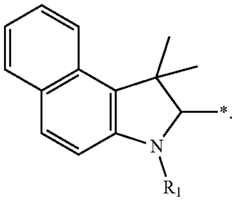

8. The compound according to claim 1, wherein the third branch of L comprises a group able to react through a click reaction or a bioconjugation reaction said group being an azido group or a strained alkyne scaffold.

9. The compound according to claim 1, wherein the third branch of L is linked to a ligand.

10. The compound according to claim 9, wherein the ligand is a ligand of a G protein-coupled receptor (GPCR) or the ligand is carbetocin.

11. The compound according to claim 1, wherein the compound has a formula selected from:

(2)

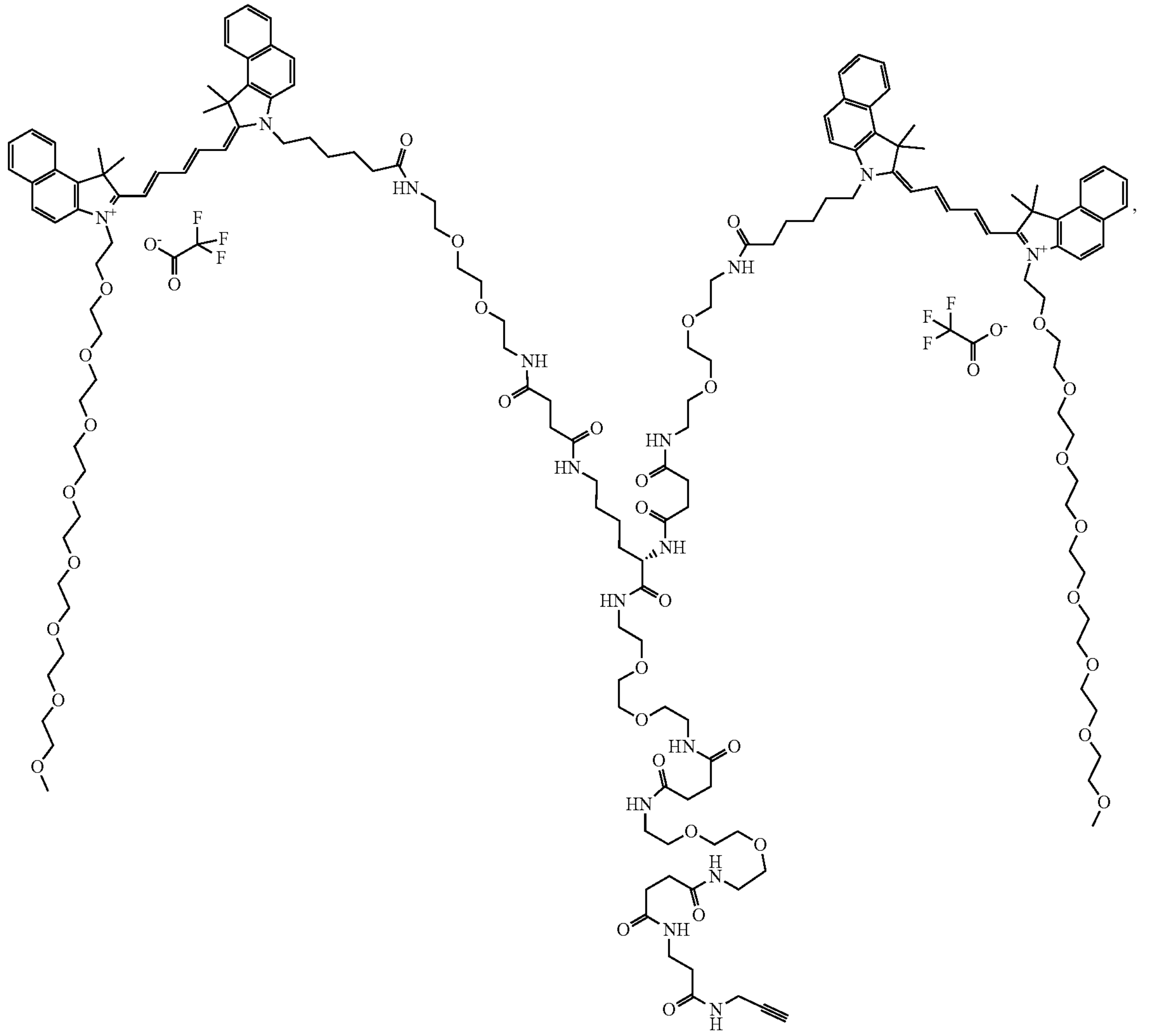

dCy5.5-PEG

-continued
(3)
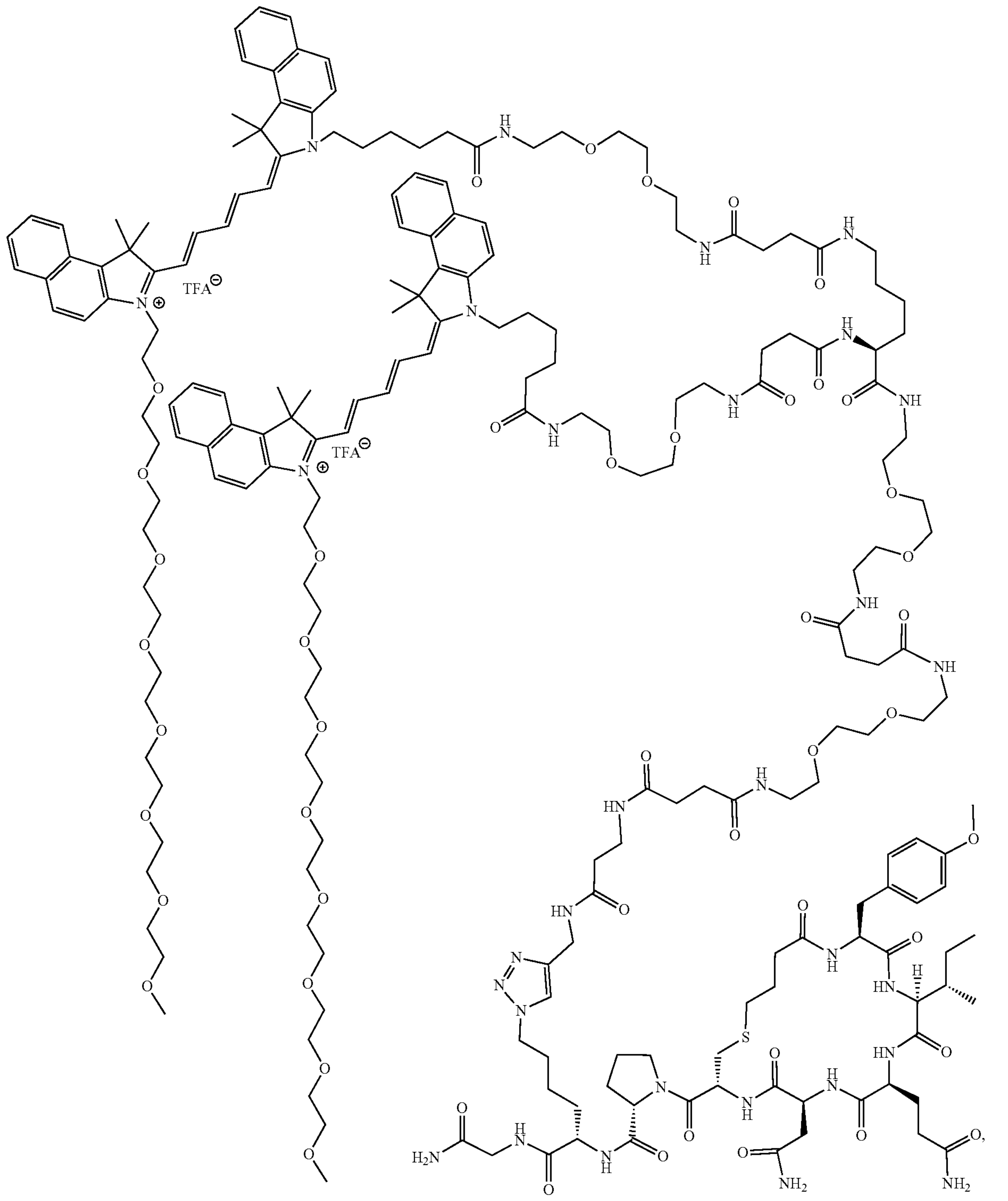
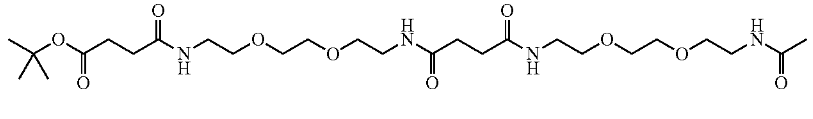

-continued

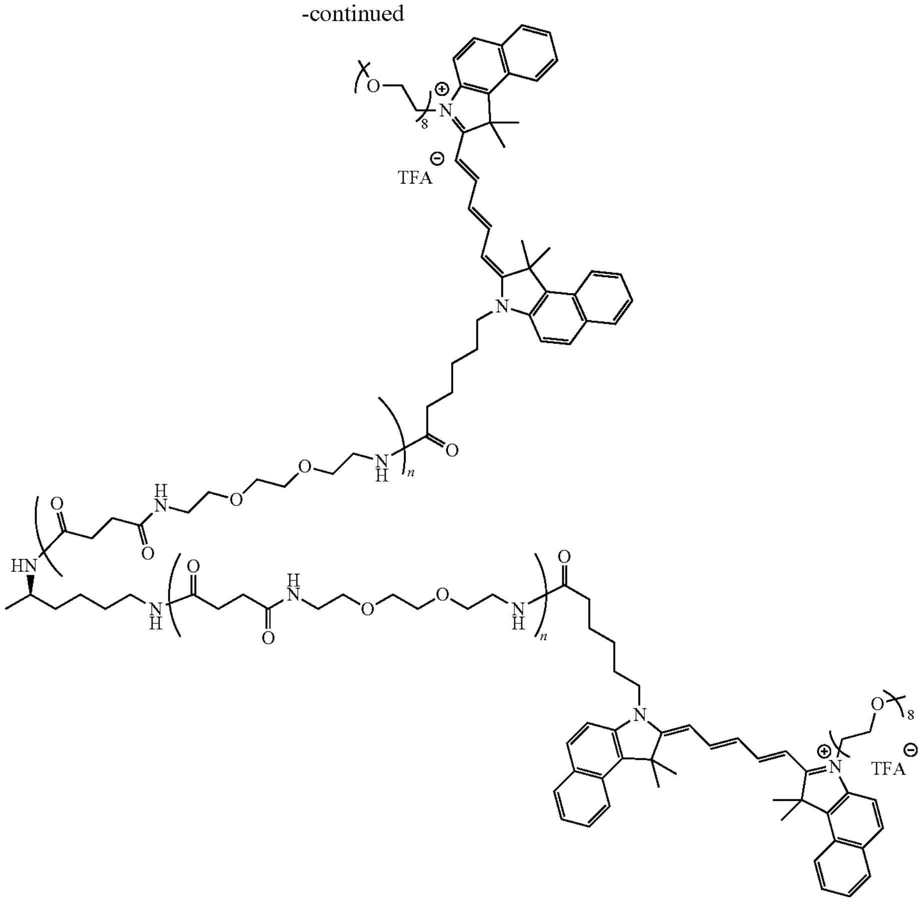

wherein n is 0 or 1 (compounds 4 and 5 respectively);

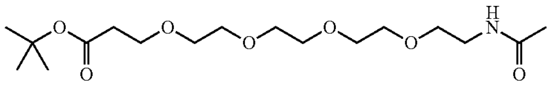

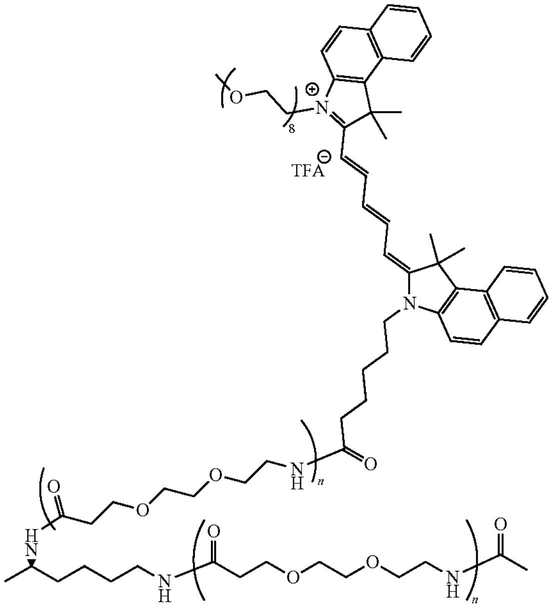

-continued

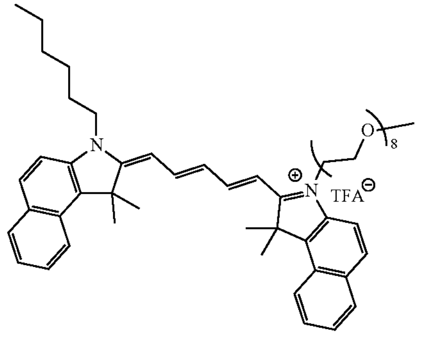

wherein n is 0 or 1 (compounds 6 and 7 respectively), wherein $TFA^-$ can be replaced by any other anion bearing a negative charge.

12. A pharmaceutical composition comprising a compound of Formula (1) as defined in claim 1, or a pharmaceutically acceptable solvate or hydrate thereof, and a pharmaceutically acceptable excipient.

13. The pharmaceutical composition according to claim 12, wherein the compound is of formula (2) or (3).

14. A method of labeling a molecular target, comprising the step of contacting the molecular target with a compound of Formula (1) as defined in claim 1, or a pharmaceutically acceptable solvate or hydrate thereof.

15. The method according to claim 14, wherein the compound of Formula (1) comprises a ligand that is a ligand of a G protein-coupled receptor (GPCR) or the ligand is carbetocin.

16. A kit which includes a container and at least one compound of Formula (1), or a pharmaceutically acceptable solvate or hydrate thereof, as defined in claim 1.

17. The compound according to claim 9, wherein the ligand is a membrane receptor ligand.

18. The compound according to claim 17, said compound being a probe for detecting a membrane receptor.

19. The method according to claim 14, wherein the molecular target is a membrane receptor and wherein the compound of Formula (1) comprises a ligand of said membrane receptor.

* * * * *